United States Patent
Kaufmann

(10) Patent No.: US 10,166,350 B2
(45) Date of Patent: Jan. 1, 2019

(54) ACTIVE DRY POWDER INHALER

(71) Applicant: Inspiro Medical Ltd., Nes Ziona (IL)

(72) Inventor: Nimrod Kaufmann, ModiIn (IL)

(73) Assignee: Inspiro Medical Ltd., Nes Ziona (IL)

( * ) Notice: Subject to any disclaimer, the term of this patent is extended or adjusted under 35 U.S.C. 154(b) by 0 days.

(21) Appl. No.: 15/125,173

(22) PCT Filed: Mar. 10, 2015

(86) PCT No.: PCT/IL2015/050248
§ 371 (c)(1),
(2) Date: Sep. 11, 2016

(87) PCT Pub. No.: WO2015/136529
PCT Pub. Date: Sep. 17, 2015

(65) Prior Publication Data
US 2017/0165439 A1 Jun. 15, 2017

Related U.S. Application Data

(60) Provisional application No. 61/950,256, filed on Mar. 10, 2014.

(51) Int. Cl.
*A61M 15/00* (2006.01)
*A61M 11/02* (2006.01)
*A61M 16/00* (2006.01)

(52) U.S. Cl.
CPC ........ *A61M 15/0041* (2014.02); *A61M 11/02* (2013.01); *A61M 15/0003* (2014.02);
(Continued)

(58) Field of Classification Search
CPC .... A61M 5/3015; A61M 13/00; A61M 15/00; A61M 15/0001; A61M 15/0003;
(Continued)

(56) References Cited

U.S. PATENT DOCUMENTS 2,946,332 A 7/1960 Sacks
3,948,264 A * 4/1976 Wilke ............... A61M 15/0028
128/203.15

(Continued)

FOREIGN PATENT DOCUMENTS

DE 19502725 8/1996
DE 19502725 A1 * 8/1996 ........ A61M 15/0028
(Continued)

OTHER PUBLICATIONS

English translation for DE 19502725, espacenet.com, Aug. 21, 2017.*

(Continued)

*Primary Examiner* — Rachel T Sippel
*Assistant Examiner* — Tu Vo

(57) ABSTRACT

A method of flowing a medicament including dry powder using gas, including preparing a medicament capsule with designated inflow and outflow apertures, introducing a volume of a gas to within a medicament capsule according to one or more release conditions, and releasing a therapeutically effective amount of the powder using the gas. In some embodiments, the medicament capsule apertures are prepared and/or gas delivered to it so that deagglomeration potentially occurs largely within the energetic flow conditions of the capsule, without significant trapping of residual powder by structures such as aperture edge irregularities.

21 Claims, 24 Drawing Sheets

(52) U.S. Cl.
CPC .... *A61M 15/0028* (2013.01); *A61M 15/0036* (2014.02); *A61M 15/002* (2014.02); *A61M 2016/0021* (2013.01); *A61M 2202/064* (2013.01); *A61M 2205/3334* (2013.01); *A61M 2205/502* (2013.01); *A61M 2206/16* (2013.01); *A61M 2230/205* (2013.01); *A61M 2230/30* (2013.01)

(58) Field of Classification Search
CPC .......... A61M 15/0005; A61M 15/0006; A61M 15/0008; A61M 15/001; A61M 15/0011; A61M 15/0013; A61M 15/0015; A61M 15/0016; A61M 15/0018; A61M 15/002; A61M 15/0023; A61M 15/0028; A61M 15/0031; A61M 15/0033; A61M 15/0035; A61M 15/0038; A61M 15/004; A61M 15/0041; A61M 15/0045; A61M 15/005; A61M 15/0051; A61M 15/0053; A61M 15/0055; A61M 15/0056; A61M 15/0058; A61M 15/006; A61M 15/0061; A61M 15/0063

See application file for complete search history.

(56) References Cited

U.S. PATENT DOCUMENTS

| | | | | |
|---|---|---|---|---|
| 3,971,377 A * | 7/1976 | Damani | ............ | A61M 15/0028 128/200.17 |
| 4,064,878 A * | 12/1977 | Lundquist | ......... | A61M 15/0028 128/203.15 |
| 4,338,931 A * | 7/1982 | Cavazza | ............ | A61M 15/0028 128/203.15 |
| 5,263,475 A * | 11/1993 | Altermatt | .......... | A61M 15/0065 128/203.15 |
| 5,301,666 A * | 4/1994 | Lerk | ................. | A61M 15/0045 128/203.15 |
| 5,522,383 A * | 6/1996 | Calvert | ............ | A61M 15/0028 128/203.15 |
| 5,596,982 A * | 1/1997 | Blaha-Schnabel | ......................... | A61M 15/0086 128/200.14 |
| 5,647,349 A * | 7/1997 | Ohki | ................. | A61M 15/0028 128/203.12 |
| 5,655,523 A | 8/1997 | Hodson et al. | | |
| 5,715,811 A * | 2/1998 | Ohki | ................. | A61M 15/0028 128/203.12 |
| 5,785,049 A * | 7/1998 | Smith | ............... | A61M 15/0045 128/203.15 |
| 5,823,183 A * | 10/1998 | Casper | .............. | A61M 15/0028 128/203.15 |
| 5,875,776 A * | 3/1999 | Vaghefi | ............. | A61M 15/0045 128/203.12 |
| 5,901,703 A * | 5/1999 | Ohki | ................. | A61M 15/0028 128/200.14 |
| 5,989,217 A * | 11/1999 | Ohki | ................. | A61M 15/0028 128/200.22 |
| 6,012,454 A | 1/2000 | Hodson et al. | | |
| 6,186,141 B1 * | 2/2001 | Pike | ........................ | A61B 18/12 128/203.12 |
| 6,192,876 B1 | 2/2001 | Denyer et al. | | |
| 6,398,074 B1 | 6/2002 | Bruna et al. | | |
| 7,117,867 B2 | 10/2006 | Cox et al. | | |
| 7,322,355 B2 | 1/2008 | Jones et al. | | |
| 7,458,373 B2 | 12/2008 | Nichols et al. | | |
| 7,520,278 B2 | 4/2009 | Crowder et al. | | |
| 7,559,325 B2 * | 7/2009 | Dunkley | ........... | A61M 15/0028 128/203.21 |
| 7,669,596 B2 * | 3/2010 | Alston | .............. | A61M 15/0028 128/203.12 |
| 7,708,011 B2 | 5/2010 | Hochrainer et al. | | |
| 7,819,116 B2 | 10/2010 | Brand et al. | | |
| 7,896,005 B2 | 3/2011 | Olsson et al. | | |
| 7,958,890 B2 | 6/2011 | Gieschen et al. | | |
| 8,205,611 B2 | 6/2012 | Olsson et al. | | |
| 8,245,705 B2 | 8/2012 | Li | | |
| 8,360,056 B2 * | 1/2013 | Ishizeki | ............ | A61M 15/0028 128/203.15 |
| 8,464,706 B2 | 6/2013 | Crockford et al. | | |
| 2001/0029948 A1 | 10/2001 | Ingle et al. | | |
| 2003/0131847 A1 * | 7/2003 | Niccolai | .......... | A61M 15/0028 128/203.15 |
| 2003/0168057 A1 | 9/2003 | Snyder et al. | | |
| 2003/0172926 A1 * | 9/2003 | Eason | ............... | A61M 15/0028 128/203.15 |
| 2004/0079368 A1 | 4/2004 | Gupta et al. | | |
| 2004/0089299 A1 | 5/2004 | Bonney et al. | | |
| 2005/0051166 A1 * | 3/2005 | Glusker | ............ | A61M 15/0028 128/203.21 |
| 2005/0056276 A1 | 3/2005 | Schuler et al. | | |
| 2005/0087189 A1 | 4/2005 | Crockford et al. | | |
| 2005/0263151 A1 | 12/2005 | Hochrainer et al. | | |
| 2006/0254583 A1 * | 11/2006 | Deboeck | .............. | A61K 9/0075 128/203.15 |
| 2007/0221216 A1 * | 9/2007 | Ganem | ............. | A61M 15/0028 128/203.12 |
| 2007/0272763 A1 | 11/2007 | Dunne et al. | | |
| 2008/0035143 A1 | 2/2008 | Sievers et al. | | |
| 2009/0095294 A1 | 4/2009 | Smyth et al. | | |
| 2009/0211577 A1 * | 8/2009 | Eistetter | ................. | A61M 11/06 128/203.15 |
| 2010/0108062 A1 * | 5/2010 | Ganem | ............. | A61M 15/0028 128/203.21 |
| 2011/0005523 A1 * | 1/2011 | Lalor | ................... | A61K 9/0075 128/203.15 |
| 2011/0220106 A1 * | 9/2011 | Ganem | ............. | A61M 15/0028 128/203.21 |
| 2011/0277752 A1 * | 11/2011 | Cheu | ................. | A61M 15/0028 128/200.14 |
| 2013/0267864 A1 | 10/2013 | Addington et al. | | |

FOREIGN PATENT DOCUMENTS

| | | | |
|---|---|---|---|
| DE | 19502725 B4 * | 3/2004 | ........ A61M 15/0028 |
| DE | 102005043449 | 8/2006 | |
| DE | 202011104129 | 12/2011 | |
| EP | 0796628 | 9/1997 | |
| EP | 1321160 | 6/2003 | |
| GB | 1436028 | 5/1976 | |
| WO | WO 2002/005879 | 1/2002 | |
| WO | WO 2011/077414 | 6/2011 | |
| WO | WO 2011/133740 | 10/2011 | |
| WO | WO 2015/136529 | 9/2015 | |

OTHER PUBLICATIONS

Communication Relating to the Results of the Partial International Search dated May 13, 2015 From the International Searching Authority Re. Application No. PCT/IL2015/050248.

International Preliminary Report on Patentability dated Aug. 4, 2016 From the International Preliminary Examining Authority Re. Application No. PCT/IL2015/050248.

International Search Report and the Written Opinion dated Jul. 28, 2015 From the International Searching Authority Re. Application No. PCT/IL2015/050248.

Invitation to Pay Additional Fees dated Mar. 3, 2016 From the International Preliminary Examining Authority Re. Application No. PCT/IL2015/050248.

Written Opinion dated May 4, 2016 From the International Preliminary Examining Authority Re. Application No. PCT/IL2015/050248.

* cited by examiner

FIG. 12

ACTIVE DRY POWDER INHALER

RELATED APPLICATIONS

This application is a National Phase of PCT Patent Application No. PCT/IL2015/050248 having International filing date of Mar. 10, 2015, which claims the benefit of priority under 35 USC § 119(e) of U.S. Provisional Patent Application No. 61/950,256 filed Mar. 10, 2014. The contents of which are incorporated herein by reference in their entirety.

FIELD AND BACKGROUND OF THE INVENTION

The present invention, in some embodiments thereof, relates to the field of dry powder delivery devices, and more particularly, to methods and systems for controlled delivery of dry powder.

Inhalation of therapeutic aerosols or dry powder medicaments are an effective method of drug delivery, frequently applied to treat respiratory disease. Three leading types of inhalers are commonly used today: metered dose inhalers, dry powder inhalers, and nebulizers.

In a Metered Dose Inhaler (MDI), a solution is stored in a pressurized canister that contains a propellant. The canister is mounted to a hand-operated actuator having a mouthpiece and optionally a chamber. The user exhales, and then places the mouthpiece or the chamber in the mouth, actuating the device to inhale a fixed dose of medication in aerosol form.

A Dry Powder Inhaler (DPI) inhaler delivers a medication in the form of a dry powder to the lungs. A measured quantity of medication is manually loaded into the inhaler prior to use, or pre-loaded inside the inhaler. The user inserts the inhaler mouthpiece into the mouth, takes a deep inhalation, and holds the breath for few seconds to allow the inhaled particles to settle onto the lung airways. Most DPI devices relay on the patient inhalation flow rate to transfer the powder from the device (as a gas suspension of solid particles), and to deagglomerate the powder into aerosol particles small enough to reach the lungs. An insufficient inhalation flow may result in an inadequate dose delivery and incomplete powder deagglomeration.

Nebulizers deliver drug in the form of aerosol. Compressed air is blasted through or near a liquid medicine to aerosolize it. The aerosol is then inhaled by the patient using a mouthpiece or a face mask. Some nebulizers use vibrating membranes instead of a compressor to produce the aerosol. Nebulizers are designed for a prolonged respiratory cycle drug delivery. While inhaling the aerosol medicaments, the user breathes in a normal rate for several minutes until the dose transfer is completed.

Dry powder inhalers as known in the art are exemplified in the following publications:

A U.S. Patent Application Publication No. 2004/0089299, to Bonney et al., entitled "Inhaler".

A U.S. Pat. No. 6,012,454 to Hodson et al., and entitled "Dry Powder Inhalation Device".

A U.S. Patent Application Publication No. 2007/272763 to Dunne et al., and entitled "Dispensing Device, Storage Device and Method for Dispensing Powder".

A U.S. Patent Application Publication No. 2005/263151 to Hochrainer et al., and entitled "Powder Inhaler Having a Nozzle with a Plurality of Channels".

A U.S. Patent Application Publication No. 2001/029948 to Ingle et al., and entitled "Systems and Methods for Extracting Powders from Receptacles".

A U.S. Patent Application Publication No. 2005/087189 to Crockford et al., and entitled "Drug Delivery Apparatus".

A U.S. Patent Application Publication No. 2008/035143 to Sievers et al., and entitled "Human-Powered Dry Powder Inhaler and Dry Powder Inhaler Compositions".

An International Patent Application Publication No. WO2002/005879 to Brand et al., and entitled "Medicament Dispenser".

An International Patent Application Publication No. WO2011/077414 to Kaufmann et al., and entitled "Dry Powder Delivery Device and Method".

Additional background art includes: U.S. Pat. No. 7,819,116; U.S. Pat. No. 7,520,278; U.S. Pat. No. 7,458,373; U.S. Pat. No. 7,322,355; U.S. Pat. No. 7,117,867; U.S. Patent Application Publication No. 2009/0095294; U.S. Patent Application Publication No. 2005/0056276; U.S. Patent Application Publication No. 2004/0079368; and U.S. Patent Application Publication No. 2003/0168057.

Also comprising background art are German Patent Publication No. 19502725 A1, relating to a pump dispenser unit for delivering a medium carried in a fluid from a holding zone; and U.S. Patent Application Publication No. 2011/0220106 A1, relating to a medication inhaler for concurrently delivering multiple doses of medications, including a medication delivery needle which penetrates the medication containers when the inhaler is actuated.

SUMMARY OF THE INVENTION

According to an aspect of some embodiments of the present invention, there is provided an inhaler for delivering dry powder medicament contained in a capsule, the inhaler comprising: a capsule chamber sized to fittingly hold the capsule within a capsule-holding volume; and at least one needle; wherein the needle moves along a path to introduce a portion of the needle across a first boundary location of the capsule-holding volume, and into an interior of the capsule-holding volume; and wherein the needle moves further along the path to move the portion of the needle from the interior to a second boundary location of the capsule-holding volume.

According to some embodiments of the invention, when the capsule is placed within the capsule-holding volume, the moving further along the path forces the portion of the needle against a wall of the capsule from within the interior to form a capsule outlet for the dry powder medicament.

According to some embodiments of the invention, no more than 20% of the wall of the capsule displaced to form the capsule outlet is within the capsule interior after formation of the capsule outlet.

According to some embodiments of the invention, the shape and size of the capsule outlet is determined by the cross-section of the needle.

According to some embodiments of the invention, the needle comprises cross-sections of at least two different sizes.

According to some embodiments of the invention, the two different cross-sections occur on a respective at least two longitudinal sections, each having a different cross-section therealong.

According to some embodiments of the invention, the portion of the needle moves past the second boundary location to exit the capsule-holding volume.

According to some embodiments of the invention, the portion of the needle retracts into the interior after reaching the second boundary location.

According to some embodiments of the invention, a tip of the needle portion comprises a sharpened conical section.

According to some embodiments of the invention, the needle comprises a lumen having a gas inlet and a gas outlet; and the outlet moves into the capsule-holding volume when the needle moves along the path into the interior.

According to some embodiments of the invention, the inhaler comprises a compressed gas source and a delivery system for gas from the compressed gas source to the lumen of the needle.

According to some embodiments of the invention, the inhaler comprises at least two spatially separated the gas outlets.

According to some embodiments of the invention, the inhaler comprises at least one valve for separately controlling gas delivery via each of the gas outlets.

According to some embodiments of the invention, the needle moves to position the gas outlet in at least two positions within the capsule-holding volume from which gas is delivered into the capsule-holding volume.

According to some embodiments of the invention, the inhaler further comprises a controller functionally connected with the gas delivery system for controlling delivery of compressed gas to the gas outlet.

According to some embodiments of the invention, the inhaler further comprises a flow sensor functionally connected with the controller; the controller determining breathing parameters of a user of the inhaler according to flow rate measurements of the flow sensor; the controller controlling the delivery of the compressed gas into the capsule, and thereby controlling delivery of the medicament dry powder to the user of the inhaler, in accordance with the determined breathing parameters.

According to some embodiments of the invention, the breathing parameters are selected from the list consisting of: inspiratory flow rate; inspiratory volume; inspiratory phase; expiratory flow rate; expiratory volume; expiratory phase; and breath pattern.

According to some embodiments of the invention, the inhaler further comprises a feedback interface coupled with the controller, the controller providing breathing guidance to the user, via the feedback interface.

According to some embodiments of the invention, the feedback interface operates to provide user breathing guidance, prior to the needle moving along the path.

According to some embodiments of the invention, the inhaler can deliver more than a single dry powder medicament simultaneously.

According to some embodiments of the invention, the capsule chamber fittingly receives a group of physically linked capsules, forming together a continuous chain of powder compartments.

According to an aspect of some embodiments of the present invention, there is provided a detachable module fittable to an inhaler for delivering dry powder medicament contained in a capsule, the module comprising: a capsule chamber sized to fittingly hold the capsule within a capsule-holding volume; and at least one needle; wherein the needle moves along a path to introduce a portion of the needle across a first boundary location of the capsule-holding volume, and into an interior of the capsule-holding volume; and wherein the needle moves further along the path to move the portion of the needle from the interior to a second boundary location of the capsule-holding volume.

According to an aspect of some embodiments of the present invention, there is provided a kit comprising the module, and at least ten capsules containing dry powder medicament.

According to an aspect of some embodiments of the present invention, there is provided an inhaler for delivering dry powder medicament contained in a capsule, the inhaler comprising: a capsule chamber sized to fittingly hold the capsule within a capsule-holding volume; and at least one needle comprising a gas lumen having at least one gas outlet which moves into the capsule-holding volume, and from which gas is introduced into the capsule-holding volume.

According to some embodiments of the invention, the at least one gas outlet comprises at least two spatially separated gas outlets.

According to some embodiments of the invention, the inhaler comprises at least one valve for separately controlling gas delivery via each of the at least two spatially separated gas outlets.

According to some embodiments of the invention, the needle is movable within the capsule-holding volume so that the at least one gas outlet releases gas from at least two positions within the capsule-holding volume.

According to some embodiments of the invention, the inhaler produces a plurality of gas flow regimes within the capsule from the at least one gas outlet by separately controlling the gas flow from each outlet.

According to some embodiments of the invention, at least one of the plurality of flow regimes comprises a vortex which substantially fills the interior of the capsule with gas rotating in a first rotational direction.

According to some embodiments of the invention, at least one of the plurality of flow regimes comprises gas flowing in a plurality of rotational directions.

According to some embodiments of the invention, at least one of the plurality of flow regimes comprises a vortex which substantially fills the interior of the capsule with gas rotating in a second rotational direction.

According to an aspect of some embodiments of the present invention, there is provided a detachable module fittable to an inhaler for delivering dry powder medicament contained in a capsule, the module comprising: a capsule chamber sized to fittingly hold the capsule within a capsule-holding volume; and at least one needle comprising a gas lumen having at least one gas outlet which moves into the capsule-holding volume, and from which gas is introduced into the capsule-holding volume.

According to an aspect of some embodiments of the present invention, there is provided a kit comprising the module, and at least ten capsules containing dry powder medicament.

According to an aspect of some embodiments of the present invention, there is provided a method of preparing an inhaler capsule containing dry powder medicament with a capsule outlet for the medicament, the method comprising: introducing a needle into an interior of the capsule; and puncturing a wall of the inhaler capsule by forcing the needle against the wall from the capsule interior to define the capsule outlet.

According to some embodiments of the invention, no more than 20% of the wall of the capsule displaced to form the capsule outlet is within the capsule interior after formation of the capsule outlet.

According to some embodiments of the invention, the method comprises moving the needle to de-obstruct the capsule outlet.

According to some embodiments of the invention, forcing the needle against the wall comprises piercing the wall with the needle.

According to an aspect of some embodiments of the present invention, there is provided a method of dispersing medicament from an inhaler capsule containing dry powder medicament, the method comprising: directing compressed gas into the capsule from at least one element having a gas outlet positioned within the capsule.

According to some embodiments of the invention, the gas is directed from at least two separate gas outlet positions within the capsule.

According to some embodiments of the invention, the flow of gas is separately controlled for each of the at least two separate gas outlet positions.

According to an aspect of some embodiments of the present invention, there is provided a method of expelling a dry powder medicament from an inhaler capsule, comprising: blowing gas through at least two gas outlets positioned within an interior volume of the inhaler capsule.

According to some embodiments of the invention, delivery of the blown gas to the at least two outlets is separately controlled for each outlet.

According to some embodiments of the invention, the method comprises allowing the gas and suspended dry powder medicament to leave the inhaler capsule through an outlet of the capsule.

According to an aspect of some embodiments of the present invention, there is provided a method for actively delivering dry powder medicament contained in a capsule, the method comprising: introducing a needle having a gas outlet into an interior of the capsule; puncturing a wall of the capsule by forcing the needle against the wall from the capsule interior to define the capsule outlet; positioning the gas outlet of the needle within the capsule; directing compressed gas into the capsule from the gas outlet of the needle.

According to some embodiments of the invention, the compressed gas is delivered from outlets in at least two different positions within the capsule in at least two flow regimes, and the capsule outlet is positioned so that the particles exiting the capsule outlet in a first flow regime are selected by the position of the capsule outlet to be of a different size or density than particles exiting the capsule outlet in a second flow regime.

According to some embodiments of the invention, the compressed gas is delivered from outlets in at least two flow regimes, and the capsule outlet size is increased between the two flow regimes.

According to some embodiments of the invention, the outlet size is increased by forcing the needle further into the capsule outlet than during the initial formation of the capsule outlet.

According to an aspect of some embodiments of the invention, there is provided a detachable module fittable to an inhaler for delivering dry powder medicament contained in a capsule, the module comprising a powder flow airway; wherein the powder flow airway is connectable to be in fluid communication with an airway of a base section of the inhaler; and wherein the powder flow airway comprises regions of the inhaler through which powder flows upon administration of the dry powder medicament.

According to an aspect of some embodiments of the invention, there is provided an inhaler for use with a detachable module fittable to an inhaler for delivering dry powder medicament contained in a capsule, comprising a gas flow airway connectable to be in fluid communication with a powder flow airway of a module through which medicament powder flows when the dry powder medicament is administered.

According to some embodiments of the invention, the inhaler comprises a controller functionally connected to at least one from among the group consisting of a pressurized gas source, a gas flow sensor, and a valve.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 12 shows an exemplary logged data summary sheet for an inhaler, according to some exemplary embodiments of the invention;

DESCRIPTION OF SPECIFIC EMBODIMENTS OF THE INVENTION

Figure 1A:
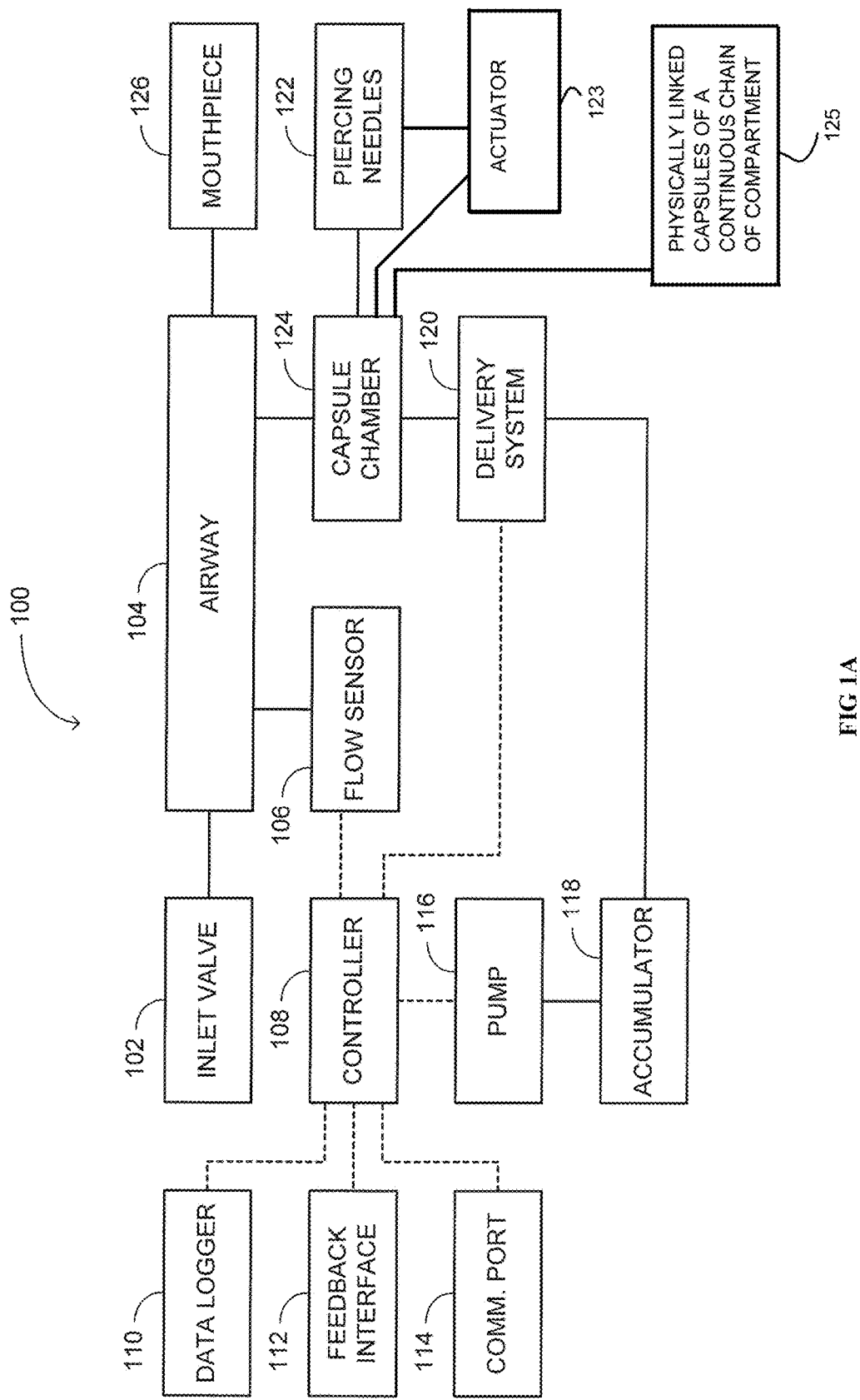
FIG. 1A schematically illustrates a block diagram of the components of a portable active inhaler, according to some exemplary embodiments of the invention.

The present invention, in some embodiments thereof, relates to the field of dry powder delivery devices, and more particularly, to methods and systems for controlled delivery of dry powder.

Overview

A broad aspect of some embodiments of the current invention relates to an inhaler for extracting dry powder medicament out of a capsule, and for delivering the medicament to a patient. In some embodiments, the inhaler includes a compressed gas source, at least one gas delivery lumen, at least one valve, at least one piercing needle, and at least one capsule chamber. The capsule chamber receives and holds a capsule containing dry powder medicament.

In some embodiments, the piercing needle and/or the capsule chamber are movable with respect to each other (e.g., the capsule chamber is movable with respect to the needles, and/or vice versa). Optionally, the gas delivery lumen runs along (for example, axially within) the piercing needle. The valve regulates flow of compressed gas through the gas delivery lumen. In some embodiments, the gas lumen moreover includes at least one outlet for delivering gas into the capsule. In some embodiments, gas is delivered into the capsule from a pressurizing source (active device). In some embodiments, gas is delivered into the capsule by capturing a portion of the pressure differential developed by patient inhalation (for example, patient inhalation creates a pressure differential across a capsule, inducing flow through a needle penetrating the capsule and out of an outlet of the capsule).

An aspect of some embodiments of the invention relates to determination of the flow of gas within a capsule used to release, disperse, and/or deagglomerate a dry powder medicament. In some embodiments, a gas flow regime is administered within the capsule, wherein parameters of the flow regime relate to flow characteristics; for example: flow direction, gas velocity, trajectory, pressure, flow rate, and/or flow scheme (laminar or turbulent).

In some embodiments, a regime of gas flow is chosen to reduce or remove the incidence of flow dead zones. For example, a chaotic and/or variable flow (such as flow from two or more separate flow regimes) is generated to help ensure that all regions of the capsule interior are swept by gas current. In some embodiments, a regime of gas flow is chosen to create a preferred condition of separation. For example, a "centrifuging vortex" is optionally provided for all or part of a period of gas flow. Optionally, conditions are chosen (by location of the aperture relative to the capsule environment, and/or by restriction of shear forces/turbulence, for example) so that large particles (for example) are preferentially kept away from an exit aperture of the capsule, while smaller particles are allowed to exit. This differentiation is created, for example, by centrifuging action of a flow vortex, and/or by pulsed delivery of gas where there is a lag (of, for example, 10 msec, 50 msec, 100 msec, 200 msec, 500 msec, or another larger, smaller, or intermediate value) between relatively energetic gas injection (of, for example, 1 l/min, 0.5 l/min, 0.25 l/min, or another larger, smaller or intermediate flow rate) to a capsule (for deagglomeration), and a less energetic period of decompression (from an initially elevated pressure within the capsule due to pressurizing during gas injection) through a capsule aperture (leading to dispersal). In some embodiments, there is switching between regimes suited to different functions. For example, an early regime is chosen to maximize deagglomeration and/or small particle dispersal (optionally, flow energy is increased for a particular flow volume; for example, multiple short bursts of high pressure gas are delivered rather than a lower pressure of more continuous gas delivery). In some embodiments, the burst duty cycle is about 50%. In some embodiments, the burst duty cycle is about 10%, 25%, 66%, 90%, 100%, or another smaller or intermediate duty cycle.

In some embodiments, a later regime is chosen to maximize clearing of the capsule contents (for example, variation of flow direction and/or spatial source is increased, and/or capsule outlet aperture size is increased). In some embodiments, switching between regimes is used to ensure clearing of residual powder: for example, a first flow regime is provided, and then a second (optionally a second and further) flow regime sweeps out regions of residual powder left by the first regime.

Optionally, gas flow regimes are produced by directing the compressed gas into the capsule from at least two spatially separated capsule gas inlets (alternatively described as needle or lumen outlets). Optionally, gas leaving the separated needle outlets is also separately controlled. Control comprises, for example, opening or closing (fully or partially) a valve gating one or more inlets, and/or regulation of a pressure differential which draws gas out of the needle outlet. For example, the gas can be directed through different gas lumens, different gas outlets of the same gas lumen, and/or a gas outlet can be moved for producing different gas flow regimes. Thus, different locations of needle outlets, and/or different combination of outlet locations, produce different gas flow regimes. Optionally, the gas flow regimes are modified by the shape of the gas outlets (e.g., a circular gas outlet or a slit-shaped outlet), the size of the outlets, and/or other outlet characteristics such as lumen diameter. For example, in some embodiments, a needle lumen is about 1.0 mm in diameter. Optionally, the needle lumen diameter is about 0.5 mm, 0.75 mm, 1.25 mm, 1.5 mm, 2 mm, 2.5 mm, or another larger, smaller, or intermediate diameter. In some embodiments, the lumen outlet diameter is, for example, about 0.5 mm. Optionally, the lumen outlet diameter is, for example, about 0.1 mm, 0.25 mm, 0.5 mm, 0.75 mm, 1.5 mm, or another larger, smaller, or intermediate diameter. Optionally, apertures of more than one size are used (for example, a greater flow is modulated by a smaller flow, the ratio of the two flows being set at least in part by the aperture ratio of 2:1, 3:1, 4:1, or another greater, smaller, or intermediate ratio).

In some embodiments, the gas flow regimes are varied by regulating the gas flow rate via the gas outlets. For example, the gas is delivered continuously or in bursts (which duration and/or frequency are regulated), the gas can be delivered at different rates, pressures, velocities and/or amounts.

Thus, by controlling the gas flow via the gas outlets, the outlet location, the outlet size and/or shape, and/or the compressed gas pressure, the gas flow regimes are further varied.

An aspect of some embodiments of the current invention relates to the directing of compressed gas into the capsule from spatially different locations within the capsule. Spatially different locations are, for example, locations in which the same aperture is moved (translated or rotated, for example) over time, and/or two or more apertures are provided. Spatially different locations are optionally distinguished, by axial position. For example: one location is more axially centered than another. Potentially, this affects the tendency and/or character of vortex flow within the capsule. In some embodiments, spatially different locations are distinguished by position relative to a capsule outlet (dispersal outlet). Potentially, a needle outlet into the capsule which is closer to a capsule outlet causes less initial dispersion of powder (for example, due to powder left "behind" it), than an outlet which is positioned more distantly from the capsule outlet. In some embodiments, compressed gas is directed into the capsule from at least two spatially separated gas outlets. Optionally, gas flow via the gas outlets is separately regulated. In some embodiments, flow from a single outlet is varied over time by transitions of flow rate and/or outlet position. Optionally, the inhaler induces various gas flow regimes within the capsule, and switches between regimes. Potentially, application of turbulent and/or variable gas flow regimes and/or the combinations thereof reduce the amount of powder remaining trapped within the capsule, improve deagglomeration, and/or efficiently mix the powder particles. Optionally, the gas flow regimes and/or the combinations thereof are modified for different capsules, different powders and/or carriers, combinations of powders, different doses, patient characteristics (e.g., anatomy and/or breathing pattern), and/or different delivery patterns.

In some embodiments, the inhaler comprises a base section and a replaceable module which comprises functions and/or structures relating to the positioning of gas outlets in a capsule: for example, at least one needle comprising a flow lumen and flow outlet; a capsule chamber for containing the capsule, and/or mechanical and/or electrical means of placing the needle.

An aspect of some embodiments of the current invention relates to the preparation of a capsule so that it is suited to proper release of its contents (including effects on dispersal and/or deagglomeration) upon the introduction of gas flow therewithin.

In some embodiments, relative movement of the needle and capsule chamber during operation introduces a tip of the needle into a capsule. For example, this is by piercing a capsule inlet in a wall of a capsule held in the capsule chamber, punching a portion of the wall from the capsule, and/or otherwise using a member positioned within the capsule to create an aperture in the capsule wall. The piercing end (and/or end otherwise involved in capsule puncture) of the needle is then brought to form a capsule outlet at a wall of the capsule from within the capsule. For example, the needle is passed first into a proximal wall of the capsule, then out again at a wall distal to the initial piercing. Additionally or alternatively, the piercing portion of the needle changes direction during piercing; for example, the needle and/or its path is curved to penetrate and/or form apertures at adjacent wall portions.

In some embodiments, the inhaler comprises a base section and a replaceable module which comprises functions and/or structures relating to the formation of outlets in a capsule: for example, at least one needle comprising a sharpened or otherwise prepared tip for capsule puncturing; a capsule chamber for containing the capsule, and/or mechanical and/or electrical means of moving the needle.

This piercing of the capsule outlets from within the capsule and outwardly is referred to hereinbelow as intracapsule piercing or outward piercing. Potentially, the outwardly extending flare (or other wall portion) of the capsule outlet reduces the amount of powder trapped in the capsule, and/or avoids formation of internal irregularities which could decrease the reproducibility of powder release and/or deagglomeration. The amount of wall portion left inside the capsule after capsule outlet formation is, for example, 0%, less than 5%, less than 10%, less than 20%, or less than another greater, lesser, or intermediate number. Potentially, more accurate prior determination of powder release and/or deagglomeration properties of an inhaler/capsule system is enabled by removing difficult to model and/or non-reproducibly formed irregularities from the capsule interior.

The effectiveness of dry powder medicament administration by dry powder inhalers is considered to be affected by numerous parameters beyond the simple amount of the active pharmaceutical ingredient (API) provided in a capsule. For example, small particles potentially reach deeper into the lungs, while large particles tend to deposit more superficially. However, even providing suitably smaller or larger particles during dose manufacture is potentially insufficient to achieve the desired dosing performance, since particles can also interact with each other and/or the capsule that contains them—they may clump or stick. Additionally or alternatively, carrier materials (such as lactose) are typically used, to provide desired medicament properties; for example, properties that assist in the manufacturability of a medicament. However, it may be further preferred that the carrier/API complex disassociate for dose delivery to a patient. Thus, an inhaler device is not only an administration device; it also performs aspects of last-stage processing of the medicament before delivery.

It is a potential advantage to open a capsule with a relatively small needle piercing, as this potentially allows the capsule to act for a longer period as a processing chamber for the powder which is to be administered. Potentially, it is an advantage to add high mechanical energy to the medicament powder while it is at its highest concentration, to promote a greater number of deagglomeration interactions (collisions). Additionally or alternatively, using an increased ratio of particle-particle interactions for deagglomeration is potentially preferred relative to the number of particle-wall interactions, to reduce loss of API along the inhaler flow path. Moreover, it is a potential advantage to concentrate wall/particle interactions that do occur over a relatively confined wall area, for example to decrease loss of API and/or to increase the chances of re-suspension of particles that do stick by subsequent collisions.

In some embodiments, a needle which pierces a capsule to provide an outlet is removed from the piercing, leaving an open hole in the capsule wall allowing the dispersal of medicament therethrough. In some embodiments, a portion of the piercing needle comprises a lumen with apertures locatable both inside and outside the capsule, allowing the needle to be positioned as a passageway for the dispersal of medicament from the capsule. This is a potential advantage, for example, to allow apertures to be provided which capture and then outwardly channel medicament from one or more locations within the volume of the capsule interior.

However, a potential advantage of using the pierced wall of the capsule directly to form an aperture is reduced concern that a needle passage will plug, particularly a needle which is to be used for the administration of a plurality of dosages.

An aspect of some embodiments of the current invention relates to the coordinated creation of medicament flow outlet apertures and positioning of gas inlet apertures, to create a flow regime having properties which are controlled based on the relative features of gas inlets and medicament flow outputs. For example, flow is optimized for a particular ratio of rate of dispersal from the capsule to generation of disaggregating collisions within the capsule, based on the flow regime and the gas inlet characteristics chosen.

In some embodiments, for example, a medicament flow outlet is positioned near the axis of the capsule, and a first (single-vortex, for example) flow regime is selected to rotate the medicament helically within the capsule. Potentially, the vortex flow of gas at least partially stratifies particles within the capsule, such that gas-borne particles reaching the medicament flow outlet are enriched in particles of a particular range of sizes, densities, and/or shapes. Optionally, a second flow regime interrupts this stratification, so that another distribution profile of particles reaches and exits the medicament flow outlet. In some embodiments, the relative representation of size profiles of particles dispersed vs. particles in the capsule, in a particular flow regime, and for particles having at least a factor of 2 difference in size, is changed, for example, by at least 10%, 20%, 50%, 75%, or by another greater, lesser, or intermediate percentage. In some embodiments, the in-capsule/dispersed from capsule difference is changed in another particular flow regime by 25%, 50%, 75%, 100%, or another greater, lesser, or intermediate value.

In some embodiments, characteristics of a gas flow regime are altered by changing the size, position and/or number of flow outlets in a capsule. For example, a medicament flow outlet is initially created small (for example, 0.5 mm in diameter), potentially increasing the average period of time during which a particle experiences high-energy (deagglomerating) conditions before being expelled from the capsule. After a first period of dispersal, the outlet configuration of the capsule is changed, in some embodiments, for example by puncturing or otherwise adding more outlets (1, 2, 3 or more capsule outlets, for example), increasing the size of an existing aperture (for example, by a diameter change of 25%, 50%, 100%, or another larger smaller or intermediate change), tearing wall material near the aperture, or otherwise modifying the capsule wall. Upon administration of a further gas flow regime, there is potentially a different profile of powder release; for example; with respect to distribution of particle sizes, and/or release efficiency.

An aspect of some embodiments of the invention relates to providing an inhaler with a removable (replaceable and/or disposable) module (a "head", but optionally a module of another type such as a cartridge) for use with a base. A potential advantage of this configuration is to allow a more expensive base system to be separated from components liable to contamination (with medicament powder, patient secretions, and/or moisture, for example). In some embodiments, the removable module comprises regions of the inhaler device which are liable to contact and/or contain powder. Such regions optionally comprise, for example, a capsule chamber, means for opening a capsule such as needles/blades, and/or portions of the device through which powder blows. In some embodiments, the removable module comprises regions of the inhaler designed for patient contact, for example, a mouthpiece or mask.

In some embodiments, a removable module comprises identifying information which relays identifying information about the module to the base. Potentially, this allows a base to be set up to reject operation with modules having the same mating parts, but carrying a different dosage. Additionally or alternatively, this allows a base to be set up to work with multiple dosage regimes—for example delivering different regimes of dispersal/deagglomeration gas, imposing different discharge threshold requirements, different status signaling, or another difference according to the preferred operating conditions for the identified module.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Overview of Inhaler Components and Use

Components of an Exemplary Inhaler

Reference is now made to FIG. 1A, which is a schematic illustration of a block diagram of the components of a portable active inhaler 100, according to some exemplary embodiments of the invention.

Before discussion of particular aspects of some embodiments of the invention, a brief introduction to elements of an exemplary inhaler 100 is provided.

In some embodiments of the invention, inhaler 100 includes an airway 104, a gas delivery system 120, piercing needles 122, and at least one capsule chamber 124. Medicament is delivered through a mouthpiece 126, or optionally through a face mask or nasal adapter. In some embodiments, gas is pressurized by a pump 116 into an accumulator 118. Optionally, another source of pressurized gas is used.

Apart from the gas pathway subsystem, some embodiments of the current invention include means for sensing, control, monitoring and/or feedback. In some embodiments, the inhaler 100 further comprises a flow sensor 106, a controller 108, a data logger 110, a feedback interface 112, and/or a communication port 114.

Optionally, in embodiments where appropriate corresponding elements are provided, various elements are in fluid connection with one another. For example: an inlet valve 102 and/or inlet restriction is provided in fluid connection with airway 104; airway 104 is further in fluid connection with each of flow sensor 106, capsule chamber 124 and/or mouthpiece 126; pump 116 is in fluid connection with accumulator 118; accumulator 118 is in fluid connection with gas delivery system 120; delivery system 120 is in fluid connection with capsule chamber 124; and/or capsule chamber 124 is in fluid connection with mouthpiece 126 via airway 104. Control coupling includes, for example: controller 108 coupled with flow sensor 106, data logger 110, feedback interface 112, communication port 114, pump 116, and/or with gas delivery system 120, for controlling the operation thereof.

Airway 104 is a fluid passageway that allows passage of fluids to and from mouthpiece 126. Optionally, valve 102 determines the restriction of flow through airway 104, and/or restriction is determined by the form of the airway 104 itself (for example, a form including a restriction in the cross-section of the airway). It is noted that the airway restriction potentially affects drug deposition. Optionally, inlet valve 102 is a one way valve (i.e., a check valve) that also prevents exhaling into inhaler 100.

In some embodiments, inhaler 100 is a portable hand held inhaler as can be seen, for example, in relation to inhalers 200 and 400 of FIGS. 2 and 4A-4F, respectively.

In some embodiments, the inhaler is a self-powered inhaler including an internal power source, such as a battery for providing power to the various components of the inhaler, such as the controller 180, the flow sensor 106, the gas source 116, 118, and/or the gas delivery system 120. Alternatively, the inhaler can be coupled with an external power source, either for recharging an internal battery or for directly powering the inhaler.

Exemplary Stages of Inhaler Use

In some embodiments of the invention, use begins with the user loading a dry powder medicament capsule into capsule chamber 124. Optionally, a group of physically linked capsules 125 may be fittingly received within capsule chamber. The user arms and sets up inhaler 100, preferably in a single maneuver (e.g., by rotating a priming knob), as also described hereinbelow with reference to FIGS. 4A-4F. The arming and setting up maneuver includes all or part of the following actions:

Optionally, pump 116 pumps gas into accumulator 118, and/or another pressure source is optionally otherwise prepared and/or verified for use. Alternatively, accumulator priming is postponed until powder delivery.

In some embodiments, capsule chamber 124 is moved toward needles 122 such that needles 122 pierce capsule inlets in the proximal wall of the capsule. Optionally, the needles are moved toward the capsule chamber.

Capsule chamber 124 and needles 122 are further moved such that needles 122 penetrate into the capsule via the pierced inlets and pierce capsule outlets from within the capsule.

Following piercing of the capsule outlets, the needles optionally retract to position the gas outlets of the gas lumens in the needles within the capsule for delivering the compressed gas into the capsule.

Use, in some embodiments, continues with the patient bringing mouthpiece 126 to the mouth and taking a deep breath. In some embodiments, when the inspiratory flow rate exceeds a threshold, controller 108 opens the valves of delivery system 120 for delivering the compressed gas into the pierced capsule, which is optionally accompanied by activation of pump 116. Delivery of compressed gas deagglomerates, disperses, mixes, and releases the dry powder medicament toward the patient. Alternatively, in case of employing a face mask instead of a mouthpiece, the patient attaches the face mask to the face and breathes in and out through the face mask, so that flow sensor 106 can acquire flow readings. Controller 108 optionally calculates breathing parameters of the patient, and provides breathing feedback to the patient via feedback interface 112 (e.g., by blinking a LED, and/or by an audio beep) that inhaler 100 is ready for action.

In some embodiments, a facemask or nasal adapter is used. Optionally, such interfaces are used with a prolonged (multiple inhalation) delivery paradigm. In a multiple inhalation paradigm, each time the sensor detects patient inhalation, a portion of the capsule drug content is dispersed. For example a system is optionally set to deliver a fixed burst of medicament laden air over a number of inspirations (for example, 5, 10, 20, or another greater, larger, or intermediate number of inspirations). Optionally, a feedback interface (such as a LED illumination and/or sound indication) indicates dug delivery status, for example as described in relation to FIGS. 10A-10C hereinbelow. Delivery repeats at appropriate inhalation points until the capsule is empty. In some embodiments, the device controller tracks how much drug is dispersed over time and/or delivery cycles, allowing determination of the empty capsule condition). Optionally, when the capsule is empty the feedback interface indicates complete delivery. Optionally, the portion of the dose that is delivered per respiration, and/or the phase of the respiration is the same or different for each inhalation, according to the settings of the controller. A potential advantage of dividing a dose this way is to increase the reliability of dose delivery. Additionally or alternatively, it allows making individual deliveries smaller, and/or to allow a larger powder load (likely to trigger a reflex cough, for example, if delivered all at once) to be divided among multiple inhalation cycles.

Controller 108 controls the valves of delivery system 120 for delivering the compressed gas into the capsule, and for releasing thereby the dry powder medicament toward the patient, in coordination with the breathing of the patient. It is noted however, that the inhaler optionally monitors the patient respiratory cycles and breathing parameters through the mouthpiece or through the nasal adapter, as well as through the facemask. Additionally, an inhaler with a mouthpiece or with a nasal adapter can also be employed for drug delivery over several breathing cycles.

In some embodiments, inhaler 100 coordinates and controls the delivery of the dry powder medicament according to a release condition. The release condition can be associated with, for example, the inspiratory phase, and/or an inspiratory flow rate threshold (described, for example, in relation to FIG. 5 hereinbelow), and/or with the expiratory phase and/or flow rate. Other release conditions can relate, for example, to the carbon dioxide content, the oxygen content, the moisture content, the pressure of the inspiratory phase, the blood glucose level and/or other blood content parameters. Still other release conditions relate to a secondary effect; for example, a side effect of the dry powder medicament. For example, morphine delivery to a patient is not released until blood pressure exceeds a threshold. Other release conditions relate to the time of day or to other measurements, such as the heart rate of the patient.

Additionally or alternatively, the release of the dry powder is controlled manually. In this manner, the user (e.g., the patient, a physician or a caretaker) triggers delivery, for example, by pressing a drug release button. The user optionally triggers drug delivery according to the readings of the flow sensor or according to other (or additional) sensors, such as a blood pressure sensor and/or glucose blood level sensor.

Active Gas Flow Regimes

In some embodiments, gas flow regimes are actively produced by the inhaler 100 within the capsule for preparing the dry powder for delivery (e.g., deagglomeration and dispersion), for extraction of the dry powder from its' capsule and for delivering the medicament to the patient. Optionally, gas flow regimes are adapted, for example: to the powder to be deagglomerated and dispersed, the carrier, the patient (e.g., anatomy and breathing), and/or the target region for the medicament.

In some embodiments, elements involved in determining the gas flow regime include the gas delivery system 120, piercing needles 122, capsule chamber 124, and the capsule itself (for example capsule 210, 300, and/or 420 of FIGS. 2, 3A-3G, and/or 4C-4E, respectively). Gas is sourced, for example, from a pump 116 and/or accumulator 118, or from another source of pressurized gas. Operation of the flow system is under the control of a controller 108, optionally modified based on inputs from one or more sensors such as flow sensor 106.

In some embodiments, compressed gas is delivered into the capsule via delivery system 120. Delivery system 120 delivers the compressed gas into the capsule for deagglomerating, aerosolizing, and/or releasing the dry powder medicament from the capsule. In some embodiments, the delivery is direct, for example, via at least one gas delivery aperture introduced to the interior of the capsule. Optionally, the delivery aperture is an aperture of needle 122. In some embodiments, system 120 enables inhaler 100 to produce a plurality of gas flow regimes within the capsule.

In some embodiments, flow is delivered to the capsule at a rate of about 1 liter per minute (1 l/min). In some embodiments, a peak rate of gas flow is, for example, about 10 l/min, for example, during release of pressure previously stored in an accumulator by a pump. In some embodiments, the maximum gas flow (such as during a valve opening with full pressure developed by the system's gas source) is, for example, about 0.1 l/min, 0.5 l/min, 1 l/min, 2 l/min, 5 l/min 10 l/min, 20 l/min, or another greater, lesser or intermediate flow rate. In some embodiments, the flow rate is continuously adjustable from no flow up to the maximum flow rate. In some embodiments, flow rate is adjustable in a number of steps. Control of flow rate comprises, for example, setting a valve opening time, a valve opening fraction, an inlet aperture size, an outlet aperture size, a gas source pressure, a gas source operating time, and/or another parameter.

In some embodiments, the maximum pressure developed by a pump is, for example, about 500 mmHg above gauge pressure. In some embodiments, the pressure developed is another number, for example, 50 mmHg, 100 mmHg, 200 mmHg, 400 mmHg, 800 mmHg, or another greater, lesser, or intermediate pressure.

Features, Parameters, and Uses of Active Gas Flow Regimes

Parameters of a gas flow regime include, for example: gas flow direction, gas velocity, gas trajectory, the amount of compressed gas directed into the capsule, the pressure at which the gas enters the capsule, the cycle of pressure experienced within the capsule, and/or parameters of pulsed or continuous flow. In some embodiments, one or more of these parameters is modified, for example, by delivering the gas via at least two separately controlled gas outlets, by controlling the gas pressure within the accumulator (or other delivery system pressure), by regulating flow of gas via the outlets, and/or by adapting the outlet shape, size, and/or position. The control of the gas flow within the capsule is elaborated on hereinbelow with reference to FIGS. 3A-3G.

In general, the inventors have found that removal of residual powder is significantly increased when at least two flow regimes are used to disperse powder, each administered from a at least one outlet having a different position and/or direction of flow than in the other regime. A two-needle system potentially accomplishes this without the need for additional motion of the system during ventilation (apart from that to independently drive the valves which gate the flow of gas). However, in some embodiments, a single needle is used, and the two-position condition is met by moving the needle (for example, advancing, retracting, and/or rotating the needle).

Dry powder inhalers use gas suspension to transfer dry powdered medicament to the target organ (typically the lungs). One method of packaging the medicament is within a capsule. Typically, an inhaler punctures the capsule to allow a flow of gas to reach the capsule contents. Active inhalers provide an active pressure source for achieving gas suspension. This provides a potential advantage over inhalation-driven powder dispersal by removing at least some variability in drug delivery due to patient performance. For example, Kaufmann et al. (WO2011/077414) describe a system which punctures the capsule to deliver gas flow directly to the capsule interior.

Conventional capsules can include various medicament dry powders with various active ingredients, and optionally include various inert carrier materials. The medicament powder (and the carrier) should sometimes be deagglomerated prior to delivery to the patient. Furthermore, different patients or different treated target sites may benefit from different levels of deagglomeration. For example, children may require more extensive deagglomeration (i.e., producing smaller powder particles) than adult patients. Medicament which is delivered to the upper regions of the breathing system may be less deagglomerated that medicament delivered to the deepest regions of the lungs. In case of delivering more than a single powder material (e.g., from different capsules, or from a single capsule), each medicament powder may be better deagglomerated by different gas flow regime or combination of regimes. Therefore, controlling the deagglomeration of the dry powder can improve the treatment.

In some embodiments of the present invention, appropriate control of gas flow (by one or more appropriately selected flow regimes) is used to reduce residual powder.

The dynamics of the gas flow used to suspend and/or transport a dry powder medicament can have an effect on the performance of the inhaler device. For example, some of the dry powder medicament, intended to be delivered to the patient, might be trapped within the capsule (this trapped powder which should have been delivered, is also referred to herein as residual powder). This reduces delivery efficacy (which can be defined as the amount of powder delivered divided by the amount of powder that should have been delivered according to the treatment plan). Furthermore, the amount of undelivered residual powder might change for different capsules, even similar capsules, and thus decreases dose uniformity. Thus, reduction of residual powder provides a potential advantage to ensure that the patient received the prescribed dose (and/or for monitoring the dose delivered to the patient), for maintaining dose uniformity, and/or for reducing medicament costs.

In some embodiments of the present invention, appropriate control of gas flow (by one or more appropriately selected flow regimes) is used to control deagglomeration.

API particles can have some tendency for self-adherence, which potentially changes transport and/or absorption properties of the ingredient. Additionally or alternatively, medicament is preferentially provided in a relatively coarse form for capsule manufacturing (for example, API attached to a carrier such as lactose), but preferentially delivered to the patient's respiratory tract in finer form (for example, with API separated from the carrier).

Examples of Active Gas Flow Regimes

The following describe other exemplary embodiments of the invention for which flow regime adaptability provides a potential benefit:

In some embodiments, a flow regime is configured to provide bursts which accommodate a breathing pattern of a patient. For example, a patient who is capable of deep inspirations is provided with an inhaler that gives a prolonged series of flow bursts (several hundred milliseconds up to several seconds, for example), allowing administration of the contents of a medicament capsule within substantially a single breath. Alternatively, a patient is provided with a brief burst during each of a series of inspirations (typically spaced over several seconds and up to a minute or two), allowing drug delivery to a patient without a requirement for the patient to alter their normal breathing pattern.

In some embodiments, a combination of different flow regimes is employed for improving extraction of the dry powder medicament from the capsule and significantly reducing the residual powder. Potentially, the use of different flow regimes helps to avoid a situation where powder accumulates in a particular region of the capsule, and/or a particular size of medicament particle is retained within the capsule.

In some embodiments, a first medicament powder (or mixture of powders) is deagglomerated better by a first gas flow regime, and a second medicament powder is deagglomerated better by a second gas flow regime. For example, a formulation that is based on API and lactose carrier is dispersed under a flow regime that efficiently separates between the API and the carrier; a formulation that contains only active ingredients (e.g. proteins) and no carrier particles is dispersed under a different flow regime that optimally deagglomerates the specific powder.

In some embodiments, there are several powders, and different gas flow regimes aid in mixing of the powders.

In some embodiments, different flow regimes are used to enable desirable drug delivery for different drug doses or different patient inhalation patterns (e.g. tidal breathing or single deep inhalation).

In some embodiments, different regimes are employed for deagglomerating the dry powder for producing different average particle sizes (e.g., a first combination of regimes for producing a first average particle size, and a second combination of regimes for producing a second average particle size). Optionally, for delivering the drug to the upper regions of the respiratory system of the patient, the drug is deagglomerated to relatively large particles as produced by a first gas flow regime. Optionally, for delivering the drug to the deepest regions of patient's lungs, the drug is deagglomerated to relatively small particles produced by a second or further gas flow regime.

In some embodiments, a first gas flow regime is selected to deagglomerate particles, optionally at the expense of efficiently expelling them from the capsule. For example, a gas escape aperture is placed where particle concentrations are low in the first flow regime. Potentially, deagglomeration takes place more efficiently within the capsule where particles are concentrated, and mechanical energy delivery is focused. After the deagglomeration regime, a second regime is used to help ensure particles are expelled, so that little or no medicament is left in the capsule.

In some embodiments, a flow regime is selected to preferentially expel medicament during a particular phase of the respiratory cycle; for example, to target deeper or upper respiratory tissues. Additionally or alternatively, the flow regime is adapted to even the rate of medicament expulsion. For example, flow turbulence is increased (optionally while flow remains about the same) as the amount of remaining medication decreases. Optionally, the increase is synchronized with respiratory phase. Potentially, this helps to even out the distribution of medicament through the respiratory tract.

Plurality of Gas Delivery Apertures for Dispersal and Deagglomeration

In some embodiments, delivery system 120 delivers the compressed gas from at least two spatially separated locations within the capsule. For example, the delivery system includes at least two outlets (optionally, outlets of one or more needles 120) for directing the compressed gas into the capsule. Additionally or alternatively, the delivery system includes an outlet which can be moved within the capsule (for example, advanced, retracted, and/or rotated) for producing different gas flow regimes.

In some exemplary embodiments of the invention, delivery system 120 includes two gas lumens. Each lumen includes at least one gas outlet (e.g., a side hole in the gas lumen). In operation, each lumen penetrates the capsule to position the gas outlet thereof within the capsule. The gas outlets of the gas lumens are thus located at spatially separated locations within the capsule.

Optionally, each gas lumen is associated with a respective gas valve (and/or other pressure control means) to regulate the compressed gas flow therethrough. Thereby, the gas is delivered from two spatially separated locations (i.e., the locations of the gas outlets), which are also separately controlled.

In this manner, a plurality of gas flow regimes can be produced within the capsule, for example, as described hereinbelow with reference to FIGS. 3A-3G. Examples include: a first gas flow regime in which a first lumen delivers gas, and a second lumen is shut; a second regime in which the first lumen is shut, and the second lumen delivers gas; and a third regime in which both lumens deliver compressed gas into the capsule simultaneously. As mentioned above, by employing a plurality of gas flow regimes the amount of residual powder is potentially decreased. For example, a powder particle which is trapped inside the capsule and is not released when gas flows according to the first gas regime, might be released by the second or the third regimes.

In some embodiments, each valve of each gas lumen is operable to select from among a plurality of flow levels (e.g., a valve can have flow levels of fully open and partially open, in addition to shut). Thereby, inhaler 100 can produce additional gas flow regimes within the capsule; for example: a first regime in which the first valve is fully open and the second valve is partially open, a second regime in which the first valve is fully open and the second valve is shut, a third regime in which the first valve is partially open and the second valve is fully open, a fourth regime in which the first valve is shut and the second valve is fully open, and/or other regimes according to other combinations available from the settings of the valve or valves.

In the example set forth in FIG. 2, hereinbelow, a single gas source is coupled to two lumens via two respective valves. However, it is noted that for producing a plurality of gas flow regimes, embodiments of the delivery system optionally include different number of gas lumens, each lumen optionally includes different number of gas outlets, and/or outlets are optionally of different shape and size. Embodiments of delivery system 120 optionally include different numbers of valves, each valve optionally regulates fluid flow in a different number of lumens, and/or each valve optionally has a plurality of flow levels. Alternatively or additionally, each lumen or group of lumens is optionally coupled to a different gas source, which optionally stores a different gas or that stores gas at a different pressure.

Control of Capsule Inlet and/or Outlet Formation

In some embodiments of the invention, piercing needles 122 pierce the capsule in capsule chamber 124 for producing capsule inlets. The capsule inlets enable delivery system 120 to penetrate the capsule for delivering the compressed gas thereinto.

In some embodiments, the gas lumens of delivery system 120 are incorporated within piercing needles 122 (for example, as lumens surrounding the axial center of the needle). This coordinates the piercing of the capsule inlets by needles 122 with penetration of the gas lumens into the capsule.

For release of gas, needle(s) optionally have a side hole, and/or a hole at the distal end thereof. A potential advantage to a side aperture in contrast to a distal end aperture is to avoid plugging of the gas aperture by capsule material during penetration. The two types each offer different flow patterns, and are optionally used together and/or alternately.

In some embodiments, the piercing needles 122 also are operable to produce outlets. Optionally, the outlets are produced by piercing from within the capsule interior. The capsule outlets allow the released dry powder medicament to exit the capsule toward airway 104 and mouthpiece 126.

When operated from within the capsule, piercing needles 122 produce the capsule outlets such that the flare of capsule material that surrounds each outlet extends outwardly from the capsule, as described in relation to FIGS. 3A-3G hereinbelow. In other words, the ruptured walls that surround the capsule outlet (these ruptured wall portions are referred to herein as the flare of the capsule outlet or aperture) extend outwardly from the capsule. A potential advantage of this configuration is that the flare is positioned where it avoids trapping powder particles within the capsule.

In accordance with an exemplary embodiment of the invention, piercing needles 122 include at least one needle (not shown) for forming inlets and outlets within the capsule. The piercing needles are constructed (e.g., in terms of structure and materials) such that they can withstand repeated piercing of replaceable capsules; for example, the needles are constructed of stainless steel. To bring about piercing, at least one of capsule chamber 124 (holding the capsule) and piercing needles 122 is movable with respect to the other. Thus, the capsule is moved toward piercing needles 122 (or vice versa) until each needle pierces a capsule inlet in the capsule, and, in some embodiments, motion continues or resumes until each needle (and/or at least one of the needles) pierces a capsule outlet from within the capsule. In this manner, the capsule outlet is pierced from within the capsule, and thereby, the flare of the capsule outlet extends outward from the capsule.

In some embodiments of the invention, a piercing needle 122 is of two or more gauges, having varying diameter (and possibly varying circumferential shape) along the needle. The variation may be discrete (two different two diameters, for example), or continuous (for example, tapering). By this, the diameter of the capsule inlets and outlets is optionally controlled. For example, the capsule outlet is made smaller than the respective inlet.

In accordance with another example, the capsule outlet produced for a first powder material is produced to be of a first shape and size by moving the needle through the outlet until a first section of the needle (having a first cross section) produces the desired outlet. The outlet produced for a second powder material is produced of a second shape and size by moving the needle through the outlet until a second section of the needle (having a second cross section) produces the desired outlet.

Figure 1B:
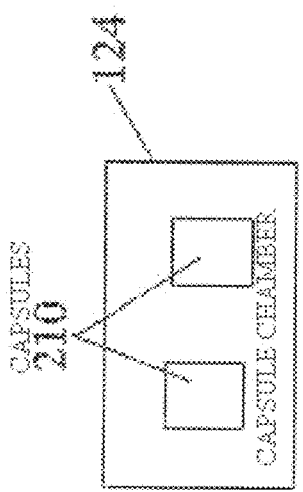
FIG. 1B schematically illustrates a block diagram of optional configurations of capsule chamber(s) and capsule(s) therein, according to some exemplary embodiments of the invention.
Figure 1B:
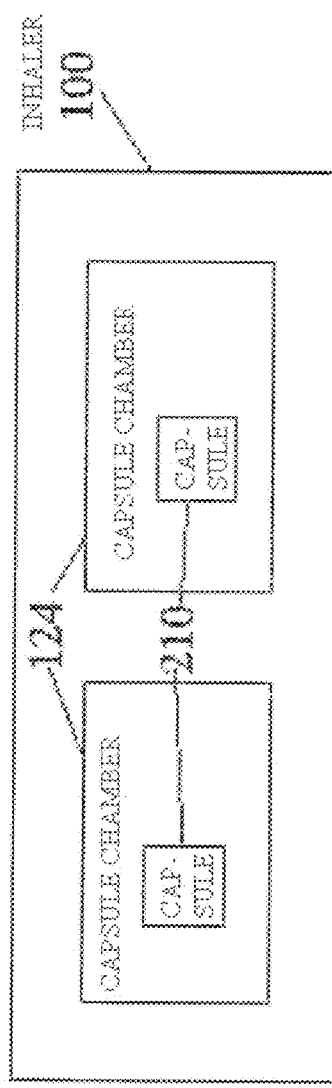
Figure 1B:
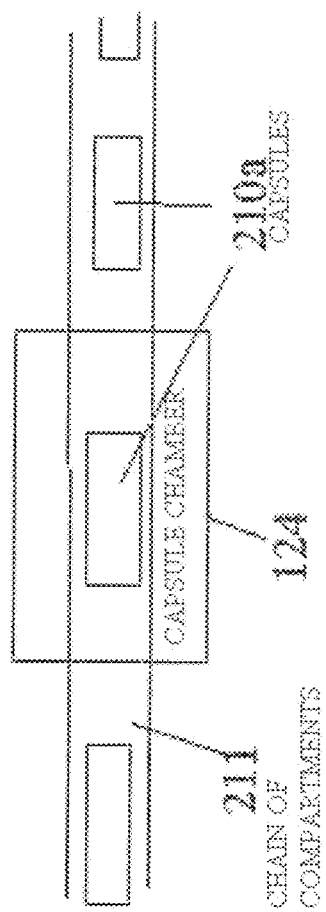
Figure 2:
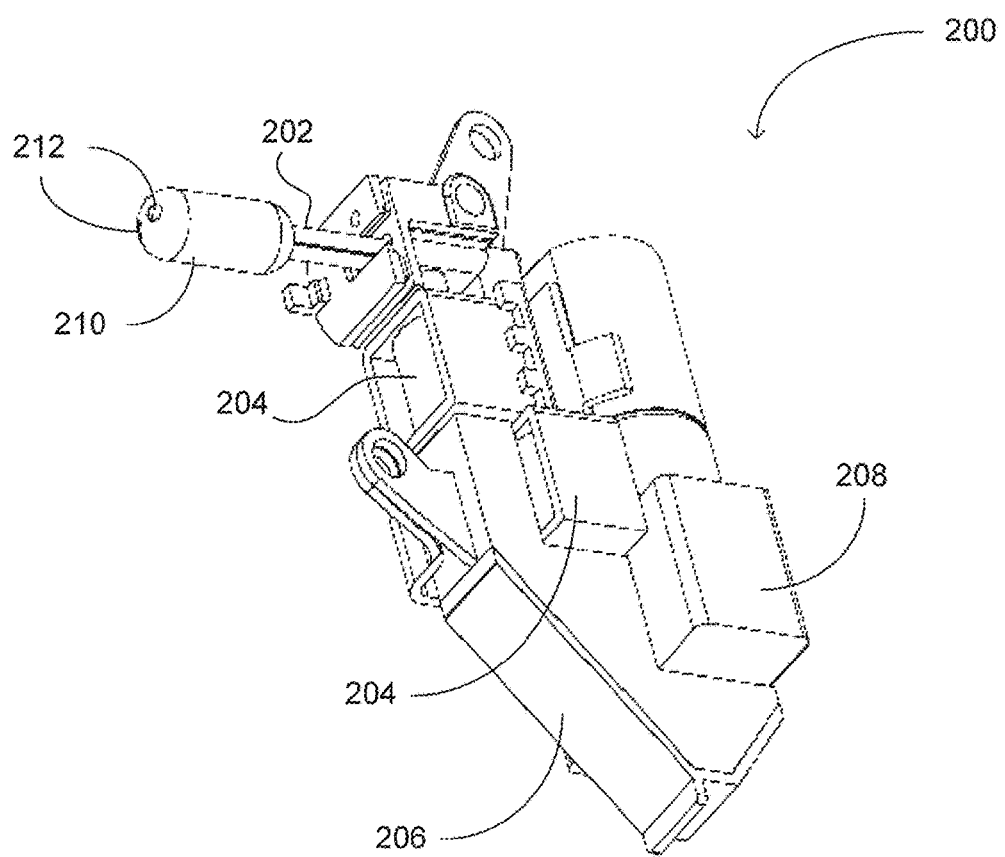
FIG. 2 schematically illustrates a partial view of some of the internal components of a portable active inhaler, according to some exemplary embodiments of the invention.

In another example, an outlet aperture is first made small during an early phase of medicament release, and then widened during a later phase of medicament release. Potentially, this helps to regulate the ratio of deagglomeration to release. For example, the early phase, where the aperture is small, contains the powder so that it is exposed to more of the deagglomerating energy of the compressed gas. The later phase, where the aperture is large, helps to reduce the amount of residual powder by making it more likely for the powder to escape the capsule. The two phases optionally occur during a single breath, and/or are spread over two or more breaths. An exemplary needle structure is detailed further herein below with reference to FIGS. 3H and 3I.

In some embodiments, piercing needles 122 include needles of different lengths. In this configuration, the number of outlet holes can be less than the number of the inlet holes, as the short needle(s) will not reach the distal surface of the capsule during the piercing process.

Exemplary forms of the tip of each of the needle include a cone shaped tip, a beveled tip of various inclination angles, or any other shape suitable for penetration of the capsule material. Use of a side aperture potentially also allows the tip of the needle to be designed for penetration only; for example, as a cone-shaped tip. It is also noted that a cone shaped tip needle creates an approximately circumferential flare surrounding the pierced aperture, while a beveled tip needle tends to create a cut piece (i.e., the piece of the capsule wall cut out by the beveled tip) extending from the aperture.

As mentioned above, in accordance with an embodiment of the disclosed technique, the gas lumens of delivery system 120 are incorporated into piercing needles 122. For example, each of piercing needles 122 includes therewithin a gas lumen ending at a gas outlet. In this manner, the needles pierce the capsule inlet, penetrate therethrough into the capsule and continue to pierce the capsule outlet. Thereafter, the needles are retracted such that the gas outlet of the gas lumen is located within the capsule.

Capsule chamber 124 is a chamber for holding a dry powder medicament capsule. As mentioned above, capsule chamber 124 may be moveable with respect to piercing needles 122 by an actuating mechanism 123. Actuating mechanism may either move capsule chamber relative to the piercing needles 122, or move the piercing needles relative to the capsule chamber. Alternatively, capsule chamber 124 is immobile and needles 122 are moveable. Further alternatively, both capsule chamber 124 and needles 122 are moveable and can both move back and forth, one toward the other. Optionally, each of needles 122 can be moved separately with respect to capsule chamber 124.

In some embodiments of the invention, capsule chamber 124 is adapted to hold conventional capsules (i.e., the capsules are not specially adapted to capsule chamber 124, but are capsules of standard size). Optionally, capsule chamber 124 is made to suit one or more of several sizes of capsules, or to be exchangeable and/or selectable for different sizes. Thus, the capsule can be an ‘off the shelf’ or generic capsule, such as capsules manufactured for use with common types of dry powder inhalers. The capsule can be, for example, a gelatin or HPMC capsule, a blister and/or foil, a capsule made from a single material with no foil.

Additionally or alternatively, capsule chamber 124 can also hold custom-made capsules (i.e., as opposed to conventional, off the shelf, capsules), designed for specific purposes or devices.

In some embodiments, capsule chamber 124 is sized to hold several capsules at the same time, as shown schematically in Example 1 (FIG. 1B). Additionally or alternatively, inhaler 100 includes more than a single capsule chamber, as shown schematically in Example 2 (FIG. 1B).

Optionally, for simultaneous delivery of powders stored in a plurality of capsules, each capsule is pierced by different needle(s) 122, and is provided with compressed gas via different lumen(s). In some embodiments, loading of the capsule into capsule chamber 124, and extracting the capsule from within capsule chamber 124 is performed manually and/or individually. Alternatively or additionally, a magazine or cartridge of capsules is loaded into the inhaler and feeds the inhaler capsules as required—one at a time, or in sets as appropriate. In set-loaded inhaler configurations, several medicaments or doses can be deagglomerated, aerosolized, released, and/or delivered together.

In case capsule chamber 124 holds more than a single capsule, piercing needles 122 pierce at least one of the capsules. Inhaler 100 determines which capsules to pierce according to the medicament powder to be delivered, the dose of powder to be delivered, the capsule loading order (i.e., in case the inhaler is loaded with a cartridge of capsules), or according to other considerations or a combination of the considerations listed above.

It is noted that the capsules loaded into capsule chamber 124 can be independent capsules (i.e., a single unlinked capsule) or physically linked capsules 210*a*, as shown schematically at Example 3 (FIG. 1B). Linked capsules are a group of capsules physically connected such that they form together a continuous chain 211 of dry powder compartments. Thus, for example, inhaler 100 can be a disc (or square) type dry powder inhaler receiving powder disc into capsule chamber 124.

Production of Different Gas Flow Regimes within the Capsule

Reference is now made to FIGS. 3A-3I, which are schematic illustrations of a capsule of medicament dry powder 300, pierced by the piercing needles 302 of a portable active inhaler, and provided with compressed gas via gas outlets 304 of gas lumens, according to some exemplary embodiments of the invention.

FIG. 3A depicts capsule 300 after the piercing needles have pierced a pair of entrance apertures in the walls thereof. FIG. 3B depicts capsule 300 after the piercing needles have additionally pierced a pair of exit apertures 310 in the walls thereof. FIG. 3C depicts capsule 300 after the piercing needles have retracted such that the outlet ports of the fluid lumen within the capsule are positioned within the capsule, and the exit apertures 310 are clear for the outflow of gas from the capsule. FIG. 3D depicts a first gas flow regime within capsule 300. FIG. 3E depicts a second gas flow regime within capsule 300. FIG. 3F depicts a third gas flow regime within capsule 300. FIG. 3G depicts various exemplary gas outlets. FIG. 3H depicts the external shape of needle 302A from a side view perspective. FIG. 3I depicts the external shape of needle 302A from a top view perspective.

With reference to FIG. 3A, capsule 300 is held within a capsule chamber of an inhaler (chamber positioning of the capsule is discussed in relation to FIGS. 4A-4F hereinbelow). Once the user loads capsule 300 within the capsule chamber and primes the inhaler, the capsule chamber is moved toward needles 302 until the needles pierce respective capsule inlets 306 in the wall of capsule 300 proximal to the needles. As can be seen in FIG. 3A, when piercing capsule inlets 306, needles 302 produce a flare of the capsule wall extending in the direction of the piercing direction. That is, when piercing inlets 306 from outside capsule 300, flares 308 extend inwards into capsule 300. It is noted that flares 308 extend inwards into capsule 300 and embrace the needles. Thereby, the proximal side of capsule 300, in which entrance apertures 306 (i.e., capsule inlets 306) are pierced, has no corners, and thus powder is easily extracted from capsule 300 and the amount of residual powder is decreased.

With reference to FIG. 3B, the capsule chamber further moves toward needles 302 until the needles pierce respective capsule outlets 310 in the distal wall of capsule 300. As can be seen in FIG. 3B, when piercing capsule outlets 310, needles 302 produce a flare of the capsule wall extending in the direction of the piercing direction. That is, when piercing outlets 310 from within capsule 300, flares 312 extend outward from capsule 300. Thereby, flares 312 do not trap any dry powder particles within capsule 300, thus decreasing the amount of residual powder that is not extracted from capsule 300.

With reference to FIG. 3C, the capsule chamber retracts away from needles 302, such that capsule outlets 310 are clear (i.e., unblocked by needles 302), and such that gas outlets 304 of needles 302 (i.e., of the gas lumens incorporated within needles 302) are positioned within capsule 300 for delivering compressed gas into capsule 300.

The needles of the inhaler device deliver the compressed gas into the capsule. The inhaler device can produce several gas flow regimes within the capsule. By employing a plurality of gas flow regimes, the inhaler potentially decreases the amount of residual powder remaining trapped within the capsule. Furthermore, the various gas flow regimes enable the inhaler to deagglomerate, aerosolize, mix and release various dry powder materials which may differ in the size of the particles, and other parameters of the dry powder and of the potential carrier material within the capsule. Additionally, different regimes (or combinations of regimes) can be used for deagglomerating and dispersing different mixtures of materials, and can further be used for producing particles of different sizes (e.g., for delivering the powder to different body locations).

FIGS. 3D-3F depict three exemplary gas flow regimes produced by pair of needles 302.

With reference to FIG. 3D, gas flow regime 320 is produced within capsule 300 by delivering compressed gas from a needle 302A, while keeping a needle 302B shut. It is noted that the gas path (i.e., trajectory) within capsule 300 is similar to a counterclockwise helix. With reference to FIG. 3E, gas flow scheme 322 is produced within capsule 300 by delivering compressed gas from needle 302B, while keeping needle 302A shut. It is noted that the gas path within capsule 300 is similar to a clockwise helix. With reference to FIG. 3F, gas flow regime 324 is produced within capsule 300 by delivering compressed gas from both needle 302A and needle 302B. Potentially, this gas flow regime 324 is turbulent. It is a potential advantage to administer two or more (for example, all three) of these flow regimes during dispersal of a medicament. For example, if static zones allowing powder buildup are set up by a clockwise helix, a strong-flowing counterclockwise helix has the potential to disrupt the pattern that allowed this deposition, re-suspending powder from the former region of static flow (and vice-versa). A turbulent flow potentially leaves no constant static region of powder accumulation behind, but also potentially does not develop the highest gas velocities for resuspension/deagglomeration. Thus, the mix of high turbulence, and high, alternating-direction velocities potentially covers a range of conditions which together serve to sweep the great bulk of residual powder out of the capsule.

Optionally, the needles 302A, 302B are positioned with one more eccentric to the capsule's central axis than the other. Optionally, the needles 302A, 302B are positioned with one further advanced along the capsule length than the other. Potentially, this allows setting up axially or otherwise spatially separated patterns of flow, for example, regions of higher and lower pressure, regions separated by a layer of difference in flow velocity, or another combination of flow patterns. Optionally, the flow patterns generated are selected for control of particle motion between them; for example, a boundary optionally impedes (or encourages) motion across itself, and/or optionally selectively impedes (or encourages) crossing of larger, smaller, denser, and/or less-dense particles.

For further varying the gas flow regimes and for producing additional gas flow regimes, the following are example of parameters and characteristics controlled in some exemplary embodiments of the invention.

The number of fluid lumens penetrating the capsule. Potentially, a larger number of lumens can produce a larger number of regimes by controlling the flow from the lumens.

The number, shape and size of each gas outlet of the gas lumens. Potentially, larger ports enable higher flows of gas.

The shape of the outlet. Potentially, this affects air currents set up within the capsule by the flow of gas through the outlet.

Number of gas inlets per lumen. Each lumen optionally includes more than a single inlet.

Adjustable inlet states. Outlets are optionally opened closed, and/or partially opened, thereby controlling the outlet size and possibly also the outlet shape.

Adjustable gas flow via to the lumen. Control (e.g., by valves) of gas access to a lumen is optionally exerted for producing different gas flow regimes.

Bursts of gas, and their duration and frequency. Optionally, the gas delivery system provides bursts of compressed gas. Optionally, duration and frequency of the bursts from each of the outlets can be controlled for producing different flow regimes.

Positions of the outlets within the capsule. Optionally, outlet positions are controlled for producing different regimes. For example, the outlets of a first lumen are positioned at a different location than those of another lumen. Additionally or alternatively, the capsule is movable with respect to the needles, and thereby the positions of the outlets within the capsule interior are changed. Additionally or alternatively, opening and closing different outlets changes the position of the open outlets.

With reference to FIG. 3G, needle 302A, in some embodiments, includes a single gas outlet 304A, and needle 302B includes, for example, three gas outlets 304B, 304C and 304D (or any other number appropriate for the flow regime (s) to be supported). Outlet 304A is in the shape of an elongated ellipse, outlet 304B is in the shape of an elongated rectangle, outlet 304C is in the shape of a square, and outlet 304D is in the shape of a triangle. Outlet 304B is located proximally to outlet 304C, that in turn is located proximally to outlet 304D. Outlet 304D faces a different portion of capsule 300 that each of outlets 304A, 304B and 304C. Thus, the gas outlets can vary in shape, size, location, direction, and other physical parameters for producing various gas flow regimes within capsule 300. It can be readily understood that other variations of these parameters also comprise embodiments of the current invention, in view of the exemplary variations just described.

With reference to FIGS. 3H and 3I, needle 302A, in some embodiments, is a multi-gauge needle having varying external shape and size (i.e., varying external cross section). In a particular example, needle 302A has three varying sections, proximal section 320, middle section 322 and distal section 324.

Optionally, sections 320, 322 and 324 are of different external cross sections. In the example set forth in FIGS. 3H and 3I, proximal section 320 has a square shape and a diameter (i.e., size) of D1; middle section 322 has a round shape and a diameter of D2 smaller than D1; and distal section 324 has an octagonal shape and a diameter of D3 smaller than D2. Thereby, in case needle 302A pierces the capsule outlet by extending only with distal section 324 through the distal capsule wall, the capsule outlet would have an octagonal shape and a diameter of D3. In case needle 302A pierces the capsule outlet by extending with middle section 322 through the distal capsule wall, the capsule outlet would have a round shape and a diameter of D2. In case needle 302A pierces the capsule outlet by extending with proximal section 320 through the distal capsule wall, the capsule outlet would have a square shape and a diameter of D1. Thus, different capsule outlet having different external shape and different diameters can be produced by needle 302A, for adapting the capsule outlet to the capsule, to the dry powder within the capsule, to the patient, and the like. It should be understood that continuous cross-section variation is also used in some embodiments of the current invention. For example, a needle is tapered, and/or has a shape which continuously varies from a first shape to a second shape.

Methods of Outlet Preparation and Gas Delivery

Method of Outlet Preparation and Use

Reference is now made to FIG. 8, which schematically illustrates a method for delivering dry powder medicament to a user and piercing outward capsule outlets, according to some exemplary embodiments of the invention.

At block 800, in some embodiments, capsule inlets and capsule outlets are pierced in the walls of a dry powder medicament capsule, such that the flares of the capsule outlets extend outwardly from the capsule. With reference to FIGS. 3A and 3B, needles 302 pierce capsule inlets 308 and capsule outlets 310. It is noted that flares 312 of capsule outlets 310 extend outwardly from capsule 300. The outwardly extending flares of the capsule outlets do not trap powder particles within the capsule.

At block 802, in some embodiments, the capsule is penetrated with a gas delivery system. The gas delivery system penetrates the capsule for delivering compressed gas into the capsule, for deagglomerating the dry powder within the capsule, for aerosolizing the powder, and for releasing the powder from the capsule. With reference to FIGS. 3A and 3C, needles 302 penetrate into capsule 300, such that gas outlets 304 are positioned within capsule 300 for directing the compressed gas into capsule 300. Optionally, aspects of block 800 and block 802 are combined, for example when piercing needles 302 comprise the gas delivery lumens of the gas delivery system.

At block 804, in some embodiments, compressed gas is provided to the gas delivery system. For example, with reference to FIG. 2, accumulator 206 provides compressed gas to the gas delivery system (i.e., to the gas lumens within needles 202). In some embodiments, another pressurized gas source is used, such as a compressed gas canister.

At block 806, in some embodiments, the compressed gas is directed into the capsule by the gas delivery system.

Plurality of Intra-Capsule Dispersing/Deagglomerating Gas Outlets

Figure 9:
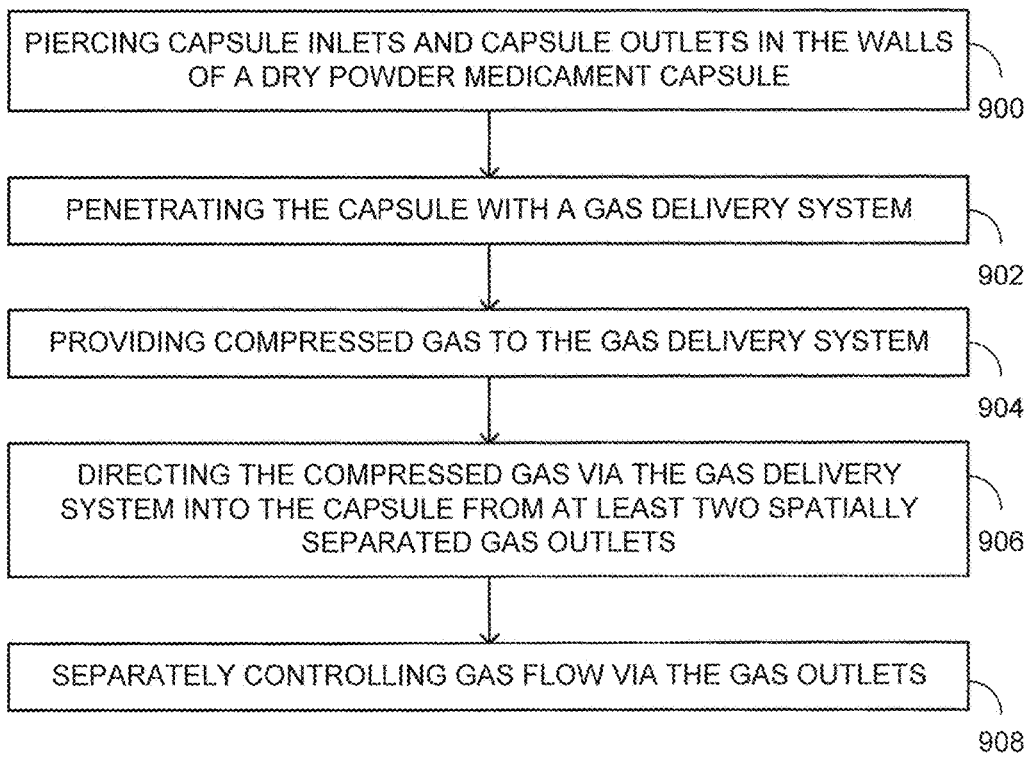
FIG. 9 schematically illustrates a method for delivering dry powder medicament to a user and producing various gas flow regimes within a dry powder medicament capsule, according to some exemplary embodiments of the invention.

Reference is now made to FIG. 9, which schematically illustrates a method for delivering dry powder medicament to a user and producing various gas flow regimes within a dry powder medicament capsule, according to some exemplary embodiments of the invention.

Figure 3A:
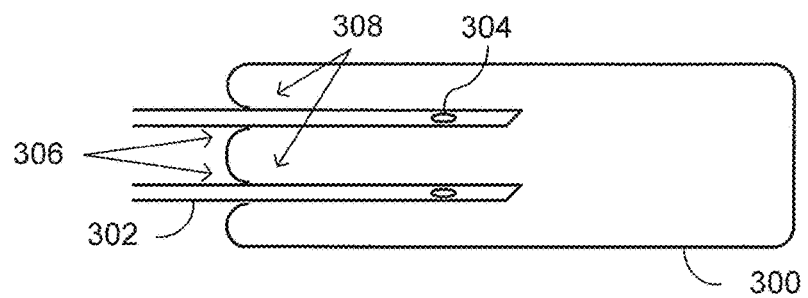
FIGS. 3A-3I schematically illustrate a capsule of medicament dry powder, pierced by the piercing needles of a portable active inhaler, and provided with compressed gas via the needles, according to some exemplary embodiments of the invention.
Figure 3B:
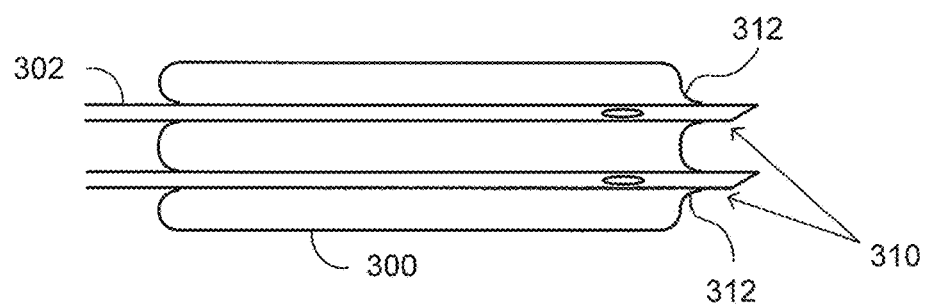
Figure 3C:
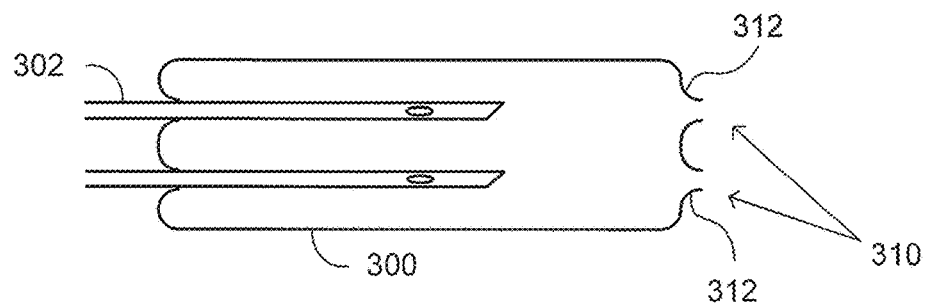
Figure 3D:
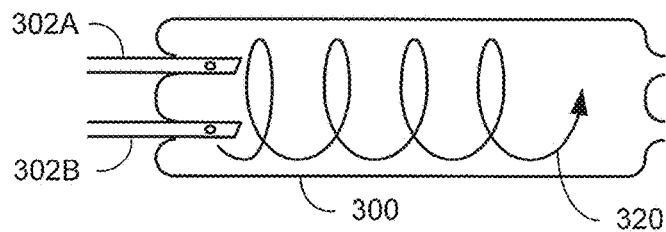
Figure 3E:
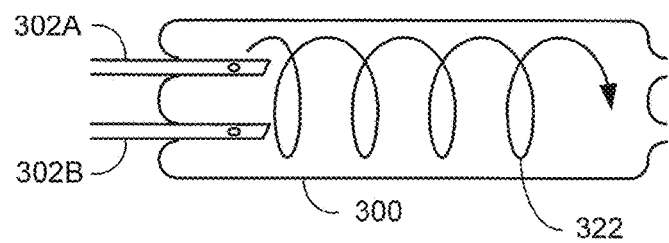
Figure 3F:
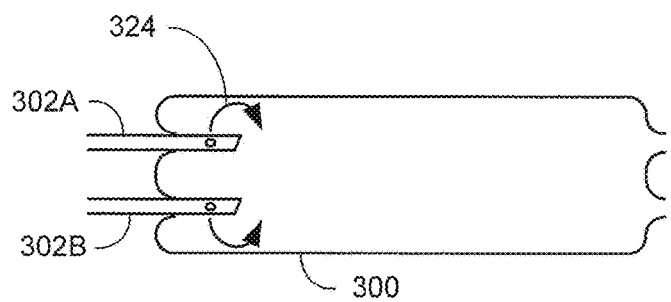
Figure 3G:
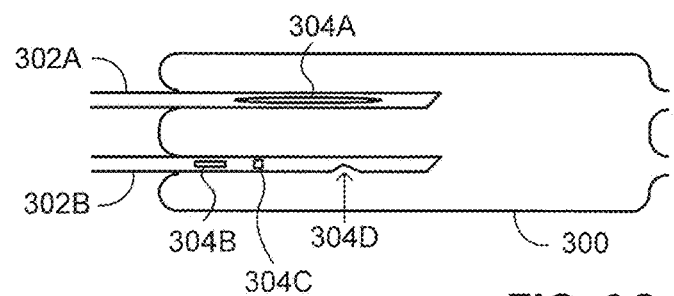
Figure 3H:
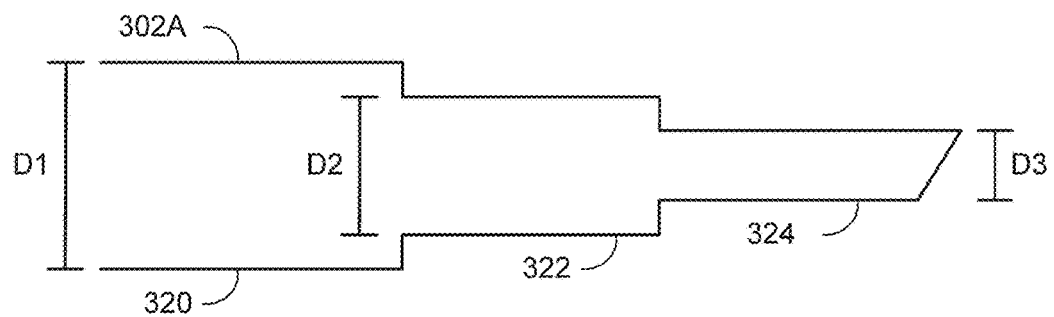
Figure 3I:
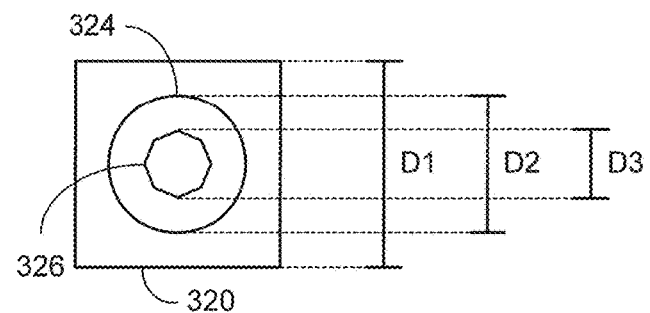

At block 900, in some embodiments, capsule inlets and capsule outlets are pierced in the walls of a dry powder medicament capsule. With reference to FIGS. 3A and 3B, needles 302 pierce capsule inlets 308 and capsule outlets 310.

At block 902, in some embodiments, the capsule is penetrated with a gas delivery system. The gas delivery system penetrates the capsule for delivering compressed gas into the capsule, for deagglomerating the dry powder within the capsule, for aerosolizing the powder, and for releasing the powder from the capsule. With reference to FIGS. 3A and 3C, needles 302 penetrate into capsule 300, such that gas outlets 304 are positioned within capsule 300 for directing the compressed gas into capsule 300.

At block 904, in some embodiments, compressed gas is provided to the gas delivery system. With reference to FIG. 2, accumulator 206 provides compressed gas to the gas delivery system (i.e., to the gas lumens within needles 202). In some embodiments, another pressurized gas source is used, such as a compressed gas canister.

At block 906, in some embodiments, the compressed gas is directed via the gas delivery system into the capsule, optionally from at least two spatially separated gas outlets.

At block 908, in some embodiments, gas flow via the gas outlets is separately controlled. For example, gas flow from the gas outlets is controlled with separately openable and closeable gas outlets, for enabling directing the compressed gas into the capsule from different gas outlets and/or combinations of gas outlets. With reference to FIGS. 2 and 3D-3F, each of valves 204 controls the gas flow through each of needles 202 (and thereby through the gas outlets of needles 202). Thus, valves 204 optionally allow the compressed gas to be directed into capsule 210 via a first one of needles 202 (e.g., needle 302A of FIGS. 3D-3F, as depicted in FIG. 3E), via a second one of needles 202 (e.g., needle 302B of FIGS. 3D-3F, as depicted in FIG. 3D), or via both needles (e.g., needles 302A and 302B of FIGS. 3D-3F, as depicted in FIG. 3F).

Exemplary Inhalers

Internal Components of an Exemplary Inhaler

Reference is now made to FIG. 2, which is a schematic illustration of a partial view of some of the internal components of a portable inhaler 200, for outwardly piercing an exit aperture in a capsule, according to some exemplary embodiments of the invention.

In some embodiments, inhaler 200 includes a pair of piercing needles 202, a pair of solenoid valves 204, an accumulator 206 and a pump 208.

In the example set forth in FIG. 2, each of needles 202 includes a gas lumen incorporated therein, and in fluid communication with accumulator 206 (or another pressurized gas source) via a respective one of valves 204. For example, a first needle is coupled with the accumulator via a first valve, and a second needle is coupled with the accumulator via a second valve. In some embodiments, accumulator 206 is further in fluid communication with pump 208.

In some embodiments, needles 202 are employable for piercing exit apertures 212 (i.e., capsule outlets 212) in a capsule 210 filled with a dry powder. Optionally, needles 202 are employed as passageway for gas from a gas source into capsule 210. Needles 202 are made of materials and in a shape that enables each of needles 202 to pierce through the walls of capsule 210, for producing apertures in capsule 210. For example, the needles are longitudinally extended members of stainless steel. It can be understood that other shapes are possible. For example, in some embodiments, a curved needle is driven along a path which rotates a portion of its body through the capsule interior. Optionally, the inlet and outlet are thus created with any suitable relative position (not only in opposite ends, for example), according to the curvature and path of the needle.

In some embodiments, accumulator 206 comprises a compressed gas tank for storing gas compressed by pump 208. The pressure of the compressed gas within accumulator 206 is determined by the volume of accumulator and by the amount of gas pumped into accumulator by pump 208. Together, pump 208 and accumulator 206 form a compressed gas source (not referenced). Optionally, the compressed gas source of accumulator 206 and pump 208 can be replaced (or augmented) with other compressed gas sources. Each of the gas sources can have different quantities of gas, and can store the gas at different pressures. Each of the gas sources can include a different gas or combination of gases.

Inhaler 200, in some embodiments, includes a battery (not shown) or another power source for providing power to the various components of inhaler 200, for example, valves 204, pump 208, controllers, and/or sensors. In some embodiments, inhaler 200 includes a capsule chamber (not shown) for receiving capsule 210 and/or for moving capsule 210 back and forth with respect to needles 202.

In some embodiments, inhaler 200 includes a controller, a flow sensor, a communication port, a LED, and/or a buzzer (all not shown), optionally mounted on one or more printed circuit boards (PCB). Optionally, controller is coupled with the flow sensor, the communication port, the LED, and/or the buzzer. Additionally or alternatively, the controller is coupled with valves 204, pump 208, and/or the flow sensor. Where provided, the controller controls the operation of inhaler 200; for example, according to the readings of the flow sensor.

Capsule Preparation in an Exemplary Inhaler

In some embodiments, preparing the inhaler for use comprises the capsule chamber being brought together with needles 202 until needles 202 pierce capsule inlets in the wall of a capsule which the chamber contains. Optionally, further motion brings the needles 202 to pierce the capsule outlets at the wall of the capsule opposite to the inlets. In this manner, needles 202 pierce the capsule outlets from within the capsule itself and outwardly (i.e., referred to herein as intra capsule piercing or outward piercing). Thereby, the flares of the capsule outlets (i.e., ruptured capsule wall surrounding the outlets) extends outwardly from the capsule, and does not trap powder particles within the capsule during powder dispersion.

In some embodiments, the outlet piercing motion is laterally, radially, or otherwise directed to bring about a different relative position of inlets and outlets, and/or to vary the shape of an outlet. Optionally, for example, a needle comprises a blade-like portion near its tip (that is, sharpened along the length of the needle), allowing slicing as well as piercing of the capsule wall. In some embodiments, a priming operation of the inhaler causes such a needle to pivotingly slice along the capsule wall once the outlet is pierced (the pivot point being, for example, at about the point of inlet entry of the needle). Potentially, this allows wider aperture at the outlet side than was created at the inlet side of the capsule, even if needle base is larger than the needle tip. Additionally or alternatively, the needle rotates to slice; for example, in an embodiment where a blade edge is radially offset from the axis of the main needle body, optionally due to a bend in the needle. In some embodiments, the piercing is initially accomplished by a slicing motion (pivot or rotation, for example).

After piercing, in some embodiments, the capsule chamber moves away from needles 202 until the capsule outlets are clear, while maintaining the gas outlets of the gas lumens within the capsule.

Alternatively, in some embodiments, a portion of the needle forms a gas/medicament suspension outlet lumen. For example, the needle is divided into sections, a first of which has a gas inlet into the capsule chamber, and a second of which comprises an outlet aperture inside the capsule, leading to a lumen having a second aperture outside the capsule. In some embodiments, the second needle section comprises an aperture long enough to extend from the interior of the capsule to the capsule exterior, across the outlet aperture created by piercing.

With the capsule opened, and the gas outlets of the gas lumens are within the capsule, needles 202 can deliver compressed gas into the capsule for dispensing the dry powder to the patient. In the example set forth in FIG. 2 there are two needles and two valves. Alternatively, there could be another number of valves or of needles, such as one valve and one needle, one valve and three needles (e.g., the valve regulates the flow of all three needles), three valves and three needles, two valves and four needles (e.g., each valve regulates the flow of two of the needles), or any other combination.

In case of two or more gas outlets, inhaler 200 can generate a plurality of flow regimes of within the capsule. For example, in case of two gas outlets, inhaler 200 can deliver compressed gas into the capsule via a first outlet, via a second outlet, or via both outlets together. Thereby, three different gas flow regimes can be produced within the capsule. Furthermore, in accordance with another embodiment of the disclosed technique, the extent to which each of valves 204 is open can also be controlled. That is, each of valves 204 can have several flow levels (e.g., a high, medium and low flow level). In this manner, more gas flow regimes can be produced within the capsule. Moreover, inhaler 200 can deliver the compressed gas in a series of bursts, and control the duration and frequency of the bursts by employing valves 204. Thus, inhaler 200 can further vary the gas flow regimes (e.g., employing different frequency of bursts from each of the fluid lumens). In accordance with alternative embodiment, each of the gas lumens is coupled with a respective compressed gas source instead of being coupled to the same gas source via different valves (e.g., two gas sources for two gas lumens).

By employing different gas flow regimes, the extraction of dry powder from the capsule is potentially increased, and the amount of residual powder trapped within the capsule is reduced. Additionally or alternatively, the different gas flow regimes control (for example, increase) deagglomeration of the dry powder medicament. In some embodiments, this allows adapting the deagglomeration (and the release and delivery) to the specific dry powder medicament within the capsule (or to several powders, either in a single capsule or in separate capsules), to a specific patient and/or a specific treatment plan.

In some embodiments, the needle/capsule subassembly is formed to allow other configurations of flow besides inflow/mix/outflow and release. For example, the needle and capsule subassembly optionally comprises a circuit that allows at least some of the gas entering the capsule to exit the capsule to a route into a secondary deagglomeration chamber, and/or allows circulation of powder suspension in and out of the capsule before final release. Although adding more surfaces/chambers potentially increases residual powder losses, there is a potential advantage in allowing a longer confined exposure to energies which cause particle deagglomeration. In contrast, there is a potential reliability advantage in making the capsule wall as such the main or only outlet for particle laden gas: since the capsule is discarded after each use, there is no risk of gradual powder buildup leading to outlet plugging. As the gas inlet needle is operated under forward pressure, the risk of plugging there is low. Nevertheless, in some embodiments of the invention, needles are periodically replaceable, for example, as part of a disposable module.

Priming of an Exemplary Inhaler

Reference is now made to FIGS. 4A-4F, which are schematic illustrations of a portable active inhaler generally referenced 400, according to some exemplary embodiments of the invention.

The preparation of the capsule described with respect to the internal components of an inhaler 200 involve various user actions for priming, examples of which are now described in relation to an inhaler 400.

Specifically, FIG. 4A depicts an embodiment of an inhaler 400 prior to loading a capsule 420 thereinto. FIG. 4B depicts inhaler 400 loaded with the capsule and having with the priming knob slightly rotated. FIG. 4C depicts a cross section view of inhaler 400 with the priming knob slightly rotated. FIG. 4D depicts a cross section view of inhaler 400 with the priming knob almost completely rotated. FIG. 4E depicts inhaler 400 with the priming knob fully rotated. FIG. 4F depicts a cross section view of inhaler 400 with the priming knob fully rotated.

With reference to FIG. 4A, inhaler 400, in some embodiments, includes a pair of piercing needles 402 (FIG. 4C), a capsule chamber 404, a priming knob 406 and a mouthpiece 408. Inhaler 400 further includes other components, such as all the components detailed with reference to FIG. 1A.

In some embodiments, needles 402 serve both as piercing mechanism and as gas delivery system. Thus needles 402 are constructed such that they can withstand repeated piercing of capsules. Optionally, the needles are replaceable in the inhaler after a chosen service lifetime. Furthermore needles 402 include a gas lumen and gas outlet for delivering compressed gas from a gas source of inhaler 400 (e.g., a pump and an accumulator) into a capsule 420 loaded into capsule chamber 404. Capsule chamber 404 is movable with respect to needles 402, such that needles 402 can pierce capsule 420 loaded into chamber 404. It is noted that capsule 420 can be any conventional capsule (i.e., capsule 420 does not have to be specifically adapted to inhaler 400), or alternatively can be a custom made capsule. In particular, Capsule chamber 404 is adapted for receiving various types of capsules. Additionally, capsule chamber 404 can be adapted for holding more than a single capsule. Alternatively, inhaler 400 can include more than a single capsule chamber for holding more than a single capsule.

Priming knob 406 actuates capsule chamber 404 toward and away from needles 402 for piercing the loaded capsule, as would be detailed further below. Mouthpiece 408 is attached to the mouth of a patient (not shown) and provides passage out of and into inhaler 400.

Capsule 420 containing dry powder medicament (not shown) is manually loaded into capsule chamber 404. Prior to employing inhaler 400 for dispensing the dry powder to the patient, inhaler 400 should be loaded, primed and set up. In accordance with an embodiment of the disclosed technique, the priming and set up of inhaler 400 are performed when the user rotates priming knob 406 by 180°. In some embodiments, for example, once the user (e.g., the patient or a physician) rotates priming knob 406, a pump of inhaler 400 starts compressing air into an accumulator, serving as a compressed gas source. Additionally or alternatively, another pressure source is prepared and/or verified as appropriate.

In some embodiments, during rotation of priming knob 406, each of piercing needles 402 pierces respective capsule inlets and outlets in capsule 420, as described in relation to FIGS. 4B-4F.

Figure 4A:
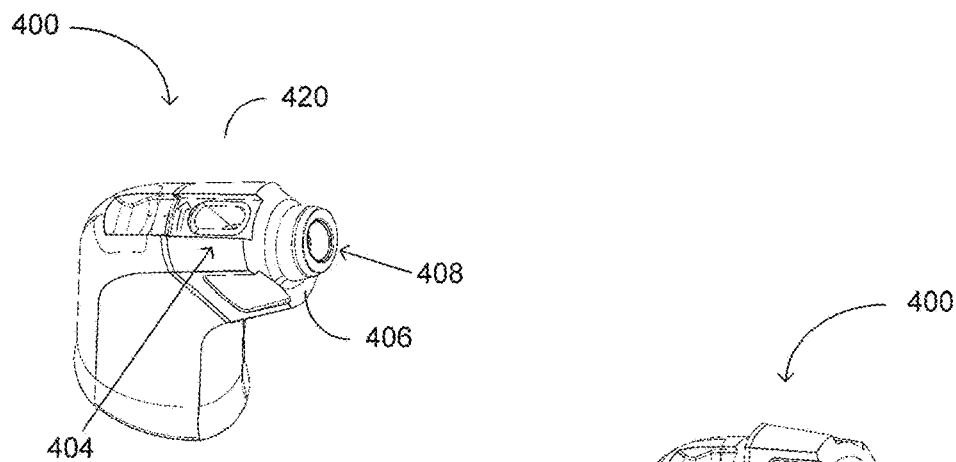
FIGS. 4A-4F schematically illustrate a portable active inhaler, according to some exemplary embodiments of the invention.
Figure 4B:
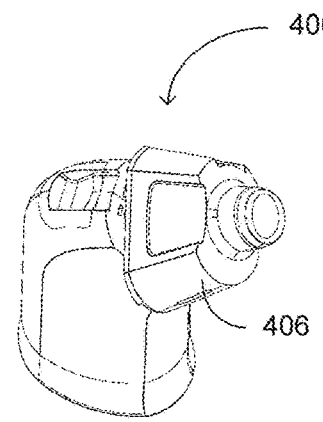
Figure 4C:
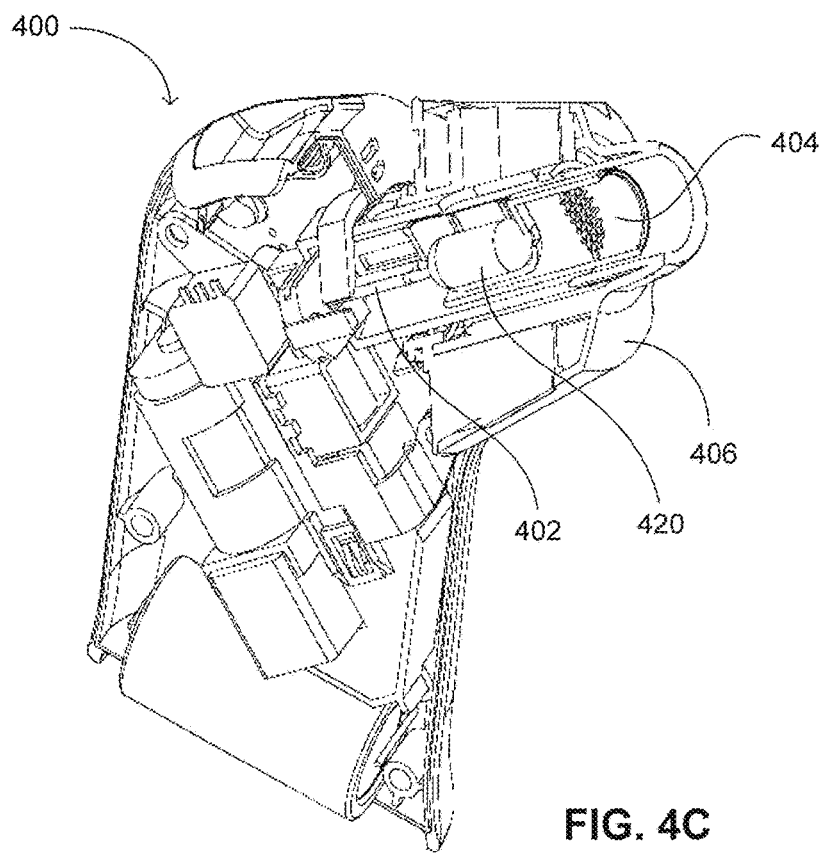

With reference to FIG. 4B, inhaler is depicted such that priming knob 406 is slightly rotated. Once the user starts rotating priming knob 406, the priming of inhaler 400 begins. With reference to FIG. 4C, as can be seen in the Figure, with priming knob 406 is slightly rotated capsule chamber 404 is moved toward needles 402. Needles 402 pierce capsule inlets in the proximal wall (i.e., closest to the needles) of capsule 420.

Figure 4D:
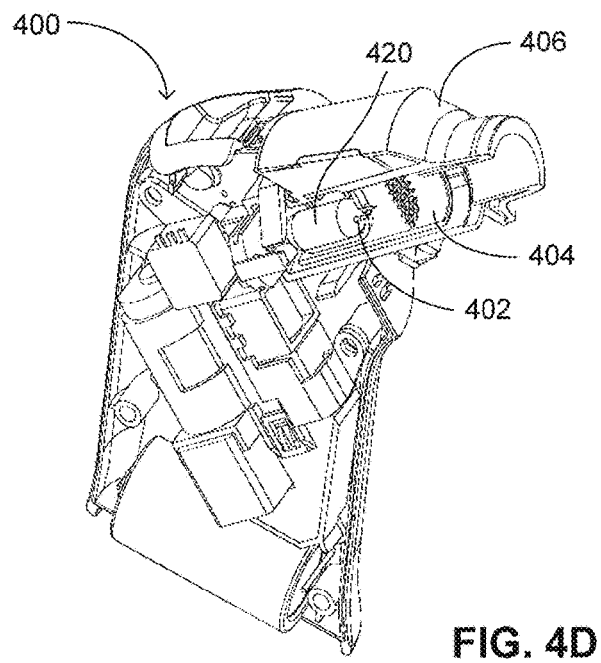

With reference to FIG. 4D, as the user continues rotating priming knob 406, capsule chamber 404 is further moved toward needles 402. Needles 402 pierce capsule outlets in the distal wall of capsule 420, from within the capsule. In this manner, the flare of the capsule outlets extends outwardly from capsule 420 and does not trap powder particles within capsule 420. Thus, the intra capsule piercing of the capsule outlets decreases the amount of wasted residual powder particles. Needles 402 can be multi-gauge so that the diameter of the capsule outlets would be smaller than that of the inlets. Moreover, the circumferential shape of needles 402 determines the shape of the capsule inlets and outlets. Additionally, different needles of needles 402 can be of different length, or different needles are separately actuated, such that the number of capsule outlets is smaller than the number of capsule inlets (i.e., only some of the needles reach the distal wall and pierce a respective capsule outlet). It is to be understood that other variations of needle and/or inlet/outlet aperture position, shape, function, and/or movement as described, for example, in relation to FIGS. 1, 2, and/or 3A-3I are provided in some embodiments of the invention additionally, and/or alternatively.

Figure 4E:
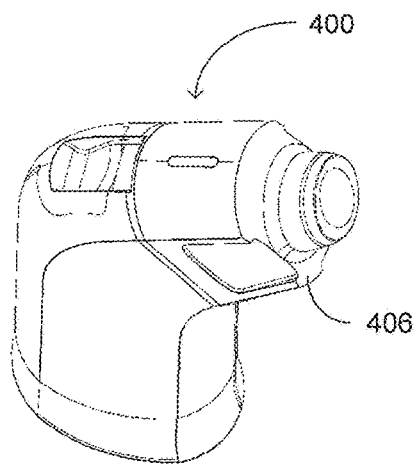
Figure 4F:
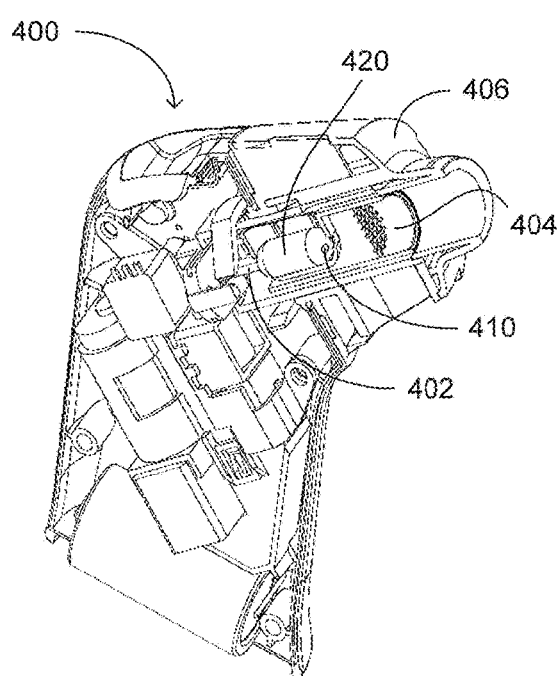

With reference to FIG. 4E, the user has completed the 180° rotation of priming knob 406, and inhaler 400 is primed and set up for delivering the medicament to the patient. With reference to FIG. 4F, after needles 402 pierced outlets 410 in the distal wall of capsule 420, as priming knob 406 completes its 180° turn, chamber 404 is moved away from needles 402. Thus, outlets 410 of capsule 420 are free and allow extraction of the dry powder therethrough. Additionally, the gas outlets of the gas lumens of needles 402 are positioned within capsule 420. In some embodiments, another final motion is performed to bring about the intended final position of the needles and their apertures relative to the capsule, for example, any position as described hereinabove. In this manner, compressed gas passing through needles 402 is evacuated within capsule 420 and is employed for deagglomerating, aerosolizing, and/or releasing the dry powder within capsule 420. Needles 402 are coupled with the accumulator (or other pressure source) via respective valves, and thus several gas flow regimes can be produced within capsule 420.

In some embodiments, an at least one switch is activated when the rotation is completed, turning on the electric circuit which places the inhaler 400 into a stand-by mode. Optionally, an indication is provided to the user that the device is ready to deliver the drug, for example, by illuminating a signaling LED, and/or providing another visible, audible, and/or tactile signal.

Gas Delivery in an Exemplary Inhaler

Returning now to FIG. 2, the operation of inhaler 200 to deliver pressurized gas to a prepared and primed dry powder capsule is detailed hereinbelow.

In some embodiments, a user inserts capsule 210 into the capsule chamber and primes inhaler 200 by rotating a priming knob, for example as described with reference to FIGS. 4A-4F hereinbelow. Optionally, priming of inhaler 200 involves pump 208 pumping air into accumulator 206, and/or other preparation of the pressurized gas source. In some embodiments, priming of inhaler 200 further involves moving the capsule chamber together with the needles for piercing capsule inlets and outlets in the walls of the capsule, and/or retracting the capsule chamber for positioning the gas outlets (i.e., of the gas lumens within the needles) within the capsule.

In some embodiments, pump 208 inflates accumulator 206 to an appropriate pressure, optionally the highest pressure that pump 208 is capable of (e.g., pressure of 1 bar, 5 bars, 10 bars or another greater, lesser, or intermediate pressure). By employing an accumulator to store the compressed gas, the inhaler can deliver larger volumes of compressed gas at the desired pressure, than the volumes that are produced in real time by the pump itself.

In some embodiments, the flow sensor detects the inhalation flow rate of the patient. When the controller determines that a desired flow rate threshold is exceeded (or that another release condition is reached), inhaler 200 disperses the powder content out of the capsule, while breaking the powder particles to a powder fineness appropriate to reaching the target site. Optionally, the controller compares the patient performance to the required performance (e.g., in terms of flow rate or inhaled volume) and employs the buzzer and/or the LED light to correct and guide the patient in real time. Data are optionally stored in an internal memory, from which the physician can optionally download the data via a communication port. Optionally, the physician can receive any information about the way the patient used the inhaler in real time, and/or throughout the last minutes, days, weeks, months and/or years.

Once the desired inhalation threshold is achieved, pump 208 optionally starts working again, while valves 204 (for example, solenoid valves) are opened and closed to produce preprogrammed and/or dynamically determined gas flow regime(s) within capsule 210 (e.g., pulses of air flow in the capsule or continues flow from both or one of the needles). Thus, inhaler 200 includes an active delivery system that is optionally operated in a closed-loop control. It is noted that the dry powder medicament can be selectively delivered to the patient only during the inhalation phase, for example, in a single inhalation phase or in a plurality of inhalation phases.

Other Aspects of the Active Inhaler and its Use

Inhaler Mouthpieces

Returning now to FIG. 1A: to operate the inhaler, the inhaler mouthpiece 126 is placed to the mouth of the patient. Mouthpiece 126 is an adapter for conveniently attaching airway 104 to the mouth of the patient. The patient inhales the delivered dry powder medicament through mouthpiece 126. Alternatively, mouthpiece 126 can be replaced by a facemask which is attached to the face of the patient. Further alternatively, mouthpiece 126 is replaced with a nasal adapter for coupling airway 104 to the nose of the patient.

The facemask (or the nasal adapter) is optionally employed for patients that require drug delivery over several breathing cycles, such as children, elderly people and people with respiratory problems. Additionally, the facemask can be used for patients that cannot hold the mouthpiece to their mouth, such as handicapped patients, unconscious patients, and the like. Furthermore, the facemask can be employed for patients, to whom it is difficult to explain how to employ the inhaler, such as people with mental problems. Additionally or alternatively, a potential advantage of dividing administration over several inhalation cycles is to prevent administering enough powder in one to trigger a cough reflex. This can be in order to make individual deliveries smaller, and/or to allow a larger powder load (likely to trigger a reflex cough, for example, if delivered all at once) to be divided among multiple inhalation cycles.

Active Gas Sources

In some embodiments, pump 116 and accumulator 118 form together a compressed gas source (not referenced). In particular, accumulator 118 is a chamber for storing compressed gas, compressed by pump 116. Optionally, accumulator 118 is coupled with a pressure sensor for determining the pressure of the compressed gas. In the example set forth in FIG. 1A, pump 116 is an automatic pump consuming electrical power provided by a power source (e.g., a battery). Alternatively, pump 116 can be manual compressing device operated by the user. In this case, controller 108 can provide guidance to the user respective of the desired operation of the manual pump. In accordance with an alternative embodiment, pump 116 and accumulator 118 are replaced by another compressed gas source, or are augmented with additional compressed gas sources. For example, the inhaler includes a first gas source including compressed air, and a second gas source of Heliox.

The compressed gas is directed into a capsule (not shown) of medicament dry powder loaded into capsule chamber 124 (or into more than a single capsule loaded into chamber 124 or into several such chambers). The dry powder includes a medicament or combination of medicaments, and may further include other substances such as inert carriers (e.g., lactose, glucose). The compressed gas is employed for deagglomerating, aerosolizing, mixing or simply for releasing the dry powder from the capsule.

The compressed gas can be room air compressed into the accumulator. Alternatively, the compressed gas can include one of more of the following: oxygen, oxygen and room air, helium and oxygen (i.e., Heliox), and/or an anesthetic gas. Furthermore, the compressed gas can contain therapeutic ingredients (medication). Optionally, the compressed gas contains ingredients that condition the dry powder drug deagglomeration and/or the dispersion process. Optionally, the inhaler includes more than a single gas source. For example, the inhaler includes several gas sources, each containing a different gas that can be separately delivered into the capsule. Alternatively, a single gas source includes a mixture of different gases. It is noted that the inhaler can include more than a single gas source for the same gas, for example, a first gas source at which that gas is stored at a first pressure and a second gas source at which that gas is stored at a second pressure.

Adaptive Airway Restriction

In some embodiments of the current invention, valve 102 can be controlled by controller 108 (or by a separate controller) or manually controlled, such that it actively controls the inhaler restriction and can block the flow intermittently. As mentioned above, the airway restriction affects the drug deposition. Therefore, actively adapting the restriction can improve drug delivery. The restriction of airway 104 can thus be adapted, for example, to different powders, different patients, adapted according to the sensed breathing of the patient, and the like. In some embodiments, a fixed restriction (a region of reduced cross-section, for example) is provided along the airway 104.

In some embodiments, inlet valve 102 is controlled in a closed loop manner according to the inspiratory flow of the user. Thus, the restriction is automatically adapted to the breathing of the patient. Optionally, a restriction (before or after the capsule in the airway) is adjusted to control a pressure differential developed across the capsule by the inhalation of the patient (for example, in a device where gas flow through a needle is generated by pressure differentials due to patient respiration). Alternatively, inlet valve 102 is omitted from inhaler 100. Flow sensor 106 monitors the flow of fluids through airway 104. Flow sensor 106 can be implemented for example, by a pressure sensor or hot wire sensor, and the like. Flow sensor 106 provides the flow readings to controller 108 that determines accordingly various breath parameters of the patient. For example, controller 108 can determine inspiratory or expiratory flow rate, volume, phase, breath patterns, and the like.

Closed Loop Control and User Feedback

In some embodiments of the invention, inhaler 100, 200, and/or 400 provides feedback to the patient and the physician for monitoring the treatment, in real time. For example, the inhaler indicates to the user when it is ready for action, how to improve breathing for optimal drug delivery, and/or what amount of medicament was delivered. The feedback to the patient is performed by feedback interface 112, which can include visual, audio and haptic interfaces (e.g. LED lights, speaker, vibrator, and similar output interfaces). Optionally, the inhaler informs the physician about the breathing pattern of the patient and the patient compliance. The inhaler can further log additional data to be presented to the patient and the physician; for example: the time of each drug delivery, the duration of the delivery, the amount that was delivered, the breathing of the patient before, during and following delivery, the type of medicament delivered, and/or the size of the delivered particles (as determined by the deagglomeration of the powder).

In some embodiments, flow sensor 106 provides flow readings to controller 108. Thereby, flow sensor 106 enables controller 108 to coordinate the release of the dry powder with the breathing of the patient, to provide feedback to the patient, and the like. For example, controller 108 calculates the inspiratory flow rate of the patient according to the flow readings, and provides feedback to the patient for guiding how to optimize the dispensing of the medicament dry powder by modifying her breathing. In accordance with an additional example, inhaler 100 starts drug delivery when the inspiratory flow rate exceeds a threshold, and stops delivery in case the inspiratory flow rate decreases to below the threshold.

In some embodiments, inhaler 100, 200 and/or 400 (i.e., flow sensor 106 and controller 108) measures the expiratory flow rate for determining the lung capacity of the patient. Thereby, the drug delivery can be adapted to the anatomy of the patient. For example, the lung capacity of child (i.e., and the inspiratory volume) is smaller than that of an adult, and inhaler 100 can take that into consideration when coordinating active delivery of the dry powder medicament. Additionally, the expiratory flow rate of the patient can further be measured, for example, for verifying that the patient has emptied her lungs and would be ready to inhale the dispersed medicament during the following breathing cycle.

Controller 108 is, for example, a microcontroller or any other processing device that can gather data from the sensors and components of inhaler 100, as well from external sources, and accordingly control the operation of the various components of inhaler 100. For example, controller 108 can be implemented by a programmable chip, an application specific integrated circuit, a nearby processor configured to perform the functions describe herein (e.g., a desktop computer, PDA and/or cellphone), a remote processor, such as a central server, and the like. Controller can further include a memory portion, storing thereon, for example, software instructions, parameters for release conditions, range settings, look-up tables, calibration measurements, and/or saved patient data.

Data logger 110 is a module that handles all data logging operations of inhaler 100, such as breathing patterns data, dry powder dispensed quantities, dates and time, and the like. Data logger 110 enables a user, such as the patient and/or physician, to analyze treatment data in order to improve clinical outcomes.

Figure 12:
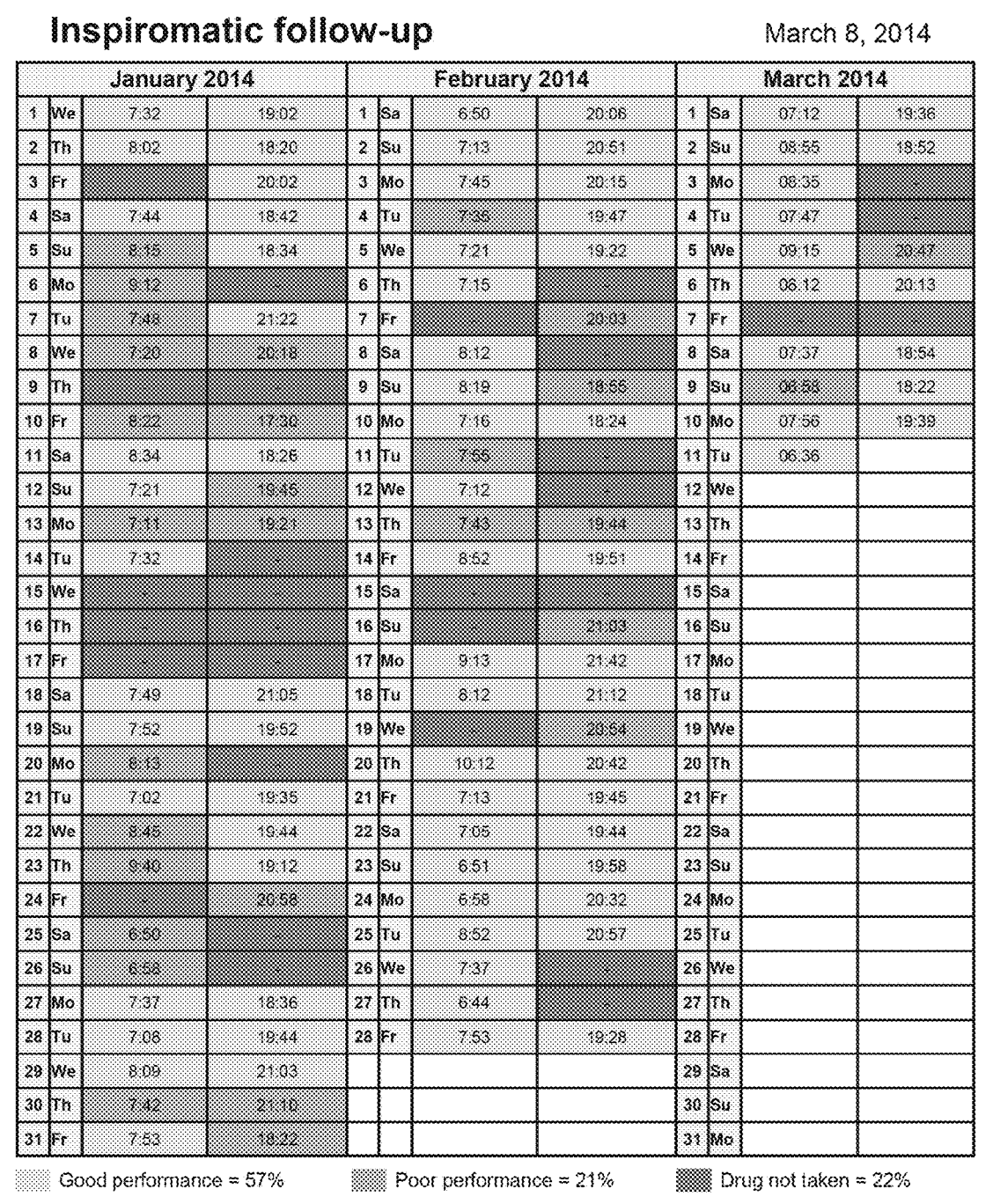

Reference is now made to FIG. 12, which shows an exemplary logged data summary sheet for an inhaler, according to some exemplary embodiments of the invention.

In some embodiments, a report of logged data comprises indications of when a medicament was taken and/or not taken (for example, day of week, day of month, month and/or time of day). Along with the time indication, an indication of good performance, poor performance, and/or drug not taken is optionally provided. Potentially, such a data sheet allows monitoring of patient performance, and if performance and/or compliance falls below an established norm, corrective action can potentially be taken. For ease of reference, performance is optionally summarized as percent good, percent poor, and/or percent of scheduled administrations not taken.

Auxiliary Sensing, Monitoring, and Control

In some embodiments of the current invention, a gas sensor is placed in fluid connection with mouthpiece 126 or with airway 104, and is further coupled with controller 108. The gas sensor detects levels of exhaled compounds (e.g. levels of carbonyls or glucose), stores the exhaled compounds data on data logger 110 and informs the user via feedback interface 112. Moreover, the gas sensor can optionally be used to monitor the therapeutic effect of the delivered drug and control the present delivery accordingly in a closed loop.

Additionally or alternatively, inhaler 100 is coupled with other sensors (either incorporated therein or external thereto) to monitor other aspects of the drug delivery process, and for modifying the drug delivery process accordingly. For example, the controller receives data from a sensor monitoring the blood pressure of the patient, monitors blood constituents, or other physiologic parameters of the patient. For instance, the controller is coupled with an external sensor that measures the oxygen levels in the blood of the patient. According to the measured oxygen levels the controller determines whether enough medicament powder was delivered.

In some embodiments, the amount of dry powder released from the capsule is determined by the flow of compressed gas into the capsule. Optionally, the amount of released powder is controlled by valve 102 that can be timed to shut by controller 108 according to a desired delivery amount, according to a measurement of the flowing powder, and the like.

Figure 13A:
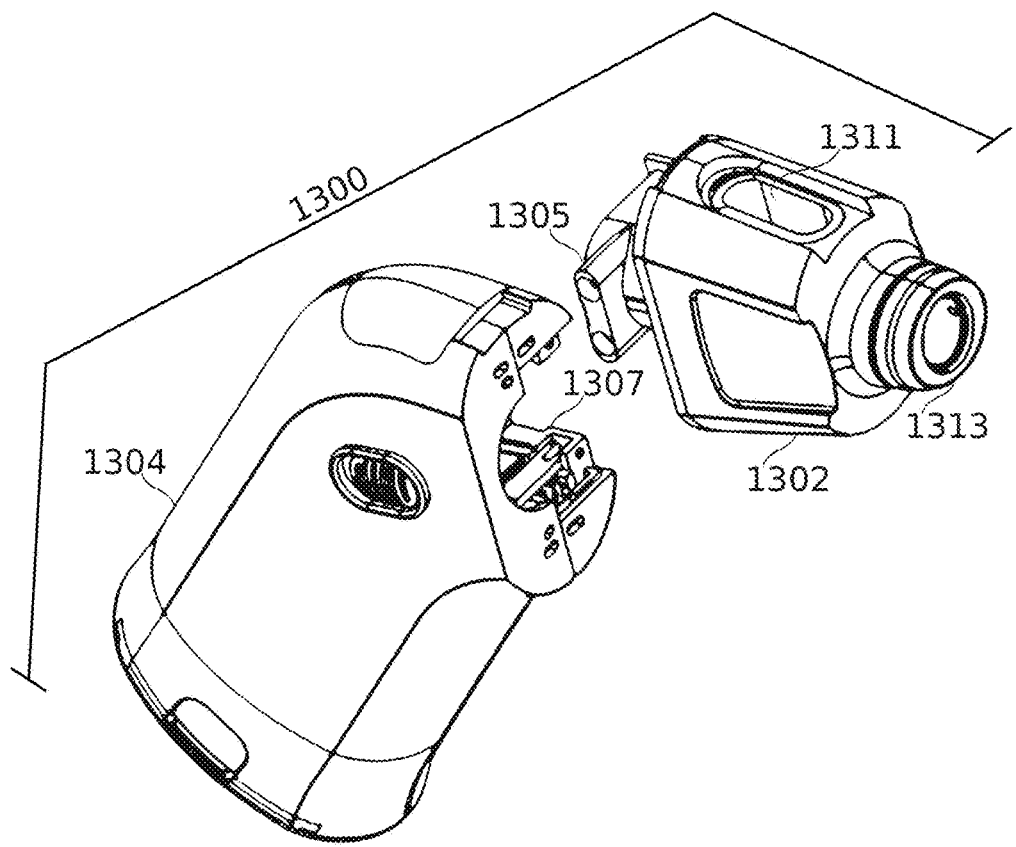
FIGS. 13A-13C schematically illustrate an inhaler with replaceable head, according to some exemplary embodiments of the invention.
Figure 13B:
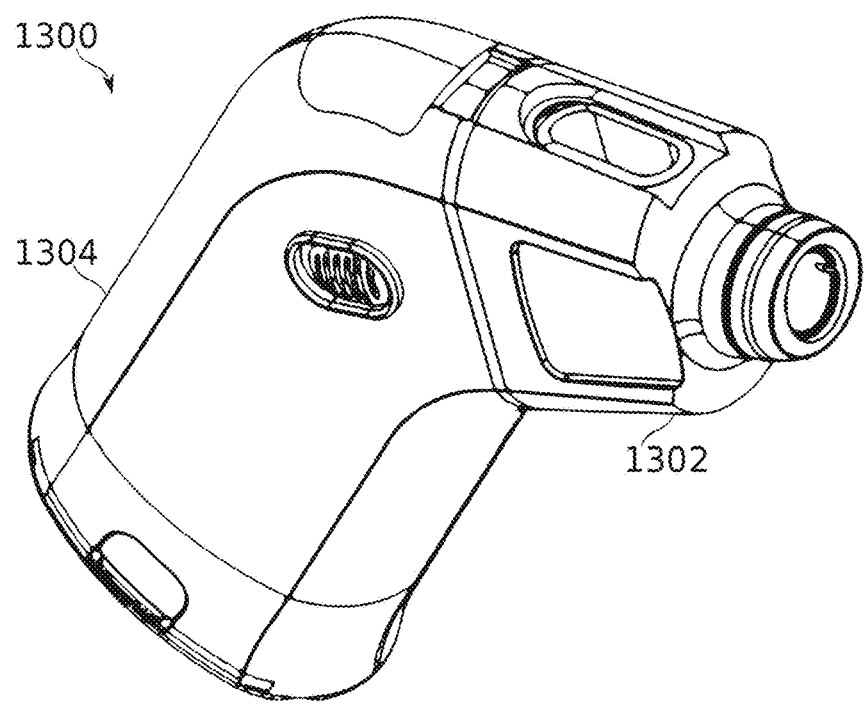

Optionally, one or more sensors are used for detecting one or more of a variety of release conditions, such as flow rate sensor, heart rate sensor, blood analyzing sensors, vacuum sensors, and the like. As mentioned above, a flow sensor acquires flow readings of the inspiratory (or expiratory) flow rate of the patient. Examples of flow sensors include a laminar flow meter, a thermal flow meter, a coriolis flow meter, an ultrasonic flow meter and/or a variable area flow meter. Moreover, the inhaler is optionally coupled with external sensors via the communication port. For example, the inhaler receives the readings of a glucometer and a blood pressure sensor.

Inhaler User Feedback for Training

In some embodiments of the invention, a feedback interface 112 is provided as a user interface for providing feedback to the user to improve the utility of inhaler 100, 200, 400. Optionally, feedback interface 112 provides feedback to the user with respect to the breathing parameters and the medicament delivery parameters, in real time. For example, feedback interface 112 indicates to the user that an inhalation flow rate is too low and should be increased. In accordance with another example, when a threshold inspiratory volume is exceeded (i.e., indicating that a sufficient amount of medicament powder was inhaled), feedback interface 112 signals to the patient that the prescribed amount of powder was delivered, or that the delivered drug reached the target site. Thus, the patient is reassured that the drug was delivered. Patient reassurance is potentially important for the ease of mind of the patient, as is compliance with the prescribed treatment. Furthermore, patient reassurance can induce a desired placebo effect in addition to the chemical and biological effects of the delivered drug.

Optionally, feedback interface 112 is used for training purposes. In this case, the inhaler is optionally used with no drug loaded, or loaded with a drug capsule containing placebo. The patient attaches the inhaler mouthpiece (or facemask) to her mouth, and inhales. Feedback interface 112 indicates to the patient how to modify her breathing for optimizing drug delivery. Optionally, the interface is designed to monitor exhaling, and/or exhaling and inhaling together, for example to train a user how to clear the lungs of air before use of the inhaler—even for embodiments where usual operation is triggered based on inhalation alone.

Once the patient knows how to optimize drug delivery via the inhaler, the patient can load a dry powder medicament capsule into the inhaler and begin treatment. Thereby, drug delivery is potentially increased in reliability. Optionally, the feedback interface provides feedback to the physician for allowing making treatment decisions accordingly (e.g., changing the dose of the medicament or instructing the patient about recommended breathing patterns). In some embodiments, inhaler 100 can be employed as a diagnostic device, such as, a spirometer.

In some embodiments, communication port 114 comprises a communication link allowing inhaler 100 to connect to external devices, such as data sources, processing devices, medical tools (e.g., diagnostic or treatment tools), and the like. Communication port 114 can be implemented by various communication links, such as wired communication links (e.g., USB port), wireless communication links (e.g., optical, radio frequency, sonic, ultrasonic, cellular), or a combination of more than a single communication link.

Inhaler with Replaceable Head Reference is now made to FIGS. 13A-13C, which schematically illustrate an inhaler 1300 with replaceable head 1302, according to some exemplary embodiments of the invention.

In some embodiments, an inhaler 1300 comprises a base 1304 and a replaceable head section 1302. The base 1304 and head 1302 are mated through connector regions 1307, 1305.

In some embodiments, head 1302 comprises the capsule chamber 1311, mouthpiece 1313 (alternatively, a facemask, nasal adapter, and/or interface for connecting to a facemask/adapter), and needles (not shown) which puncture and/or deliver gas to the capsule. In some embodiments, the main body of the head 1302 is rotatable with respect to the connector 1305, for example as described in relation to FIGS. 4A-4F; optionally, the rotation is used for preparatory tasks such as loading the capsule and priming the inhaler for medicament delivery. In some embodiments, one or more motions (for example, an extra rotation, a catch release, a pulling apart, and/or another motion) are used to enable removing the head, with complementary motions to replace it with a new one.

In some embodiments, the adapter connection between regions 1305 and 1307 comprises connections which provide delivery of air, and/or electrical power for functions including, for example, actuating the needle, sensing, and/or illuminating notification lamps. Optionally, all movement functions of the head 1302 (for example, capsule insertion and/or needle puncturing) are performed by mechanical operations such as relative rotation of the head body relative to the connector region 1305. Optionally, no electrical power connection to the head is required, and functions such as indications and sensing are contained entirely within the base section 1304.

In some embodiments, the base section 1304 comprises a compressed gas source (for example, a pump and accumulator), a controller, and/or a power source such as a battery. Optionally, sensors and/or notification means (LEDs, sound generators) are also housed in the base section. Optionally, all sensors and/or notification means are housed in the base section.

Figure 13C:
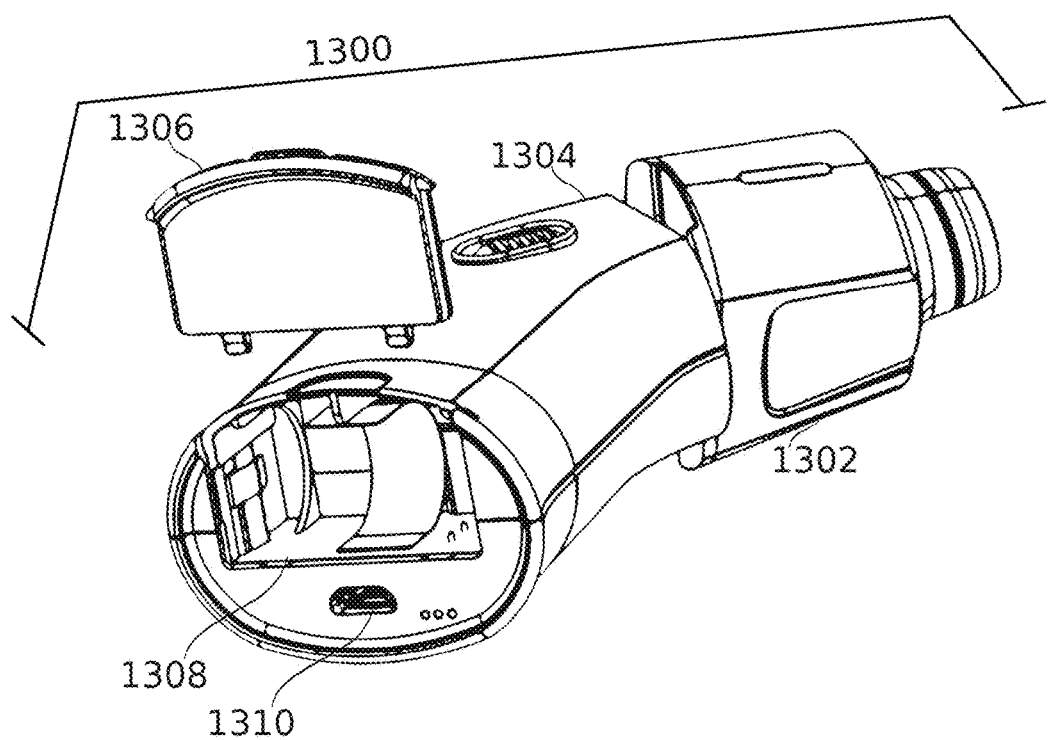
Figure 13D:
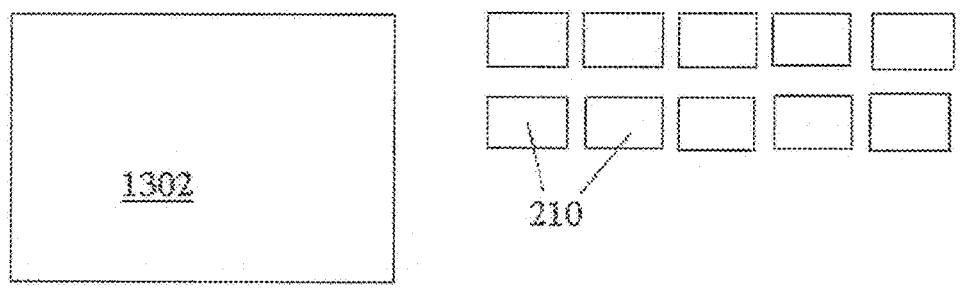
FIG. 13D schematically illustrates a block diagram of a kit including a replaceable inhaler head and ten individual capsules.

In some embodiments of the invention, head 1302 is a disposable element, used, for example, with a predetermined number of capsules before being discarded. For example, the head is used with 10 capsules, 25 capsules, 40 capsules, 60 capsules, 100 capsules, or another larger, smaller or intermediate number of capsules before being discarded. This provides a potential advantage by providing for regular replacement of inhaler portions liable to becoming contaminated with old medicament powder over time. Potentially, this reduces the chances of adverse occurrences such as clogging, needle dulling, inadvertent delivery of a too-large dose accumulated powder which suddenly dislodges, inadvertent delivery of an API breakdown product, and/or another undesired occurrence which could potentially result from wear, ageing, and/or contamination of the portions of the inhaler directly in contact with medicament during release. Optionally, each head is provided with the full number of capsules to be used together with it as a complete kit. In some embodiments, the head comprises storage for one, some (for example, 5-10 or more), up to all capsules which are provided for use with the head. For example, FIG. 13D schematically illustrates a kit including a head 1302 and ten individual capsules.

While the head is optionally replaced more often than might be economically practical for the full replacement one-piece inhaler design, another potential advantage of a two-piece design is that the base section 1304 of the device is optionally kept in service for longer than would be practical for a single-piece design. For example, the base section is kept in service for use during a service lifetime of 10 heads, 20 heads, 50 heads, 100 heads, 250 heads, or another larger, smaller, or intermediate number of heads. A potential advantage of a longer service life is reduced cost for providing the system, insofar as more expensive system components such as power, gas supply, controller, sensor, and/or indicators are optionally provided within the base section 1304.

In some embodiments of the invention, there is provision made for battery replacement and/or battery recharging. FIG. 13C shows an open battery compartment 1308, accessed through a battery service door 1306. Optionally, the battery held by compartment 1308 is a standard battery, for example, an off-the-shelf CR123A battery. Optionally, the battery is rechargeable, for example by connection through a charging connection 1310 (which is optionally also a data connection, for example as found in USB interfaces). In some embodiments, a reserve power battery is provided in addition to the main battery. This provides a potential advantage for functions such as preserving device memory and time keeping during replacement of the main battery.

Inhaler Cap

Figure 14A:
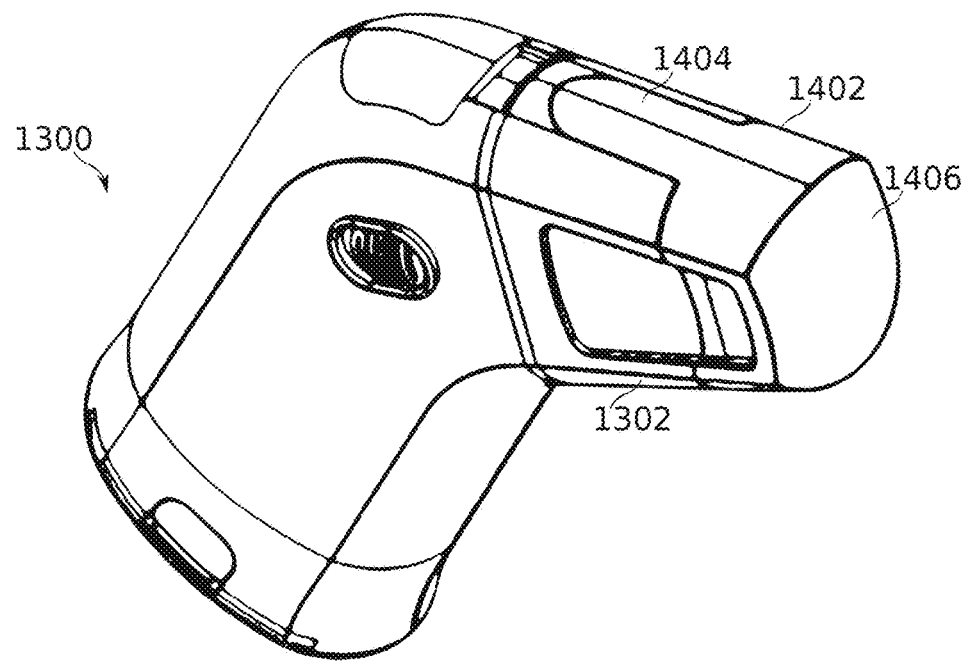
FIGS. 14A-14B show a cap for an inhaler in place and after removal, respectively, according to some exemplary embodiments of the invention.
Figure 14B:
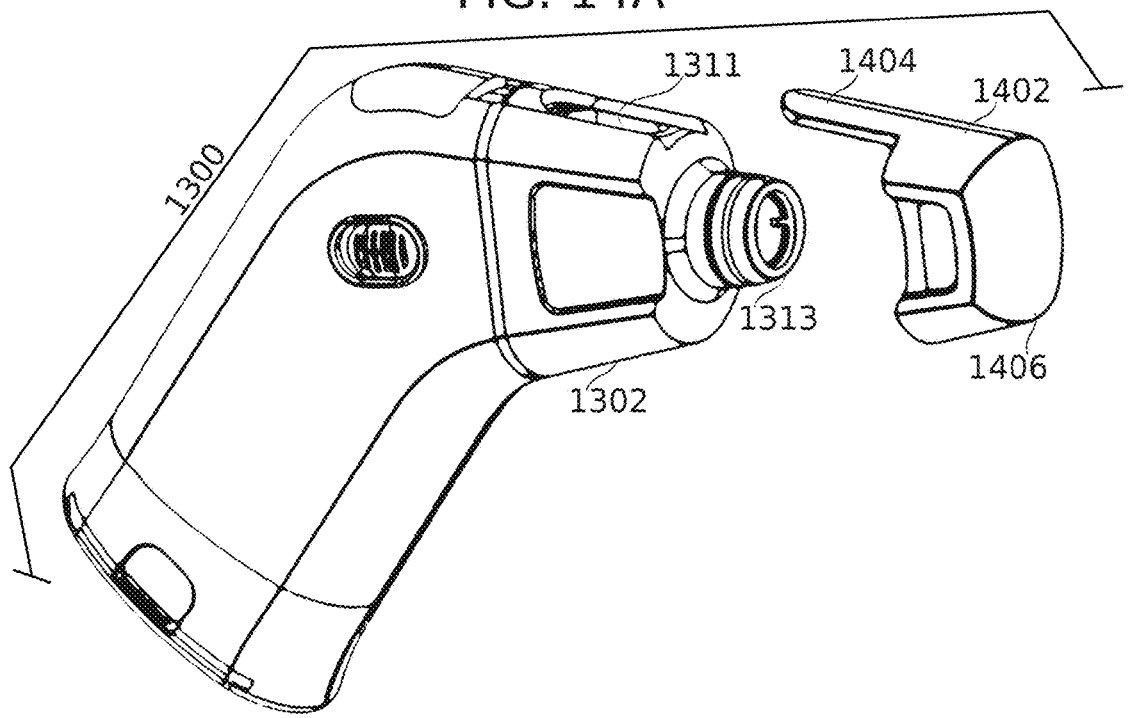

Reference is now made to FIGS. 14A-14B, which show a cap 1402 for an inhaler 1300 in place and after removal, respectively, according to some exemplary embodiments of the invention.

In some embodiments of the invention, a cap 1402 is provided for use with the inhaler 1300 (optionally, provided together with an inhaler head 1302). In some embodiments, cap 1402 interferes with the motion of head 1302 (or head subassembly), to prevent accidental priming while the cap is in place. For example a tongue 1404 of the cap protrudes to where it prevents one or more of the motions of priming. Optionally, cap 1402 also protects the inhaler/patient interface (to keep it clean and/or dry), for example, by covering mouthpiece 1313 with a protective shield region 1406. In some embodiments, tongue 1404 or another surface of the cap 1402 acts to enclose the capsule chamber 1311. Optionally, this allows a capsule to be stored in the capsule chamber 1311 without risk of accidentally priming it, so long as the cap 1402 remains in place.

Examples of Operation Details

Synchronization to Respiration

Figure 5:
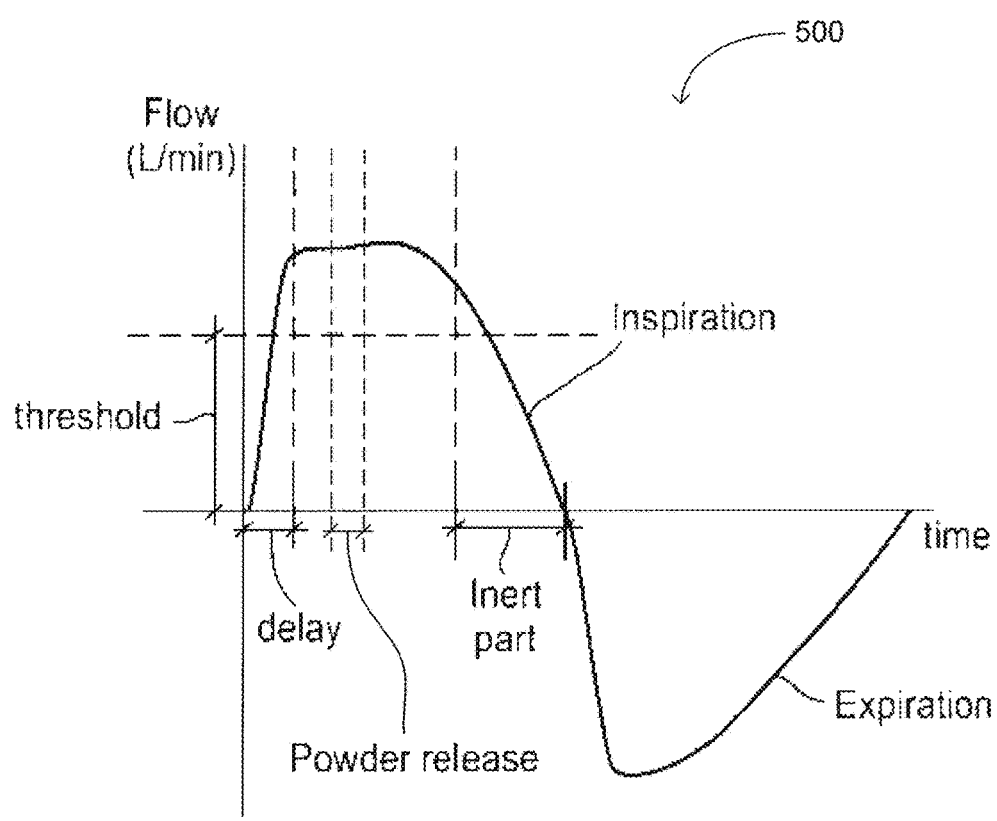
FIG. 5 schematically illustrates breathing rate curve, according to some exemplary embodiments of the invention.

Reference is now made to FIG. 5, which is a schematic illustration of breathing rate curve 500, according to some exemplary embodiments of the invention.

Breathing rate curve 500 (i.e., or flow rate curve 500) depicts the flow rate of the patient as calculated according to a flow sensor of an inhaler (e.g., inhaler 100 of FIG. 1A), versus the time, during a single breathing cycle of the patient. The breathing cycle includes an inspiratory phase and an expiratory phase.

A flow 'threshold', in some embodiments, represents the minimal flow rate of the patient at which drug is delivered. The threshold is determined according to the type of dry powder delivered, according to the desired target area for delivery of the powder, and according to other parameters. The flow threshold, as well as other delivery parameters, can be pre-set in the device software (e.g., by the inhaler manufacturer or by the manufacturer of the dry powder medicament). Additionally or alternatively, the flow threshold and other delivery parameters are set by the physician, by the patient, or by a caregiver.

A time 'delay', in some embodiments, represents the duration of waiting period (i.e., a pause) of the inhaler device from the beginning of a breathing cycle (i.e., of the inspiratory phase of the breathing cycle) before delivering the dry powder. An 'inert' part of the inspiratory phase represents the final portion of the inspiratory phase, at which inhaled air does not reach the lungs and only fills the upper respiratory system (e.g., the large airways and the pharynx).

The "powder release" period represents the time of delivery of the dry powder medicament within the capsule toward the patient. Specifically, the width of the "powder release" represents the duration of the drug delivery burst (or cluster of bursts, if gas delivery is so-configured). The dry powder can be fully released during one inhalation, or released over several breathing cycles (i.e., several inhalations). Additionally, the drug can be delivered in a continuous flow, or in a cluster of bursts. The delivery bursts can occur during a single inhalation or over several inhalations.

Single Inhalation Operation

Figure 6:
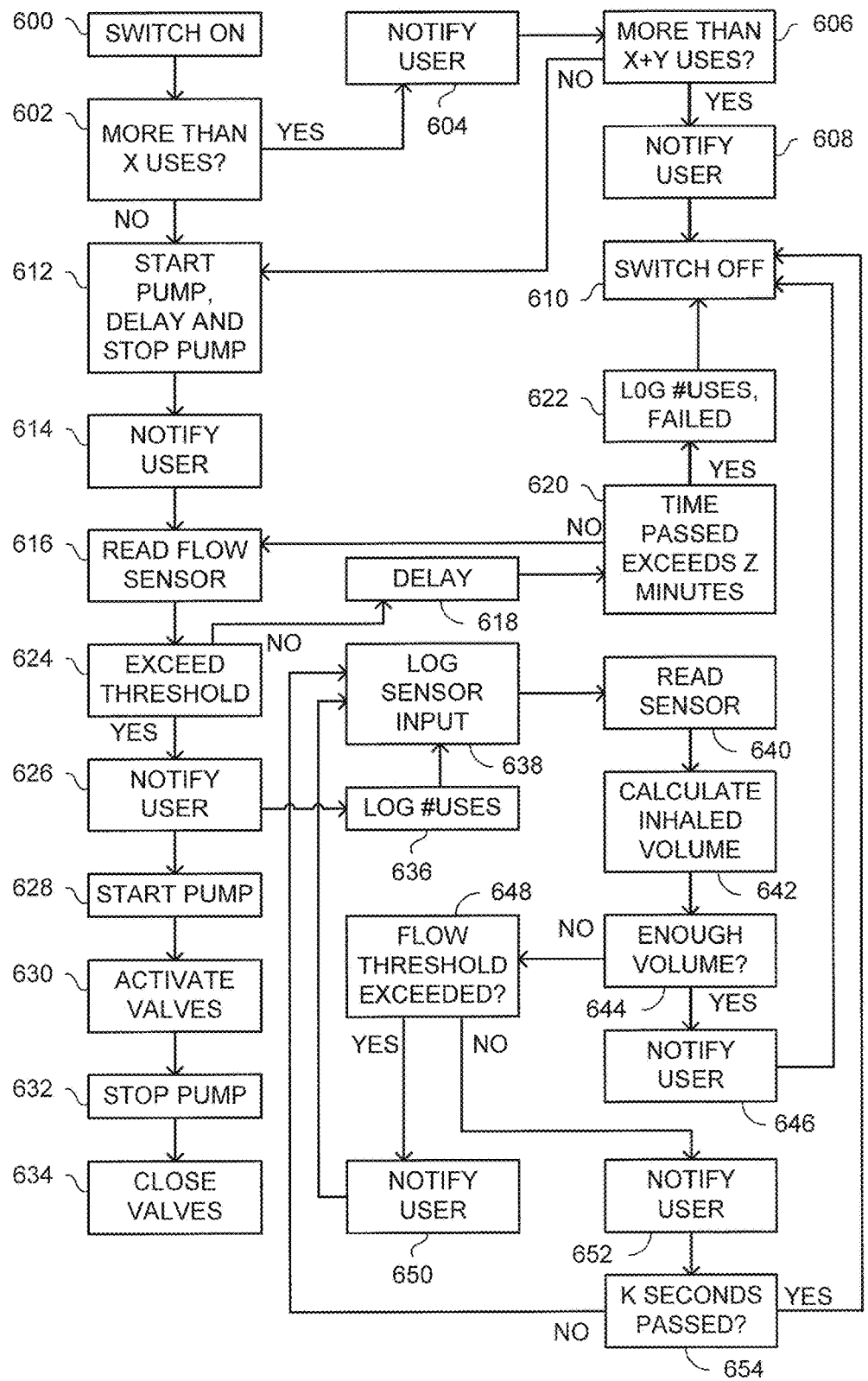
FIG. 6 schematically illustrates an exemplary method for operating an inhaler for delivering dry powder medicament during a single inhalation of the patient, according to some exemplary embodiments of the invention.

Reference is now made to FIG. 6, which is a schematic illustration of an exemplary method for operating an inhaler for delivering dry powder medicament during a single inhalation of the patient, according to some exemplary embodiments of the invention. Typically, but not exclusively, this flow of operations is used with an inhaler operated together with a mouthpiece.

At block 600, in some embodiments, the inhaler device is switched on by a user. It is noted that the inhaler device is switched on (or at least, is only ready for use) after being preloaded and primed with a dry powder capsule, for example as described in relation to FIGS. 4A-4F, including any operations of piercing required. In some embodiments, the system controller detects the loaded/primed state of the inhaler, and provides indications of ready/not ready state accordingly.

In some embodiments, the inhaler device, or an operational portion thereof, is disposed of after a predetermined number of uses. For example, in case the inhaler should be discarded after 700 uses, the inhaler can notify the user when it exceeds 650 uses, to enable the user to prepare in advance for discarding and replacing the inhaler device. Once the inhaler device exceeds 700 uses, it can be locked from further use. Blocks 602-610 as detailed hereinbelow describe the determination of the number of uses, and the notifications to the user.

At block 602, in some embodiments, it is determined whether the inhaler has been used more than X times (e.g., more than 100, 200, 700 or 1500 times, or another larger, smaller, or intermediate number of uses). The number of uses of the inhaler is recorded by a data logger module of the inhaler. In case the number of uses exceeds a pre-determined number of uses, the method continues to block 604; otherwise the method continues to block 612.

At block 604, in some embodiments, the user is notified that the number of uses of the inhaler exceeds a threshold and that the inhaler should soon be replaced. The user may further be notified the remaining number of times the inhaler can be used before the inhaler should be replaced. For example, in case the inhaler should not be used more than 700 times, the user can be notified once the number of uses exceeds 650 so that she can prepare in advance for replacing the inhaler. Thus, a threshold number of uses for indicating to the user that the inhaler should be replaced soon is 650.

At block 606, in some embodiments, it is determined whether the inhaler has been used more than X+Y times (e.g., more than 120, 220, 750 or 1550 times). X+Y represent the number of uses of the inhaler recommended by the manufacturer of the inhaler. At 608, after the number of allowed uses is exceeded, the user is notified that the inhaler should be replaced. For example, in case the inhaler should be replaced after 700 times, first for each use over 650 uses the user is notified that the inhaler should be replaced soon, and when reaching 700 uses the user is notified that the inhaler should be replaced.

At block 610, in some embodiments, the inhaler is switched off such that it cannot be further used. For example, in case the number of uses of the inhaler exceeds the recommended number of uses determined by the manufacturer, the inhaler can deactivate itself and prevent the user from further employing the inhaler. Thus, the safety of the inhaler is increased by enforcing the allowed uses threshold.

At block 612, in some embodiments, in case the number of uses is below the threshold, the pump is activated for compressing gas into the accumulator of the inhaler; thereby the accumulator becomes a compressed gas source. At block 614, in some embodiments, the user is notified that the inhaler is ready for use. The user is notified by an output interface of the inhaler, such as a buzzer, a LED, a screen, other visual and or audio output interfaces, and the like.

At block 616, in some embodiments, flow sensor readings are received respective of breathing characteristics of the patient. At 624, it is determined whether a predetermined threshold for the breathing characteristics is exceeded. For example, it is determined whether the threshold inhalation flow rate or volume was exceeded (e.g. 10 liters per minute). In case the detected breath characteristic exceeds the predetermined threshold, the method continues in block 626, otherwise the method continues in block 618.

At block 618, in some embodiments, the inhaler delays its operation until the predetermined threshold for the breathing characteristics (blocks 616 and 624) is exceeded. At block 620, it is determined whether a predetermined period has been exceeded. In case the predetermined time period (e.g., 5 minutes) is exceeded, the method continues in block 622. Block 620 is directed at preventing the inhaler from being kept turned on without delivering the medicament, thereby draining the battery. In case the patient has decided not to use the inhaler, or in case the patient cannot reach the breathing parameter threshold for a predetermined period, the inhaler logs the failed attempts and turns off (blocks 622 and 610). During the delay of block 620, the flow sensor keeps on acquiring breathing readings (block 616) and in case the threshold is exceeded (block 624), the method continues to 626. At block 622, the failure to achieve the breath characteristic threshold is recorded along with metadata, such as the date and time, the use number of the inhaler, at which patient failed to reach the breathing threshold, and the like. Thereafter, at block 610, the inhaler switches off.

At block 626, in some embodiments, the user is notified that the breathing threshold was exceeded and that drug delivery can commence. Thereby, patient breathing (e.g., inhalation flow rate) is employed for triggering drug delivery, that is, employed as a release condition. At blocks 628, 630, 632 and 634, the pump is activated for compressing gas into the accumulator, and the valves are opened and closed for delivering the compressed gas into the capsule for deagglomerating, aerosolizing or releasing the dry powder from the capsule.

Additionally, after notifying the user that the breathing threshold has been exceeded (block 626), the method also follows block 636. At block 636, the number of uses, the data and the time of the current use of the inhaler are recorded (i.e., logged). At 638, the flow sensor readings are logged. At block 640, flow sensor additional readings are gathered, and at block 642 the inhaled volume is accordingly calculated. Alternatively, other breathing parameters can be calculated, such as exhaled volume.

At block 644, in some embodiments, it is determined whether the inhaled volume exceeds a predetermined threshold. In case the inhaled volume exceeds the respective threshold, the method continues in block 646, otherwise the method continues in block 648. At block 646, the user is notified that the inhaled volume was sufficient and that the drug delivery was successfully completed. Thereafter, at 610, the inhaler switches off.

At block 648, in some embodiments, in case the inhalation volume was not exceeded, it is determined whether the breath flow threshold was exceeded. If the breath flow threshold was exceeded the method follows block 650, otherwise the method follows block 652. At block 650, the user is notified that the inhalation volume threshold was not exceeded and that the breath flow threshold was exceeded. Thereafter, the method returns to block 638.

At block 652, in some embodiments, the user is notified that the inhalation volume has not reached the threshold, and that the breath flow threshold was also not exceeded. At block 654, as long as the time that passed since performance of block 652 does not exceed a short predetermined time period (e.g., 20 seconds), the method returns to block 638. Otherwise, in case the time that passed since block 652 exceeds the predetermined short time period, the moves to block 610 and the inhaler switches off. Moreover, the inhaler can notify the user before switching off, and can further log inhaler data before switching off.

Plurality of Inhalations (Facemask Operation)

Figure 7:
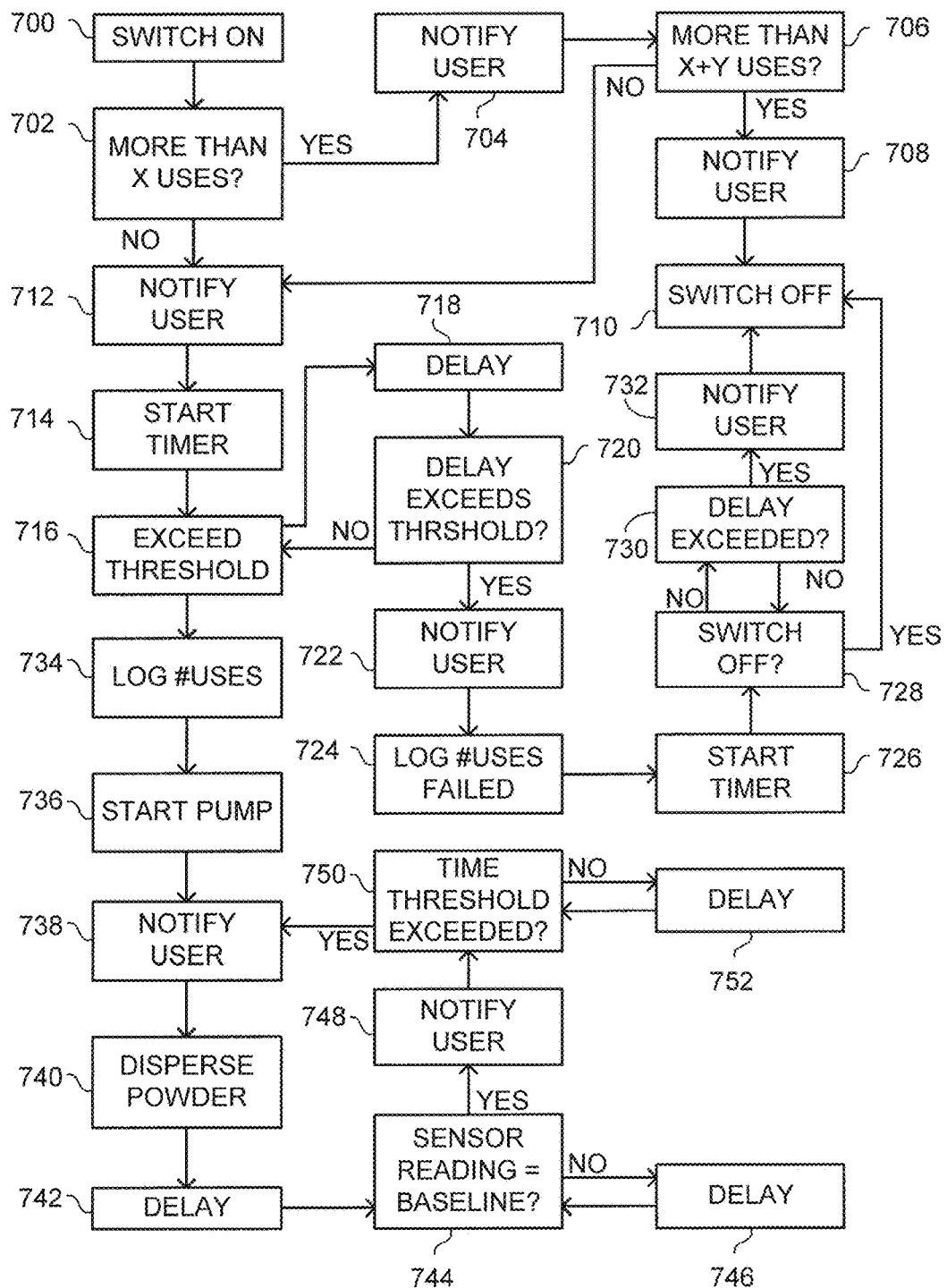
FIG. 7 schematically illustrates an exemplary method for operating an inhaler for delivering dry powder medicament in a prolonged manner over consecutive breathing cycles of the patient, according to some exemplary embodiments of the invention.
Figure 8:
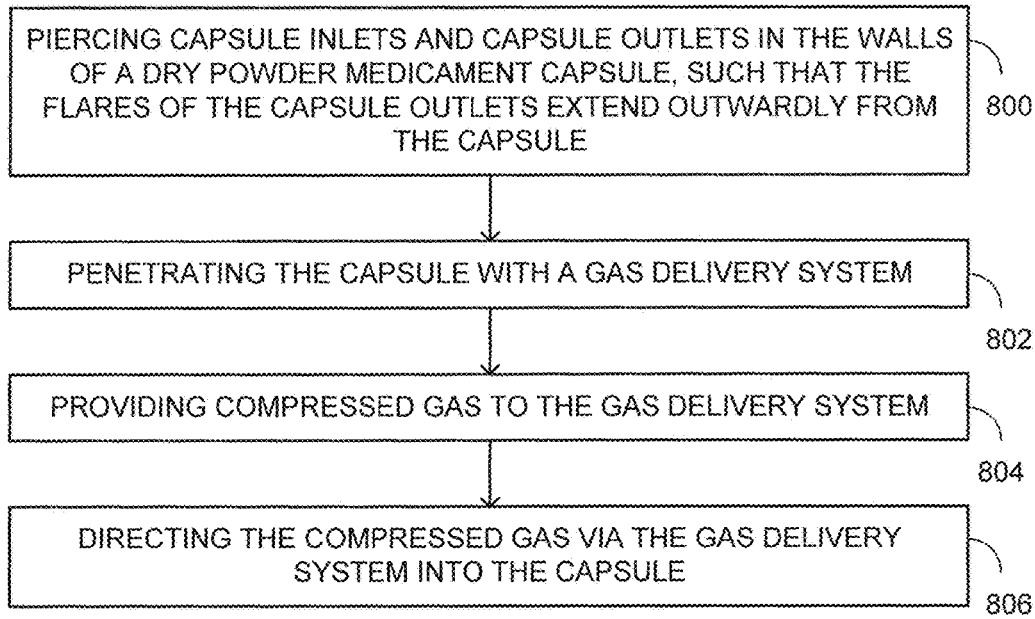
FIG. 8 schematically illustrates a method for delivering dry powder medicament to a user and piercing outward capsule outlets, according to some exemplary embodiments of the invention.

Reference is now made to FIG. 7, which is a schematic illustration of an exemplary method for operating an inhaler for delivering dry powder medicament in a prolonged manner over consecutive breathing cycles of the patient, according to some exemplary embodiments of the invention.

Blocks 700-710 of the method of FIG. 7 are substantially similar to blocks 600-610 of the method of FIG. 6 described hereinabove.

At block 712, in some embodiments, in case the number of past uses of the inhaler is below the threshold (block 702), the user is notified that the inhaler is ready for use. The user is notified by an output interface of the inhaler, such as a buzzer, a LED, a screen, other visual and or audio output interfaces, and the like.

At block 714, in some embodiments, a timer is started. At block 716, in some embodiments, a flow sensor reading is acquired and it is determined whether a breathing parameter threshold was exceeded. For example, the inhaler determines whether the inspiratory flow rate of the patient exceeds a threshold. In case the breathing parameter threshold of 716 is exceeded the method continues to block 734, otherwise the method follows block 718.

At block 718, in some embodiments, inhaler delays its operation for a short time period (e.g., 100 ms). At block 720, in some embodiments, in case the timer (block 714) exceeds a determined time period (e.g., 10 minutes), the method continues to block 622, otherwise the method returns to block 716 and checks whether the breathing parameter threshold was exceeded during the short delay.

At block 722, in some embodiments, in case the timer exceeded the determined time period, the user is notified that the time period was exceeded and that the breathing parameter threshold was not exceeded during that time period. At 724, the number of uses, the date, the time and the failed delivery are logged via the data logger of the inhaler. At block 726, in some embodiments, the timer is started. At block 728 it is determined whether to turn off the inhaler (return to block 710) or to wait and follow block 730. At block 730, the inhaler delays its operation for a short time period (e.g., 1 second) and returns to block 728.

At block 734, in some embodiments, the number of uses of the inhaler, and the current date and time, are logged via a data logger of the inhaler. At block 736, a pump of the inhaler is activated. Alternatively, in case the compressed gas source of the inhaler is not composed of a pump and an accumulator, the compressed gas source is primed (i.e., in case it requires priming). At block 738, the user is notified that drug delivery is about to commence.

At block 740, in some embodiments, the inhaler directs the compressed gas into the capsule for deagglomerating, dispersing and releasing the dry powder medicament. For example, inhaler 200 of FIG. 2 herein above, directs the compressed gas into the capsule by opening valves 204 together for 70 ms and then closing both valves for 30 ms (i.e., thereby producing a first gas flow regime within the capsule). Thereafter, only a first one of valves 204 is opened for 70 ms and then both valves are closed for 30 ms (i.e., thereby producing a second gas flow regime within the capsule). Lastly, the second one of valves 204 is opened for 70 ms and then both valves are closed for 30 ms (i.e., thereby producing a third gas flow regime within the capsule).

At block 742, in some embodiments, inhaler delays its operation for a short time period (e.g., 300 ms). At 744, a flow sensor reading is acquired, and it is determined whether the sensor reading exceeds a predetermined baseline. In case the baseline is exceeded, the method continues to block 748, otherwise the method follows block 746. At block 746, the inhaler delays its operation for a short time period (e.g., 50 ms), and then the method returns to block 744.

At block 748, in some embodiments, the user is notified that the sensor baseline reading was exceeded. At block 750, it is determined whether the breathing parameter threshold was exceeded. In case the threshold was exceeded, the method returns to block 738 for another round of drug dispersion (block 740), otherwise the method follows block 752. At block 752, the inhaler delays its operation for a short time period (e.g., 50 ms), and then the method returns to block 750. It is noted that at 750, the inhaler already dispersed the powder at least once (during an inhalation of the patient), and is ready to repeat drug dispersion. In this manner, the method of FIG. 7 is employed for controlling the inhaler for delivering the dry powder medicament in a prolonged manner, over consecutive breathing cycles of the patient.

Alternative Multi-Inhalation Operation

Figure 10A:
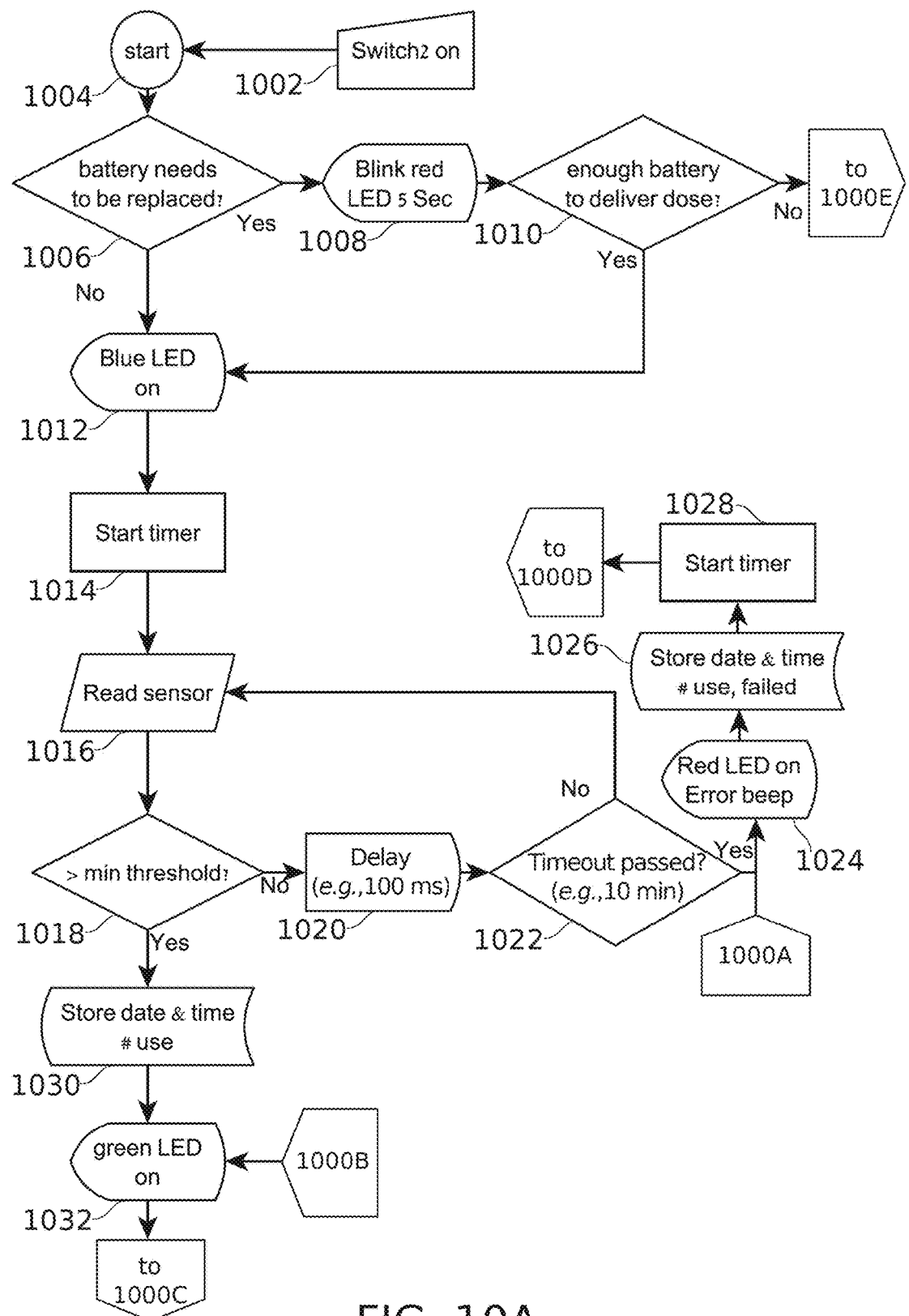
FIGS. 10A-10C together comprise a schematic illustration of an exemplary method for operating an inhaler with a disposable head for delivering dry powder medicament during a plurality of inhalations of a patient, according to some exemplary embodiments of the invention.
Figure 10B:
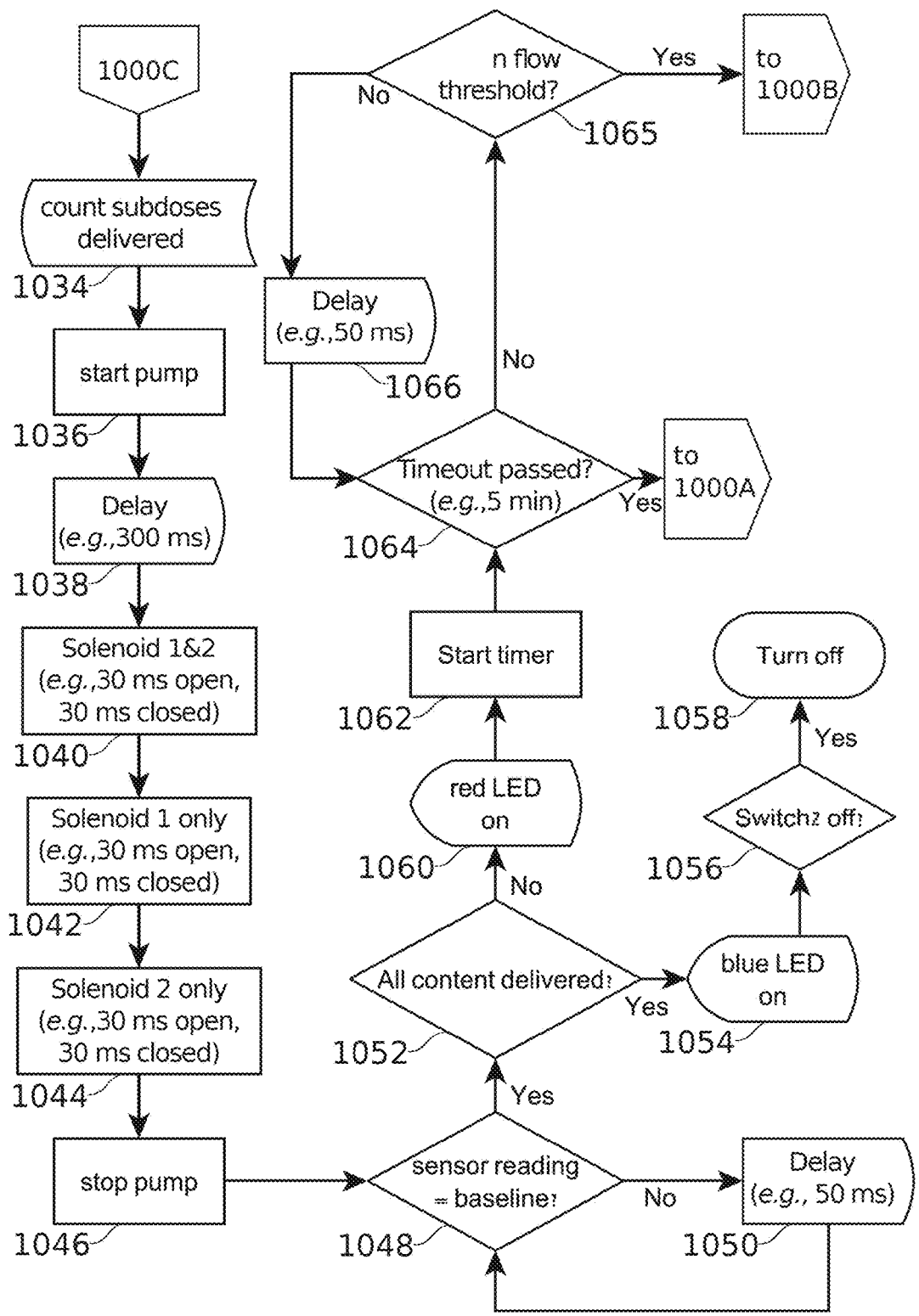
Figure 10C:
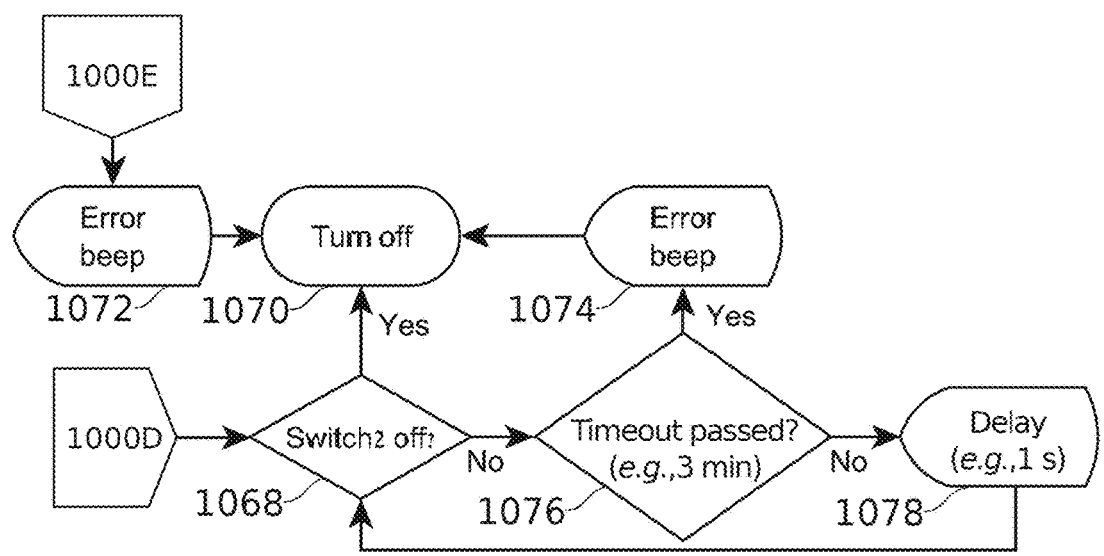

Reference is now made to FIGS. 10A-10C, which together comprise a schematic illustration of an exemplary method for operating an inhaler with a disposable head for delivering dry powder medicament during a plurality of inhalations of a patient, according to some exemplary embodiments of the invention. Typically, but not exclusively, this flow of operations is used with an inhaler operated together with a mask or nasal adapter. Mask and/or adapter use is typically with patients for whom controlled deep inhalation is difficult to obtain for some reason, so that acquisition over several breath cycles is likely to be required.

This flow of operations is for use with an inhaler having a disposable head section. A general difference from a fully disposable inhaler design is that the primary limitation on extended use is battery charge, rather than number of uses.

FIGS. 10A-10C also provide exemplary detail relating to timing of valve operation during medicament dispersal, and of other timings related to error conditions, timeouts, and/or polling cycles.

Although the flow of operations is described in connection with specific timings for various operations (for example 30 msec, 50 msec, 100 msec, 5 sec, 1 min, 3 min, 5 min, 10 min), it is to be understood that these timings should be taken as exemplary and not limiting. Although the flow of operations is described in connection with specific indications (for example blue LED, green LED, red LED, beep, blink), it is to be understood that these indications should be taken as exemplary and not limiting. It should be understood more generally that this flowchart of operations is only one particular example of operations for medicament delivery, and that other flows of operations comprising use of the invention, but having more, fewer, and/or different blocks also represent embodiments of the invention. Thresholds for activation (described, for example, in relation to a 10 l/minute inspiration rate) should also be understood to be variable to other settings: for example, 1 l/min, 5 l/min, 15 l/min, or another greater, lesser, or intermediate inspiration rate. The rate is generally chosen, for example, to have sufficient magnitude to effectively guarantee that drug will be taken into the target tissue and/or to have sufficient magnitude that it is unlikely that the flow will reverse during a drug delivery epoch.

The flowchart begins with FIG. 10A. At block 1002, in some embodiments, a power switch is turned on. At block 1004, in some embodiments, the inhaler (for example, inhaler 100, 200, 400, 1300) enters the start state. The flowchart follows from a condition in which the inhaler has already been loaded with a capsule and primed (capsule punctured, flow inlets in position).

At block 1006, in some embodiments, a determination is made whether or not the inhaler battery needs replacement and/or recharge. If so, in some embodiments, a warning indication (such as about 5 seconds of a blinking red LED) is shown at block 1008. At block 1010, in some embodiments, a determination is made whether or not there is enough battery power remaining to efficiently deliver the current dose. If so, operations continue at block 1012, with an indication (such as a blue LED) that the system is currently operable. Otherwise, operation continues at flowchart jump location 1000E (FIG. 10C), described hereinbelow.

At block 1014, in some embodiments, a timer is started, and polling begins for a minimum flow threshold to be exceeded. At block 1016, in some embodiments, flow sensor data is polled. At block 1018, in some embodiments, a determination is made whether the flow sensor data shows that current flow through the inhaler (due to patient inhalation) exceeds a minimum threshold for activation. If not, operations continue with a delay (for example of 100 msec) at block 1020.

At block 1022, in some embodiments, a determination is made whether a timeout delay (for example, 10 minutes) has expired. If not, the polling loop continues at block 1016.

However, if the timeout has occurred, an error indication (for example, a red LED and an error beep) is presented to the user at block 1024. At block 1026, in some embodiments, use data including, for example, date, time, use number, and a failure code are recorded. Then, at block 1028, in some embodiments, a new timeout timer is started, and operations continue at flowchart jump location 1000D (FIG. 10C), described hereinbelow.

Returning to block 1018: if the minimum flow threshold is exceeded, operations continue at block 1030, in some embodiments, at which use data including, for example, date, time, use number, and a use number are recorded. Optionally, the flow threshold is set to be a threshold which is expected to be exceeded at some point during a normal breath cycle (that is, an inspiration which does not require special alteration of the patient's breathing pattern).

At block 1032, in some embodiments, an indication of activation is shown (for example, illumination of a green LED). The flowchart continues with dose delivery at flowchart jump location 1000C (FIG. 10B).

Flowchart jump location 1000C (FIG. 10B) leads into block 1034, in some embodiments, at which a count of the number of sub-doses delivered is incremented (and/or a count of sub-doses remaining is decremented). The "sub-doses" are releases of a portion of the medicament contained by a capsule. In some embodiments, administration over several breaths is divided, for example, into 5, 10, or 20 sub-doses, or a larger, smaller, or intermediate number of sub-doses. This potentially allows drug dispersed into a normal breathing pattern (which does not have an extended inspiration period and/or does not have an inspiration period of dependable length) to be dependably delivered to the patient, rather than exhaled in part. Additionally or alternatively, a potential advantage of splitting drug delivery into sub-doses is to prevent administering enough powder to trigger a cough reflex. This is particularly important for a patient having reduced voluntary control of their respiration.

At block 1036, in some embodiments, a pump is activated, and after a delay at block 1038 (of, for example, 300 msec) to allow accumulation of sufficient pressure and/or arrival at a targeted respiration point, a sequence of solenoid valve operations commences, for delivering compressed air to the dry powder capsule.

The sequence given here is exemplary, assuming two solenoid valves operated in pulses. At block 1040, in some embodiments, both solenoids are opened, and gas vents from the pressure source accumulated from the pump and into each gas delivery lumen which the solenoids gate. Each lumen itself has one or more apertures into the capsule, having been positioned there during inhaler priming. The timing of opening is, for example, 30 msec open, followed by 30 msec closed. It is to be understood that another interval is used in some embodiments, for example, 10 msec, 15 msec, 50 msec, or another greater, lesser or intermediate value. It is also to be understood that the open and closed intervals can be the same or different.

At block 1042, in some embodiments, only the first solenoid is open (and then closed), resulting in a different gas flow pattern inside the capsule. The timing may be the same as for block 1040, or different. At block 1044, in some embodiments, only the second solenoid is open (and then closed). It is to be understood that the pattern of solenoids being opened is optionally presented in any order, repeating or omitting one of the patterns mentioned, and/or adding a further pattern. Opening and closing of solenoids optionally repeats for a number of cycles in the same or different combinations and/or order of combinations, with the same and/or different periods of opening and/or closing in each cycle. However, as configured for multi-inspiration use, the pattern of release defined by blocks 1038-1044 is generally defined to be brief. Potentially, this ensures that release coincides with natural inhalation by the patient. Each brief release period moreover is presumed to release only a portion of the total dose, and is therefore repeated over a sequence of inspirations, as now described.

At block 1046, in some embodiments, active dispersion (for the current inspiration) is done, and the pump operation is stopped.

At block 1048, in some embodiments, a sensor reading is taken of the inhalation flow rate, and a determination is made whether the inhalation flow rate has returned to baseline. If not, then at block 1050, a polling delay (for example, 50 msec) is introduced before the sensor baseline determination is made again.

At block 1052, in some embodiments, a determination is made whether all content has been delivered. The determination is made, for example, based on whether or not all scheduled sub-doses have been provided. In some embodiments, the determination is made by checking the count value adjusted at block 1034 against a target value (for example, 0, if the count is made by decrementing, or a register value if the count is made by incrementing).

If all content is delivered, then at block 1054, in some embodiments, an indication (such as a blue LED) is made, at block 1056, the inhaler power switch is polled until switch to the off position, and at block 1058 the inhaler is shut down.

If content remains to be delivered, then at block 1060, in some embodiments, an indication (such as a red LED) is provided, and a new timeout timer started at block 1062.

At block 1064, in some embodiments, if the timeout value (for example, 5 minutes) has passed, the flow chart branches to flowchart jump location 1000A (FIG. 10A), which in turn leads to the error indications of block 1024.

Otherwise, at block 1065, in some embodiments, the determination is again made as to whether or not the minimum respiratory flow threshold has been passed. If not, there is a delay (for example, 50 msec) at block 1066, and flow returns to the timeout test at block 1064. If so, then the flowchart branches to flowchart jump location 1000B (FIG. 10A), from which the operations of sub-dose dispersal are repeated. Optionally, sub-doses are logged as well as the main does—in this case, the repeat branch returns to block 1030, to allow re-logging, before the next phase of drug administration.

Remaining to be described is the error-condition shut down routine of FIG. 10C, and entered from either jump location 1000D (near block 1068) or 1000E (leading to block 1072).

At block 1072, in some embodiments, an error indication (such as a beep) is made, and the system turns itself off at block 1070.

At block 1068, in some embodiments, the position of the user power switch is determined. If not, then the inhaler is turned off at block 1070.

Otherwise, at block 1076, in some embodiments, a timeout check determines if sufficient time has passed (for example, three minutes) since the error to shut down automatically. If not, then there is a delay at block 1078 (of, for example, one second), and the power switch state test at block 1068 is repeated. If there has been a timeout, then at block 1074 an error indication (such as a beep) is provided to the user, and the system shuts itself down at block 1070.

Alternative Single-Inhalation Operation

Reference is now made to FIGS. 11A-11D, which together comprise a schematic illustration of an exemplary method for operating an inhaler with a disposable head for delivering dry powder medicament during a single inhalation of a patient, according to some exemplary embodiments of the invention. Typically, but not exclusively, this flow of operations is used with an inhaler operated together with a mouthpiece.

As for FIGS. 10A-10C, this flow of operations is for use with an inhaler having a disposable head section. A general difference from a fully disposable inhaler design is that the primary limitation on extended use is battery charge, rather than number of uses. FIGS. 11A-11D also provide extended detail relating to timing of valve operation during medicament dispersal, and of other timings related to error conditions, timeouts, and/or polling cycles.

Although the flow of operations is described in connection with specific timings for various operations (for example 30 msec, 100 msec, 5 sec, 10 sec, 5 min, 10 min), it is to be understood that these timings should be taken as exemplary and not limiting. Although the flow of operations is described in connection with specific indications (for example blue LED, green LED, red LED, beep, blink), it is to be understood that these indications should be taken as exemplary and not limiting. Thresholds for activation (described, for example, in relation to a 10 l/minute inspiration rate) should also be understood to be variable to other settings: for example, 1 l/min, 5 l/min, 15 l/min, or another greater, lesser, or intermediate inspiration rate. It should be understood more generally that this flowchart of operations is only one particular example of operations for medicament delivery, and that other flows of operations comprising use of the invention, but having more, fewer, and/or different blocks also represent embodiments of the invention.

Figure 11A:
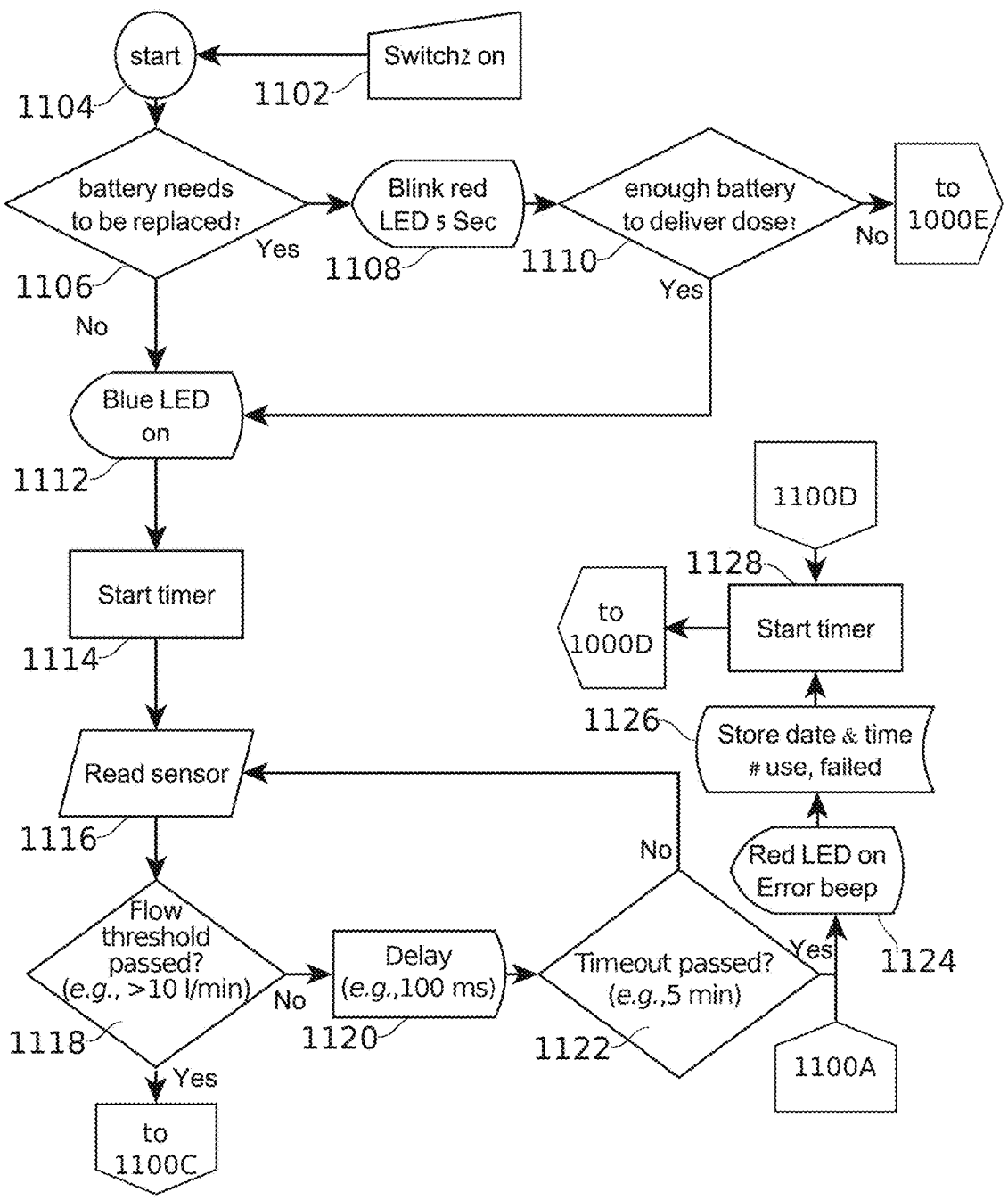
FIGS. 11A-11D together comprise a schematic illustration of an exemplary method for operating an inhaler with a disposable head for delivering dry powder medicament during a single inhalation of a patient, according to some exemplary embodiments of the invention.

The flowchart begins with FIG. 11A. Blocks 1102-1116 are generally the same as for corresponding blocks 1002-1016 of FIG. 10A. The flowchart follows from a condition in which the inhaler has already been loaded with a capsule and primed (capsule punctured, flow inlets in position).

At block 1118, in some embodiments, a determination is made whether the flow sensor data shows that current flow through the inhaler (due to patient inhalation) exceeds a minimum threshold for activation (for example, 10 l/min). If not, operations continue with a delay (for example of 100 msec) at block 1120.

Continuing to block 1122, in some embodiments, a determination is made whether a timeout delay (for example, 5 minutes) has expired. If not, the polling loop continues at block 1116.

Blocks 1124-1128 are similar in description to blocks 1024-1028. It should be noted that the shutdown sequence jumps to location 1000D (FIG. 10C), the same as for the flowchart of FIGS. 10A-10C.

Figure 11B:
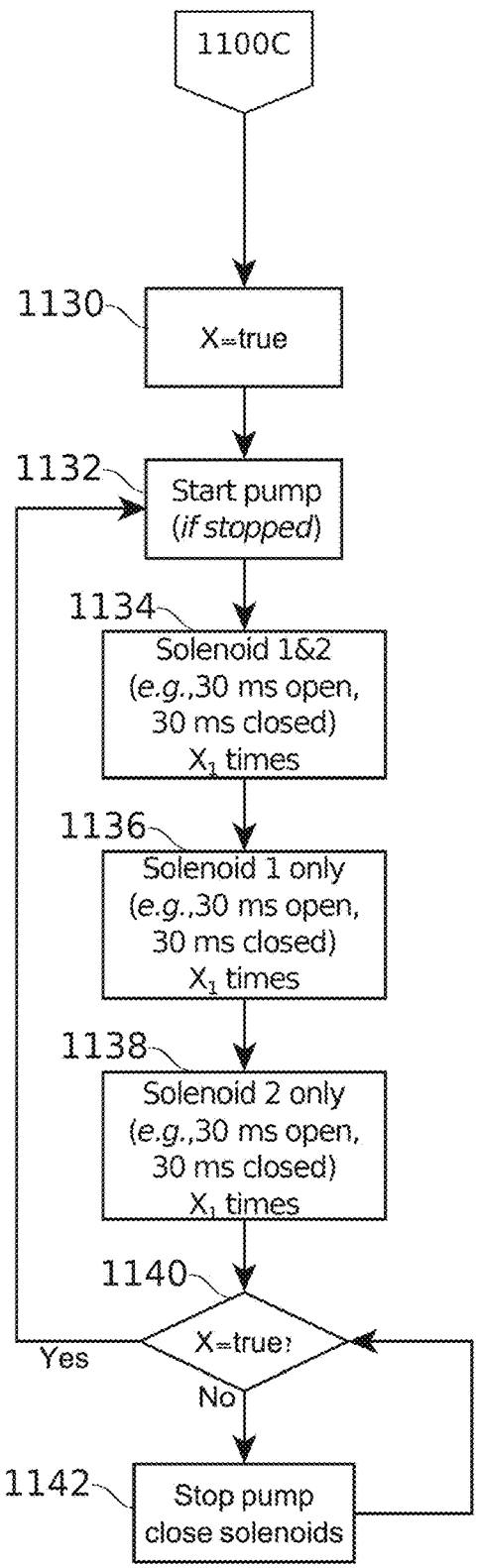
Figure 11C:
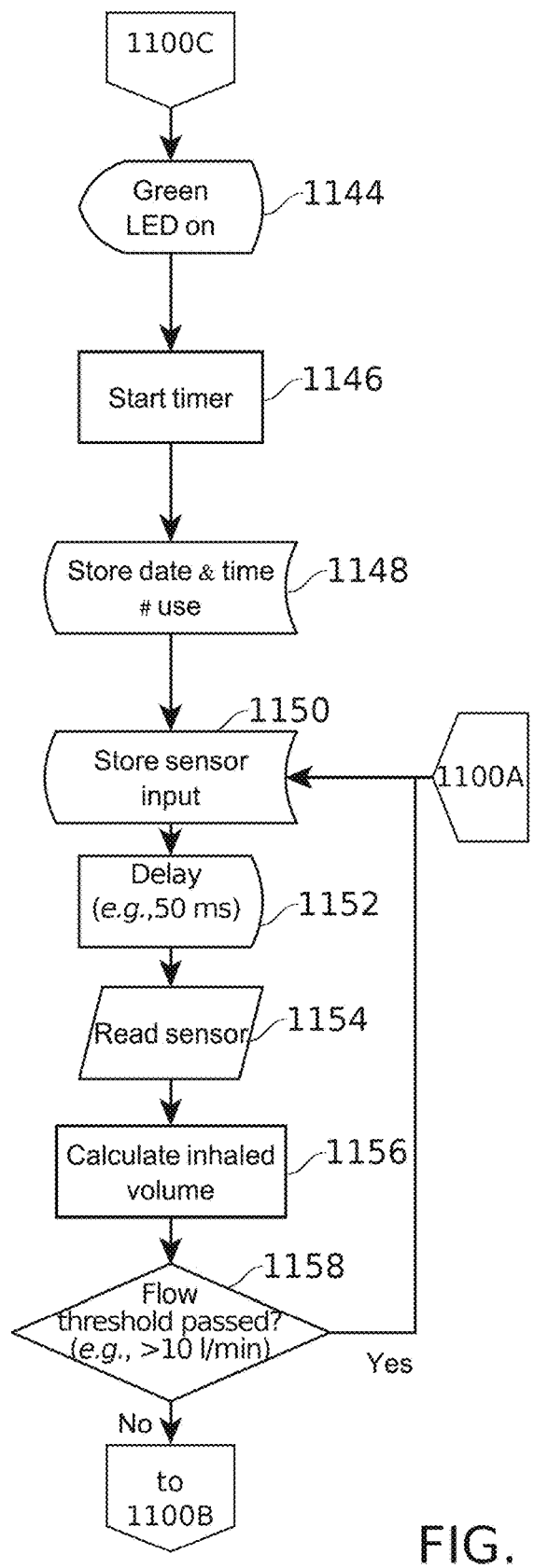
Figure 11D:
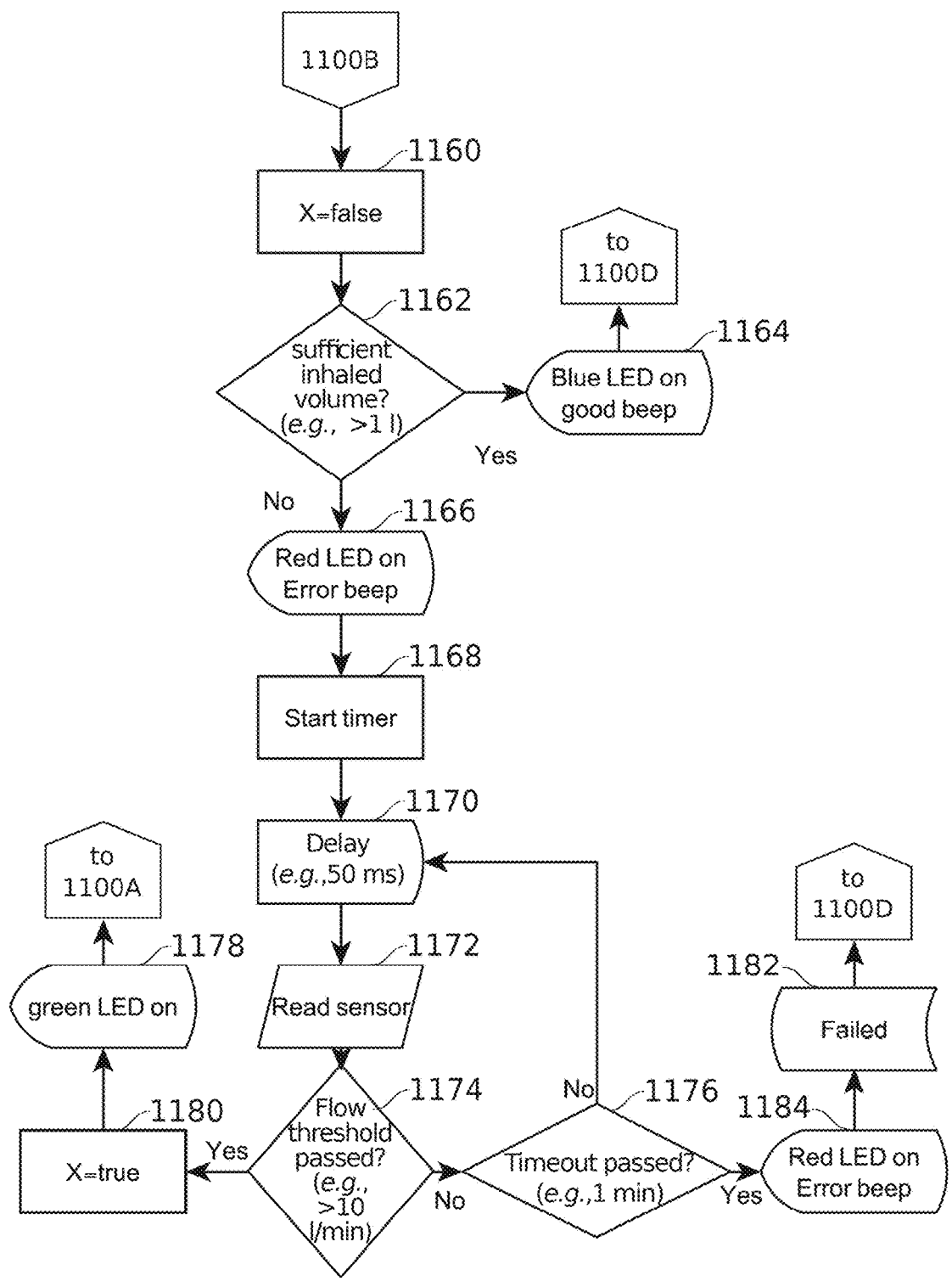

If the breathing threshold has been reached according to the determination at block 1118, then operations continue from flowchart jump location 1100C (FIGS. 11B and 11C). From this point, the flow chart splits into two branches: a medicament dispersal branch at FIG. 11B, and a monitoring and recording branch at FIG. 11C.

At block 1130, in some embodiments, the medicament dispersal branch begins, and a state variable ("X") is set to indicate that medicament dispersal should continue. This value will be set to false again by a block of the monitoring and recording branch (block 1060), as described herein below.

At block 1132, in some embodiments, the pump is started. From blocks 1134-1138, a sequence of solenoid valve operations occurs, for delivering compressed air to the dry powder capsule.

The sequence given here is exemplary, assuming two solenoid valves operated in pulses. At block 1134, in some embodiments, both solenoids are opened, and gas vents from the pressure source and into each gas delivery lumen which the solenoids gate. Each lumen itself has one or more apertures into the capsule, having been positioned there during inhaler priming. The timing of opening is, for example, 30 msec open, followed by 30 msec closed. It is to be understood that another interval is used in some embodiments, for example, 10 msec, 15 msec, 50 msec, or another greater, lesser or intermediate value. It is also to be understood that the open and closed intervals can be the same or different. In some embodiments, the opening and closing is repeated by some number of times, for example "$X_1$" times in total, where $X_1$ is an integer such as 1, 2, 3, 4, or another number. $X_1$ is optionally but not necessarily the same for each flow regime.

At block 1136, in some embodiments, only the first solenoid is open (and then closed), resulting in a different gas flow pattern inside the capsule. The timing may be the same as for block 1134, or different. At block 1138, in some embodiments, only the second solenoid is open (and then closed). The choice of flow regimes and their order as shown is exemplary only and not limiting; other orders, combinations, and/or regimes are also embodiments of the invention.

At block 1140, in some embodiments, a determination is made, based on inspection of state variable "X" as to whether or not the sequence of solenoid operations from block 1134-1138 should repeat. If so, it does. Once "X" is set to false (on the control branch), then execution passes to block 1142, at which the pump is stopped and the solenoids shut down. However periodic polling at block 1140 optionally continues, and if the state variable "X" is set to be true again, the pump is restarted, and operation resumes. If the delivery was successfully given in a single breath, there is normally no need for resumption, however. The cycling terminates when the inhaler is shut down.

Turning now to FIG. 11C: at block 1144, in some embodiments, the monitoring and recording branch of the flowchart begins (from the second jump point 1100C). An indication (such as a green LED) is presented to the user which indicates that medicament administration is underway. It should be understood that the parallel branches of control are shown for purposes of explanation, and are optionally implemented with another organization of operations with respect to their serial/parallel ordering.

At block 1146, in some embodiments, a timeout timer is started, and at block 1148, use data including, for example, date, time, use number, and a use number are recorded.

At block 1150, in some embodiments, sensor input data is stored. After a delay at block 1152 (for example, a delay of 50 msec), the sensor is read again at block 1154, and the inhaled volume is calculated at block 1156. As long as the flow is above a threshold (such as 10 l/min), the cycle returns to block 1150 (during which parallel operations manage gas flow via the solenoids which continue to open and close to release gas into the capsule).

When the flow test at block 1158 shows that flow has fallen below the threshold for inhaler operation, the flowchart operations branch to flowchart jump location 1100B (FIG. 11D), leading to block 1160.

At block 1160, in some embodiments, the "X" state variable is set false (which eventually leads to at least temporary termination of gas delivery operations to the capsule).

At block 1162, in some embodiments, the data recorded while cycling among blocks 1150-1158 is examined, and it is determined if the inhaled volume is at least some minimum value (for example, 1 liter). If so, then at block 1164, in some embodiments, a success indication (such as a blue LED illumination) is made, and execution continues at flowchart jump location 1100D (leading to block 1128, and eventually shut down of the inhaler).

Otherwise, at block 1166, in some embodiments, an indication that inhalation should be repeated to ensure full drug delivery is made (for example, a red LED with a beep). At block 1168, a new timeout timer is started. After a delay at block 1170 (of, for example, 50 msec), the flow rate sensor is read at block 1172, and the determination made at block 1174 as to whether the minimum flow rate threshold has been again exceeded. This branch of operations is normally entered only in the event of an exception—the usual operation of the device should lead to the full amount of volume being inspired during the first continuous breath exceeding the starting flow threshold.

As long as the flow threshold is not exceeded, then at block 1176, in some embodiments, a timeout check determines if more than some period has passed since the timeout timer was set (for example, more than one minute). If so, an error condition has occurred (drug not fully delivered). At block 1184, an error indication is made (for example, a red LED illumination and beep); a failed state is set at block 1182, and the shutdown sequence is entered through flowchart jump location 1100D.

Otherwise, at block 1180, in some embodiments, the state variable "X" is again set to true. At block 1178, the inhaler active indication is set (for example, a green LED illumination) and control of the flowchart returns to flowchart jump location 1100A of FIG. 11B, leading into block 1150.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An inhaler for delivering dry powder medicament contained in a capsule, the inhaler comprising:
a capsule chamber sized to fittingly hold said capsule within a capsule-holding volume;
at least one needle within the inhaler, the needle comprising a gas lumen having at least one gas outlet; and
an actuator configured to move the capsule chamber with respect to the at least one needle;
wherein the actuator is rotationally actuatable to prime the inhaler by movement of capsule chamber with respect to the needle along a path to introduce a portion of the needle across a first boundary location of the capsule-holding volume, and into an interior of the capsule-holding volume;
wherein the actuator continues the rotational actuated movement of the capsule chamber along the path with respect to the needle such that said portion of the needle introduced into said interior is introduced across a second boundary location of the capsule-holding volume, and said portion of the needle extends past the second boundary location to exit the capsule-holding volume;
wherein further continued rotational actuation of the actuator retracts the capsule chamber such that the second boundary location is retracted past the portion of the needle including the at least one gas outlet, whereby the needle including the at least one gas outlet is introduced back into the interior and away from the second boundary location; and
wherein the inhaler is configured to disperse the dry powder medicament from an exit aperture left open by the capsule wall pierced by the needle at the second boundary location, while the portion of the needle including the at least one gas outlet remains introduced back into the interior, and when the inhaler is primed with the capsule placed within the capsule-holding volume.

2. The inhaler of claim 1, wherein: when the capsule is placed within the capsule-holding volume, the actuated movement of the capsule chamber along the path to introduce the needle across the second boundary to extend past the second boundary location to exit the capsule holding volume forces a wall of the capsule from within said interior against the portion of the needle to form said exit aperture for the dry powder medicament.

3. The inhaler of claim 2, wherein the second boundary location is movable relative to a cross-section of the portion of the needle by actuated movement such that the cross-section of the portion of the needle extends past the second boundary location, wherein the cross-section defines the size of the capsule outlet.

4. The inhaler of claim 3, wherein the second boundary location is movable relative to the portion of the needle by actuated movement such that the portion of the needle extends past the second boundary location, wherein the portion of the needle comprises cross-sections of at least two different diameters on a respective at least two longitudinal sections, each said longitudinal section having a different constant-size diameter along its longitudinal extent.

5. The inhaler of claim 3, wherein, for each of said at least one needle, a cross-section configured to cross the second boundary location comprises a diameter at least as large as a diameter of a more distal portion of the needle.

6. The inhaler of claim 1, wherein a tip of the needle portion comprises a sharpened conical section.

7. The inhaler of claim 1, wherein the inhaler comprises a compressed gas source and a delivery system for gas from said compressed gas source to the lumen of the needle.

8. The inhaler of claim 7, comprising at least two spatially separated said gas outlets on the at least one needle.

9. The inhaler of claim 8, comprising at least one valve for separately controlling gas delivery via each of said gas outlets.

10. The inhaler of claim 8, wherein said at least one needle comprises at least two needles, and wherein the spatially separated gas outlets are distributed on the at least two different needles and positioned within a region of said capsule-holding volume sized to hold a single capsule.

11. The inhaler of claim 7, wherein the actuator is rotationally actuatable after a first delivery of the gas from the compressed gas source to position said gas outlet relative to at least an additional position within the capsule-holding volume at which gas is delivered into the capsule-holding volume, when the capsule is positioned in the capsule-holding volume, and while the capsule remains in said at least an additional position.

12. The inhaler of claim 7, further comprising a controller functionally connected with said gas delivery system for controlling delivery of compressed gas to said gas outlet.

13. The inhaler of claim 12, further comprising a flow sensor functionally connected with said controller; said controller determining breathing parameters of a user of said inhaler according to flow rate measurements of said flow sensor; said controller controlling the delivery of said compressed gas into said capsule, and thereby controlling delivery of said dry powder medicament to said user of said inhaler, in accordance with the determined breathing parameters.

14. The inhaler of claim 1, wherein said inhaler is configured to deliver more than a single dry powder medicament simultaneously from more than a single capsule.

15. The inhaler of claim 1, wherein said capsule chamber fittingly receives a group of physically linked capsules, forming together a continuous chain of powder compartments.

16. The inhaler of claim 1, wherein said movement of said capsule chamber with respect to the needle includes moving said needle relative to said capsule chamber.

17. A detachable module fittable to an inhaler for delivering dry powder medicament contained in a capsule, the module comprising:
   a capsule chamber sized to fittingly hold said capsule within a capsule-holding volume;
   at least one needle within the detachable module comprising a gas lumen having at least one gas outlet; and
   an actuator configured to move the capsule chamber with respect to the at least one needle;
   wherein the actuator is rotationally actuatable to prime the inhaler by movement of the capsule chamber with respect to the needle along a path to introduce a portion of the needle across a first boundary location of the capsule-holding volume, and into an interior of the capsule-holding volume;
   wherein the actuator continues the rotational actuated movement of the capsule chamber along the path with respect to the needle such that said portion of the needle introduced into said interior is introduced across a second boundary location of the capsule-holding volume, and said portion of the needle extends past the second boundary location to exit the capsule-holding volume;
   wherein continued rotational actuation of the actuator retracts the capsule chamber such that the second boundary location is retracted past the portion of the needle including the at least one gas outlet, whereby the needle including the at least one gas outlet is introduced back into the interior and away from the second boundary location; and
   wherein the inhaler is configured to disperse the dry powder medicament from an exit aperture left open by the capsule wall pierced by the needle at the second boundary location, while the portion of the needle including the at least one gas outlet remains introduced back into the interior, and when the inhaler is primed with the capsule placed within the capsule-holding volume.

18. A kit comprising the module of claim 17, and at least ten individual capsules containing dry powder medicament.

19. A method of preparing an inhaler capsule containing dry powder medicament with a capsule outlet for the medicament, the method comprising:
   introducing a needle comprising a gas lumen having at least one gas outlet into an interior of the capsule;
   puncturing a wall of the inhaler capsule by forcing the wall against the needle from a capsule interior to define the capsule outlet;
   withdrawing the capsule relative to the needle to de-obstruct the capsule outlet, positioning the at least one gas outlet within the capsule interior; and
   directing gas into the at least one gas outlet while it remains in the interior and the capsule outlet is de-obstructed, thereby releasing the dry powder medicament from the capsule.

20. The method of claim 19, wherein no more than 20% of the wall of the capsule displaced to form the capsule outlet is within the capsule interior after formation of the capsule outlet.

21. The method of claim 19, wherein forcing the wall against the needle comprises piercing the wall with the needle.

* * * * *